United States Patent [19]

Tabusa et al.

[11] Patent Number: 5,358,949
[45] Date of Patent: Oct. 25, 1994

[54] CARBOSTYRIL DERIVATIVES AND SALTS THEREOF AND ANTI-ARRHYTHMIC AGENTS CONTAINING THE CARBOSTYRIL DERIVATIVES

[75] Inventors: Fujio Tabusa; Kazuyoshi Nagami; Hironori Tsutsui, all of Tokushima, Japan

[73] Assignee: Otsuka Pharmaceutical Co., Ltd., Tokyo, Japan

[21] Appl. No.: 666,490

[22] Filed: Mar. 6, 1991

Related U.S. Application Data

[63] Continuation of Ser. No. 336,539, Apr. 11, 1989, abandoned, which is a continuation of Ser. No. 21,492, Mar. 4, 1987, abandoned.

[30] Foreign Application Priority Data

| Mar. 5, 1986 | [JP] | Japan | 61-47824 |
| Sep. 25, 1986 | [JP] | Japan | 61-226729 |
| Jan. 14, 1987 | [JP] | Japan | 62-6758 |

[51] Int. Cl.$^5$ .............. A61K 31/54; A01N 43/04; C07D 401/00
[52] U.S. Cl. .............. 514/254; 514/235.2; 514/232.5; 544/58.6; 544/521; 544/362; 544/363
[58] Field of Search ............. 544/363, 362, 321, 58.6; 514/254, 222

[56] References Cited

U.S. PATENT DOCUMENTS

| 4,014,883 | 3/1977 | Fryer et al. | 260/288 |
| 4,284,768 | 4/1981 | Santilli | 544/363 |
| 4,374,138 | 2/1983 | Haskell et al. | 422/258 |
| 4,395,414 | 4/1983 | Eistetter et al. | 424/258 |
| 4,415,572 | 11/1983 | Tominaga et al. | 544/363 |
| 4,710,507 | 12/1984 | Campbell et al. | 514/312 |
| 4,728,653 | 4/1986 | Campbell et al. | 514/312 |
| 4,735,948 | 4/1988 | Wright | 514/299 |
| 4,740,513 | 11/1988 | Campbell et al. | 514/312 |
| 4,760,064 | 7/1988 | Tominaga et al. | 544/363 |

FOREIGN PATENT DOCUMENTS

| 252919 | 5/1963 | Australia . |
| 275568 | 3/1965 | Australia . |
| WO81/00564 | 3/1981 | Australia . |
| 524419 | 5/1982 | Australia . |
| 547849 | 9/1982 | Australia . |
| 560003 | 9/1982 | Australia . |
| 553438 | 10/1985 | Australia . |
| 894236 | 2/1972 | Canada . |
| 0137177 | 4/1985 | European Pat. Off. . |
| 0145010 | 6/1985 | European Pat. Off. . |
| 0145011 | 6/1985 | European Pat. Off. . |
| 0148623 | 7/1985 | European Pat. Off. . |
| 0156261 | 10/1985 | European Pat. Off. . |
| 0166533 | 1/1986 | European Pat. Off. . |
| 0187322 | 7/1986 | European Pat. Off. . |
| 0226357 | 6/1987 | European Pat. Off. . |
| 0255134 | 2/1988 | European Pat. Off. ............ 544/363 |
| 2000747 | 9/1969 | France . |
| 2580646 | 10/1986 | France . |
| 51-125390 | 11/1976 | Japan . |
| 53-73571 | 6/1978 | Japan . |
| 54-73783 | 6/1979 | Japan . |

(List continued on next page.)

OTHER PUBLICATIONS

Davis et al., "Synthesis and Antibacterial Activities of (List continued on next page.)

*Primary Examiner*—C. Warren Ivy
*Assistant Examiner*—Raymond Covington
*Attorney, Agent, or Firm*—Finnegan, Henderson, Farabow, Garrett & Dunner

[57] ABSTRACT

Carbostyril derivatives or salt thereof, including novel compounds, having activities for curing and/or improving arrhythmia.

Some carbostyril derivatives having similar chemical structural formula to those of carbostyril derivatives of the present invention are known in the prior art references, however, above-mentioned pharmacological activities have not been known yet.

41 Claims, No Drawings

FOREIGN PATENT DOCUMENTS

| | | |
|---|---|---|
| 56-49363 | 2/1981 | Japan . |
| 56-49364 | 2/1981 | Japan . |
| 58-83677 | 5/1983 | Japan ................................. 544/363 |
| 58-83678 | 5/1983 | Japan ................................. 544/363 |
| 58-88314 | 5/1983 | Japan ................................. 544/363 |
| 59-29667 | 2/1984 | Japan . |
| 59-176276 | 10/1984 | Japan . |
| 60-42793 | 3/1985 | Japan . |
| 60-58980 | 4/1985 | Japan . |
| 60-156687 | 8/1985 | Japan . |
| 61-82 | 1/1986 | Japan . |
| 61-165383 | 8/1986 | Japan . |
| 61-191687 | 8/1986 | Japan . |
| 62-48679 | 3/1987 | Japan . |
| 62-138473 | 6/1987 | Japan ................................. 544/363 |
| 62-138490 | 6/1987 | Japan . |
| 1131501 | 10/1968 | United Kingdom . |
| 1206995 | 9/1970 | United Kingdom . |
| 1219205 | 1/1971 | United Kingdom . |
| 1425906 | 2/1976 | United Kingdom . |
| 2068943 | 8/1981 | United Kingdom . |
| 2086896 | 5/1982 | United Kingdom . |

OTHER PUBLICATIONS

Some Chloro Analogs of 3-Amino-3,4-dihydro-1-hydroxycarbostyril" (1975).

Davis et al., "Synthesis of the 3-Methyl and 4-Methyl Derivatives of 3-Amino-3,4-dihydro-1-hydroxycarbostyril and Related Compounds" (1980).

McCord et al., "The Rearrangement of 3-Amino-3,-4-dihydro-1-hydroxycarbostyril in Acidic Media (1)" (1972).

Davis et al., "Synthesis and Microbiological Properties of Some Substituted Derivatives of 3-Amino-3,4-dihydrocarbostyril" (1970).

McCord et al., "Rearrangement of Some Chlorosubstituted 3-Amino-3,4-dihydro-1-hydroxycarbostyril in Hydrogen Halide Acids" (1982).

McCord et al., "A Comparative Study of the Rearrangement of Some 6- and 7-Halo-substituted 3-Amino-3,4-dihydro-1-hydroxycarbostyrils in Concentrated Hydrohalic Acids" (1982).

McCord et al., "The Rearrangement of 3-Amino-3,-4-dihydro-1-hydroxycarbostyril to 3-Amino-3,-4-dihydro-6-hydroxycarbostyril (1)" (1982).

Beilsteins Handbuch, Der Organischen Chemie (1935).

Beilsteins Handbuch, Der Organischen Chemie (1980) (pp. 5715–5716, 5910–5911, 5925–5927, 5933–5934, 6090–6091, 6111, and 6117).

Beilsteins Handbuck, Der Organischen Chemie (1980) (pp. 6442, 6445, 6449–6450, 6463, 6657–6659, 6691–6692).

Forbis et al., "Nybomycin. VII. Preparative Routes to Nybomycin and Deoxynybomycin" (1970).

Chemical Abstracts, vol. 84, No. 25 (Jun. 21, 1976), 84:180077w to Otsuka Pharm. Co.

Chemical Abstracts, vol. 85, No. 21 (Nov. 22, 1976), 84:159912a to Otsuka Pharm. Co.

Chemical Abstracts, vol. 93, No. 5 (Aug. 4, 1980), 93:46437w, 93:46438x to Otsuka Pharm. Co.

Talati et al., "Synthesis of Potential Antimalarials: Primaquine Analogs" (1981).

Kauffmann et al., "Uber das intermediare Auftreten von 3,4-Dehydro-carbostyril and 1-Methyl-3,4-dehydro-carbostyril" (1970).

Bowman et al., "The Synthesis of Some Dialkylamino-2-quinolones" (1965).

Bowman et al., "The Synthesis of Some 3-Aminohydrocarbostyrils" (1965).

Petersen et al., "New Methods for the Preparation of 1,4-Benzodiazepiniones, Carbostyrils and Indolo[2,3-c]quinolones" (1969).

Nishimura et al., "Synthesis of 4-Hydroxy-2(1H)-quinolone Derivatives" (1970).

Eistert et al., "Darstellung and Umsetzongen von Pyridyl-(3)-und Pyridyl-(4)-diazomethan" (1966).

Weichert, "Uber threo- underytro-beta-(Aminophynyl)-serine" (1966).

Tominaga et al., "Studies on Positive Inotropic Agents. I. Synthesis of 3,4-Dihydro-6-[4-(3,4-dimethylbenzoyl)-1-piperazinyl]-2(1H)-quinolone and Related Compounds" (1984).

CARBOSTYRIL DERIVATIVES AND SALTS THEREOF AND ANTI-ARRHYTHMIC AGENTS CONTAINING THE CARBOSTYRIL DERIVATIVES

This application is a continuation of application Ser. No. 07/336,539, filed Apr. 11, 1989, now abandoned, which is itself a continuation of application Ser. No. 07/021,492, filed Mar. 4, 1987, now abandoned.

FIELD OF THE INVENTION

The present invention relates to carbostyril derivatives and salts thereof. More particularly, the present invention relates to a method for curing and/or improving arrhythmia by administering said carbostyril derivatives and to pharmaceutical compositions containing said carbostyril derivatives as the active ingredient, and to process for preparing said carbostyril derivatives.

PRIOR ART

There have been known some carbostyril derivatives having the chemical structural formula similar to those of the carbostyril derivatives of the present invention. [Cf. U.S. Pat. Nos. 3,836,657; 4,395,414; 3,202,661; 4,071,520; 3,557,117; 4,472,433; 4,097,591; 4,097,472; 4,415,572; 4,593,035; 4,558,130; 4,173,630; European Patent No. 0187322; Canadian Patent No. 894,236; French Patent No. 2,000,747; British Patent No. 1,425,706; British Patent No. 1,206,995; 1,219,205; 1,131,501; Japanese Patent Application Kokai (Laid-Open) No. 60-42793 (1985); 59-29667 (1984)]. However, the pharmacological activities of said known carbostyril derivatives are quite different from those of carbostyril derivatives according to the present invention.

SUMMARY OF THE INVENTION

It is an object of the present invention to provide carbostyril derivatives or salts thereof represented by the general formula (1).

A further object of the present invention is to provide a method for curing and/or improving arrhythmia by administering said carbostyril derivative.

A still further object of the present invention is provide a pharmaceutical composition containing said carbostyril derivative or salt thereof as the active ingredient.

Yet, still further object of the present invention is proved processes for preparing said carbostyril derivatives.

DETAILED DESCRIPTION OF PREFERRED EMBODIMENTS

Carbostyril derivatives or salts thereof of the present invention are represented by the general formula (1),

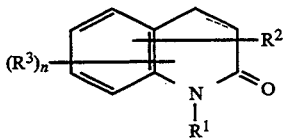

(1)

wherein $R^1$ is a hydrogen atom, a $C_1$–$C_6$ alkyl group, a lower alkenyl group, a lower alkynyl group or a phenyl-lower alkyl group;

$R^2$ is an azido group, a carbonylazido group, a phthalimido group, a pyrrolidinyl group, a pyridyl group or wherein $R^1$ is a hydrogen atom, a $C_1$–$C_{16}$ alkyl group, a lower alkenyl group, a lower alkynyl group, a phenyl-lower alkyl group, a carboxy-lower alkyl group, a phenyl-lower alkoxycarbonyl-lower alkyl group, an amido-lower alkyl group which may have lower alkyl groups as the substituents, or a 5- or 6-membered saturated heterocyclic group-substituted carbonyl-lower alkyl group;

$R^2$ is an azido group, a carbonylazido group, a phthalimide group, a pyrrolizidinyl group, a pyridyl group, a group of the formula

(wherein $R^4$ and $R^5$ are each the same or different, and are each a hydrogen atom, a lower alkyl group which may have hydroxy groups, amino groups or lower alkylamino groups as the substituents, a phenyl-lower alkanoyl group, an imidazolinyl group, a lower alkanoyl group which may have halogen atoms or a lower alkylamino groups as the substituents, a phenyl-lower alkyl group which may have lower alkoxy groups as the substituents, a phenyl group, a cycloalkyl group, a piperidinyl-lower alkanoyl group which may have phenyl-lower alkyl groups as the substituents on the piperidine ring, a lower alkenyl group, a pyrrolidinyl-lower alkanoyl group, a phenoxy-lower alkyl group which may have lower alkyl groups as the substituents on the phenyl ring, a morpholino-lower alkyl group which may have phenyl-lower alkyl groups as the substituents on the morpholine ring; further, above-mentioned $R^4$ and $R^5$ as well as the adjacent nitrogen atom being bonded thereto, together with or without other nitrogen atom, sulfur atom oxygen atom may form a 5- to 9-membered heterocyclic group; said 5- to 9-membered heterocyclic group may have 1 to 3 substituents selected from the group consisting of a phenyl group, a hydroxy group, a phenyl-lower alkyl group which may have lower alkoxy groups as the substituents on the phenyl ring, a $C_1$–$C_{10}$ alkyl group which may have 1 to 3 hydroxy groups, lower alkoxy groups or halogen atoms as the substituents, a lower alkenyl group, a lower alkoxycarbonyl-lower alkyl group, a tetrahydrofuryl-lower alkyl group, a thienyl-lower alkyl group, a cycloalkyl-lower alkyl group, a cycloalkyl group, a benzoyl-lower alkyl group which may have halogen atoms on the phenyl ring, a pyridyl-lower alkyl group, a lower alkylamino group, a lower alkynyl group, a lower alkanoyl-lower alkyl group, a phenyl-lower alkoxycarbonyl group, a group of the formula

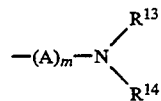

((wherein $R^{13}$ and $R^{14}$ are each the same or different, and are each a hydrogen atom, a lower alkyl group, a phenyl-lower alkyl group which may have lower alkoxy groups as the substituents on the phenyl ring; further said $R^{13}$ and $R^{14}$ as well as the nitrogen atom being bonded thereto, together with or without other nitrogen atom or oxygen atom may form a 5- or 6-membered heterocyclic group; said 5- or 6-membered heterocyclic group may have lower alkyl groups as the substituents; A is a lower alkylene group or a group of the formula

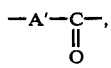

wherein A' is a lower alkylene group, m is 0 or 1)), and a benzoyl group which may have lower alkoxy groups as the substituents on the phenyl ring); or a piperidinyl group which may have lower alkyl groups or phenyl-lower alkyl groups as the substituents on the piperidine ring, a quinuclidinyl group which may have as the substituents amino groups having or without having 1 to 2 lower alkyl groups as the substituents;

$R^3$ is a lower alkyl group which may have 1 to 3 halogen atoms as the substituents, a lower alkoxy group, a hydroxy group, a halogen atom, a carboxy group, a phenyl group, a phenyl-lower alkoxy group, a lower alkenyloxy group, a lower alkanoyl-lower alkoxy group or a lower alkylaminocarbonyl-lower alkoxy group;

n is 0, 1 or 2;

the carbon-carbon bond between 3- and 4-positions in the carbostyril skeleton is a single or double bond;

further, $R^2$ and $R^3$ are each may be substituted at any position at 3 to 8 positions in the carbostyril skeleton, provided that $R^2$ and $R^3$ should not be substituted at the same position at the same time.

Carbostyril derivatives or salts thereof represented by the general formula (1) possess anti-arrhythmic activities. Specifically, said carbostyril derivatives or salts thereof do not give any effect of contraction to myocardial muscles, while they inhibit abnormal conduction disturbances formed in the case of ischemia.

In the present specification, the specific examples of the groups defined in the respective symbols of $R^1$, $R^2$, $R^3$, $R^4$ and $R^5$ are shown below.

The term "a lower alkyl group" means a straight or branched alkyl group having 1 to 16 carbon atoms, and the examples including, methyl, ethyl, propyl, isopropyl, butyl, tert-butyl, pentyl, hexyl, heptyl, octyl, nonyl, decyl, undecyl, dodecyl, tridecyl, tetradecyl, pentadecyl and hexadecyl groups and the like.

The term "a lower alkenyl group" means a straight or branched alkenyl group having 2 to 6 carbon atoms, and the examples including vinyl, allyl, 2-butenyl, 3-butenyl, 1-methylallyl, 2-pentenyl and 2-hexenyl groups and the like.

The term "a lower alkynyl group" means a straight or branched alkynyl group having 2 to 6 carbon atoms, and the examples including ethynyl, 2-propynyl, 2-butynyl, 3-butynyl, 1-methyl-2-propynyl, 2-pentynyl and 2-hexynyl groups and the like.

The term "a phenyl-lower alkyl group" means a phenylalkyl group in which the alkyl moiety is a straight or branched alkyl group having 1 to 6 carbon atoms and 1 to 2 phenyl groups may be substituted thereto, the examples including benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, diphenylmethyl and 2,2-diphenylethyl groups and the like.

The term "a lower alkylamino group" means an amino group having 1 to 2 straight or branched alkyl groups having 1 to 6 carbon atoms, and the examples including methylamino, ethylamino, propylamino, isopropylamino, butylamino, tert-butylamino, pentylamino, hexylamino, dimethylamino, diethylamino, dipropylamino, dibutylamino, dipentylamino, dihexylamino, N-methyl-N-ethylamino, N-ethyl-N-propylamino, N-methyl-N-butylamino and N-methyl-N-hexylamino groups and the like.

The term "a lower alkyl group which may have hydroxy groups, amino groups or a lower alkylamino groups as the substituents" means a straight or branched alkyl group having 1 to 6 carbon atoms which may have hydroxy groups, amino groups or amino groups having 1 to 2 straight or branched alkyl group having 1 to 6 carbon atoms as the substituents, and the examples including, in addition to the above-mentioned lower alkyl groups, hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl, aminomethyl, 1-aminoethyl, 2-aminoethyl, 3-aminopropyl, 4-aminobutyl, 5-aminopentyl, 6-aminohexyl, 1,1-dimethyl-2-aminoethyl, 2-methyl-3-aminopropyl, methylaminomethyl, ethylaminomethyl, propylaminomethyl, isopropylaminomethyl, butylaminomethyl, tert-butylaminomethyl, pentylaminomethyl, hexylaminomethyl, dimethylaminomethyl, diethylaminomethyl, dipropylaminomethyl, dibutylaminomethyl, dipentylaminomethyl, dihexylaminomethyl, N-methyl-N-ethylaminomethyl, N-ethyl-N-propylaminomethyl, N-methyl-N-butylaminomethyl, N-methyl-N-hexylaminomethyl, 2-methylaminoethyl, 1-ethylaminoethyl, 3-propylaminopropyl, 4-butylaminobutyl, 1,1-dimethyl-2-pentylaminoethyl, 5-hexylaminopentyl, 6-dimethylaminohexyl, 2-diethylaminoethyl, 1-(N-methyl-N-hexylamino)ethyl, 3-dihexylaminopropyl, 4-dibutylaminobutyl and 2-(N-methyl-N-pentylamino)ethyl groups and the like.

The term "a phenyl-lower alkanoyl group" means a phenylalkanoyl group in which the alkanoyl moiety is a straight or branched alkanoyl group having 1 to 6 carbon atoms, and the examples including 2-phenylacetyl, 3-phenylacetyl, 3-phenylpropionyl, 4-phenylbutyryl, 2-phenylbutyryl, 6-phenylhexanoyl, 2-phenylpropionyl, 3-phenylbutyryl, 4-phenyl-3-methylbutyl, 5-phenylpentanoyl and 2-methyl-3-phenylpropionyl groups and the like.

The term "a halogen atom" means a fluorine atom, chlorine atom, bromine atom and iodine atom.

The term "a lower alkanoyl group which may have halogen atoms, lower alkylamino groups as the substuents" means a straight or branched alkanoyl group having 1 to 6 carbon atoms which may have halogen atoms or amino groups having 1 to 2 straight or branched alkyl groups having 1 to 6 carbon atoms as the substituents, and the examples including formyl, acetyl, propionyl, butyryl, isobutyryl, pentanoyl, hexanoyl, 2-chloroacetyl, 3-bromopropionyl, 4-fluorobutyryl, 5-iodopentanoyl, 6-chlorohexanoyl, 3-bromoisobutyryl, methylaminoacetyl, ethylaminoacetyl, propyleuninoacetyl, isopropylaminoacetyl, butylaminoacetyl, tert-butylaminoacetyl, pentylaminoacetyl, hexylaminoacetyl, dimethylaminoacetyl, diethylaminoacetyl, dipropylaminoacetyl, dibutylaminoacetyl, dipentylaminoacetyl, dihexylaminoacetyl, N-methyl-N-ethylaminoacetyl, N-ethyl-N-propylaminoacetyl, N-methyl-N-butylaminoacetyl, N-methyl-N-hexylaminoacetyl, 3-methylaminopropionyl, 4-ethylaminobutyryl, 5-diethylaminopentanoyl, 6-hexylaminohexanoyl, 3-propylaminoisobutyryl, 3-(N-methyl-N-ethylamino)propionyl and 4-dipentylaminobutyryl groups and the like.

The term "a lower alkoxy group" means a straight or branched alkoxy group having 1 to 6 carbon atoms, and the examples including methoxy, ethoxy, propoxy, isopropoxy, butoxy, tert-butoxy, penthyloxy, and hexyloxy groups and the like.

The term "a phenyl-lower alkyl group which may have lower alkoxy groups as the substituents" means a phenylalkyl group in which the alkyl moiety is a straight or branched alkyl group having 1 to 6 carbon atoms which may have 1 to 3 straight or branched alkoxy groups having 1 to 6 carbon atoms as the substituents on the phenyl ring, and the examples including, benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl, 2-(3-methoxyphenyl)ethyl, 1-(4-methoxyphenyl)ethyl, 2-methoxybenzyl, 3-(2-ethoxyphenyl)propyl, 4-(3-ethoxyphenyl)butyl, 1,1-dimethyl-2-(4-ethoxyphenyl)ethyl, 5-(4-isopropoxyphenyl)pentyl, 6-(4-hexyloxyphenyl)hexyl, 3,4-dimethoxybenzyl, 3,4,5-trimethoxybenzyl and 2,5-dimethoxybenzyl groups and the like.

The term "a cycloalkyl group" means a cycloalkyl group having 3 to 8 carbon atoms, and the examples including cyclopropyl, cyclobutyl, cyclopentyl, cyclohexyl, cycloheptyl and cyclooctyl group and the like.

The term "a piperidinyl-lower alkanoyl group which may have phenyl-lower alkyl groups as the substituents on the piperidine ring" means a piperidinylalkanoyl group which may have phenylalkyl groups in which the alkyl moiety is a straight or branched alkyl group having 1 to 6 carbon atoms as the substituents on the piperidine ring, and the alkanoyl moiety is a straight or branched alkanoyl group having 2 to 6 carbon atoms, and the examples including, (1-piperidinyl)acetyl, 2-(1-piperidinyl)propionyl, 3-(1-piperidinyl)propionyl, 4-(1-piperidinyl)butyryl, 5-(1-piperidinyl)pentanoyl, 6-(1-piperidinyl)hexanoyl, 2,2-dimethyl-3-(1-piperidinyl)propionyl, 2-methyl-3-(1-piperidinyl)propionyl, 4-benzyl-1-1piperidinyl-acetyl, 2-[4-(2-phenylethyl)-1-piperidinyl]propionyl, 1-[4-(1-phenylethyl)-1-piperidinyl]propionyl, 4-[3-(3-phenylpropyl)-1-piperidinyl]butyryl, 5-[3-(1,1-dimethyl-2-phenylethyl)-1-piperidinyl]pentanoyl, 6-[2-(5-phenylpentyl)-1-piperidinyl]hexanoyl, 2,2-dimethyl-3-[4-(2-methyl-3-phenylpropyl)-1-piperidinyl]propionyl and 2-methyl-3-(4-benzyl-1-piperidinyl)propionyl groups and the like.

The term "a pyrrolidinyl-lower alkanoyl group" means a pyrrolidinylalkanoyl group in which the alkanoyl moiety is a straight or branched alkanoyl group having 2 to 6 carbon atoms, and the examples including, (1-pyrrolidinyl)acetyl, 2-(1-pyrrolidinyl)propionyl, 3-(1-pyrrolidinyl)propionyl, 4-(1-pyrrolidinyl)butyryl, 5-(1-pyrrolidinyl)pentanoyl, 6-(1-pyrrolidinyl)hexanoyl, 2,2-dimethyl-3-(1-pyrrolidinyl)propionyl and 2-methyl-3-(1-pyrrolidinyl)propionyl groups and the like.

The term "a lower alkoxycarbonyl-lower alkyl group" means a straight or branched alkoxycarbonylalkyl group having 1 to 6 carbon atoms in the alkoxycarbonyl moiety, and the alkyl moiety is a straight or branched alkyl group having 1 to 6 carbon atoms, and the examples including, methoxycarbonylmethyl, 3-methoxycarbonylpropyl, 4-ethoxycarbonylbutyl, 6-propoxycarbonylhexyl, 5-isopropoxycarbonylpentyl, 1,1-dimethyl-2-butoxycarbonylethyl, 20methyl-tert-butoxycarbonylpropyl, 2-pentyloxycarbonylethyl and hexyloxycarbonylmethyl groups and the like.

The term "a benzoyl group which may have lower alkoxy groups as the substituents on the phenyl groups" means a benzoyl group which may have 1 to 3 straight or branched alkoxy groups having 1 to 6 carbon atoms as the substituents on the phenyl ring, and the examples including, benzoyl, 2-methoxybenzoyl, 3-methoxybenzoyl, 4-methoxybenzoyl, 2-ethoxybenzoyl, 3-ethoxybenzoyl, 4-ethoxybenzoyl, 4-isopropoxybenzoyl, 4-pentyloxybenzoyl, 4-hexyloxybenzoyl, 3,4-dimethoxybenzoyl, 3,4-diethoxybenzoyl, 2,5-dimethoxybenzoyl, 2,6-dimethoxybenzoyl and 3,4,5-trimethoxybenzoyl groups and the like.

The term "a 5-or 6-membered heterocyclic group" formed from $R^{13}$ and $R^{14}$ as well as the adjacent nitrogen atom being bonded thereto, together with or without other nitrogen atom or oxygen atom means heterocyclic groups and examples including piperazinyl group, piperidinyl group, morpholino group and pyrrolidinyl group and the like.

The term "said 5-or 6-membered heterocyclic group may have lower alkyl groups as the substituents" means a heterocyclic group having 1 to 3 straight or branched alkyl group having 1 to 6 carbon atoms as the substituents, and the examples including, 4-methyl-1-piperidinyl, 2-methyl-1-morpholino, 2-methyl-1-pyrrolidinyl, 4-ethyl-1-piperazinyl, 3-propyl-1-morpholino, 4-isopropyl-1-piperidinyl, 3-butyl-1-pyrrolidinyl, 4-tert-butyl-1-piperazinyl, 4-pentyl-1-piperidinyl, 3-hexyl-1-morpholino, 3,4-dimethyl-1-piperazinyl, 2,4-dimethyl-1-piperazinyl and 3,4,5-trimethyl-1-piperazinyl groups and the like.

The term "a 5-to 9-membered heterocyclic group" formed from $R^4$ and $R^5$ as well as the adjacent nitrogen atom being bonded thereto, together with or without other nitrogen atom, sulfur atom or oxygen atom means a heterocyclic group, and examples including, piperazinyl group, piperidinyl group, morpholino group, pyrrolidinyl group, 1,4-diazabicyclo[4.3.0]nonyl group, 1,4-diazepinyl group, 1,4-oxazepinyl group, 1,4-thiazepinyl group, homopiperazinyl group, thiomorpholino group, indolinyl, indolyl and imidazolyl groups and the like.

The term "said 5-to 9-membered heterocyclic group may have 1 to 3 substituents selected from the group consisting of a phenyl group, a hydroxy group, a phenyl-lower alkyl group which may have lower alkyl groups as the substituents on the phenyl ring, a $C_1$-$C_{10}$ alkyl group which may have 1 to 3 hydroxy groups, lower alkoxy groups or halogen atoms as the substituents, a lower alkenyl group, a lower alkoxycarbonyl-lower alkyl group, a thienyl-lower alkyl group, a cycloalkyl-lower alkyl group, a cycloalkyl group, a benzoyl-lower alkyl group which may have halogen atoms on the phenyl ring, a pyridyl-lower alkyl group, a lower alkylamino group, a lower alkynyl group, a lower alkanoyl-lower alkyl group, a phenyl-lower alkoxycarbonyl group, a group of the formula

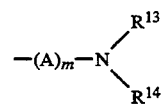

((wherein $R^{13}$ and $R^{14}$ are each the same or different, and are each a lower alkyl group, a phenyl-lower alkyl group which may have lower alkoxy groups on the phenyl ring; further $R^{13}$ and $R^{14}$ as well as the nitrogen atom being bonded thereto, together with or without other nitrogen atom or oxygen atom may form a 5-or 6-membered heterocyclic group; said 5-or 6-membered heterocyclic group may have lower alkyl groups as the substituents; A is a lower alkylene group or a group of the formula

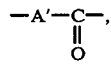

wherein A' is a lower alkylene group, m is 0 or 1)), and a benzoyl group which may have lower alkoxy groups as the substituents on the phenyl ring means a heterocyclic group which may have 1 to 3 substituents selected from the group consisting of a phenyl group, a hydroxy group, a phenylalkyl group in which the alkyl moiety is a straight or branched alkyl group having 1 to 6 carbon atoms which may have 1 to 3 straight or branched alkoxy groups having 1 to 6 carbon atoms as the substituents on the phenyl ring, a straight or branched $C_1$–$C_{10}$ alkyl group which may have 1 to 3 hydroxy groups straight or branched alkoxy groups having 1 to 6 carbon atoms or halogen atoms as the substituents, a straight or branched alkenyl group having 2 to 6 carbon atoms, an alkoxycarbonylalkyl group in which the alkyl moiety is a straight or branched alkyl group having 1 to 6 carbon atoms and the alkoxycarbonyl moiety is a straight or branched alkoxycarbonyl group having 1 to 6 carbon atoms, a thienylalkyl group in which the alkyl moiety is a straight or branched alkyl group having 1 to 6 carbon atoms, a cycloalkylalkyl group having 3 to 8 carbon atoms in which the alkyl moiety is a straight or branched alkyl group having 1 to 6 carbon atoms, a cycloalkyl group having 3 to 8 carbon atoms, a benzoylalkyl group in which the alkyl moiety is a straight or branched alkyl group having 1 to 6 carbon atoms which may have 1 to 3 halogen atoms as the substituents on the phenyl ring, a pyridylalkyl group in which the alkyl moiety is a straight or branched alkyl group having 1 to 6 carbon atoms, an alkylamido group in which the alkyl moiety is a straight or branched alkyl group having 1 to 6 carbon atoms, a straight or branched alkynyl group having 2 to 6 carbon atoms, a straight or branched alkanoylalkyl group having 1 to 6 carbon atoms in which the alkyl moiety is a straight or branched alkyl group having 1 to 6 carbon atoms, a phenylalkoxycarbonyl group in which the alkoxycarbonyl group is a straight or branched alkoxycarbonyl group having 1 to 6 carbon atoms, a group of the formula

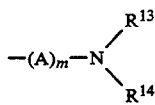

((wherein $R^{13}$ and $R^{14}$ are each the same or different, and are each a straight or branched alkyl group having 1 to 6 carbon atoms, a phenylalkyl group having 1 to 3 alkyl groups having 1 to 6 carbon atoms as the substituents on the phenyl ring; further $R^{13}$ and $R^{14}$ as well as the nitrogen atom being bonded thereto, together with or without other nitrogen atom or oxygen atom may form 5-or 6-membered heterocyclic group; said heterocyclic group may have a straight or branched alkyl group having 1 to 6 carbon atoms as the substituents on the heterocyclic group; A is a straight or branched alkylene group having 1 to 6 carbon atoms, or a group of the formula

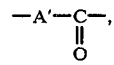

wherein A' is a straight or branched alkylene group having 1 to 6 carbon atoms; m is 0 or 1)), and a benzoyl group which may have 1 to 3 straight or branched alkoxy groups having 1 to 6 carbon atoms as the substituents on the phenyl ring, the examples including 4-phenyl-1-piperazinyl, 4-phenyl-1-piperidinyl, 3-phenylmorpholino, 2-phenyl-1-pyrrolidinyl, 4-hydroxy-1-piperazinyl, 6-phenyl-1-indolyl, 4-phenyl-1-homopiperazinyl, 3-phenylthiomorpholino, 4-hydroxy-1-piperidinyl, 2-hydroxy-1-morpholino, 3-hydroxy-1-pyrrolidinyl, 5-hydroxy-1-indolyl, 4-hydroxy-1-homopiperazinyl, 3-hydroxythiomorpholino 4-benzyl-1-piperazinyl, 4-benzyl-1-piperidinyl, 3-benzyl-1-morpholino, 2-benzyl-1-pyrrolidinyl, 4-(1-phenylethyl)-1-piperazinyl, 5-(3,4,5-trimethoxybenzyl)-1-indolyl, 4-[6-(3,4-dimethoxyphenyl)hexyl]-1-piperazinyl, 4-[2-(3,4-dimethoxyphenyl)ethyl]-1-piperazinyl, 4-benzyl-1-homopiperazinyl, 3-benzylthiomorpholino, 6-benzyl-1-indolyl, 4-[3-(3-ethoxyphenyl)propyl]-1-homopiperazinyl, 2-[4-(4-propoxyphenyl)butyl]thiomorpholino, 4-(2-phenylethyl)-1-piperidinyl, 2-(3-phenylpropyl)-1-morpholino, 3-(4-phenylbutyl)-1-pyrrolidinyl, 4-(5-phenylpentyl)-1-piperazinyl, 4-(6-phenylhexyl)-1-piperidinyl, 4-(1,1-dimethyl-2-phenylethyl)-1-piperidinyl, 4-(2-methyl-3-phenylpropyl)-1-piperazinyl, 2-methylthiomorpholino, 4-methyl-1-homopiperazinyl, 4-methyl-1-1piperazinyl, 5,6-dimethyl-1-indolyl, 3,4-dimethyl-1-piperazinyl, 2,4-dimethyl-1-piperazinyl, 4-methyl-1-piperazinyl, 2,4,5-trimethyl-1-piperazinyl, 3-methyl-1,4-diazabicyclo[4.3.0]4-nonyl, 2-methyl-1-morpholino, 2-methyl-1-pyrrolidinyl, 4-ethyl-1-piperazinyl, 3-p4opyl-1-morpholino, 4-isopropyl-1-piperidinyl, 3-butyl-1-pyrrolidinyl, 4-tert-butyl-1-piperazinyl, 4-pentyl-1-piperidinyl, 3-hexyl-1-morpholino, 4-heptyl-1-piperazinyl, 4-octyl-1-piperazinyl 4-nonyl-1-piperazinyl, 4-decyl-1-piperazinyl, 3-vinylpyrrolidinyl, 2-allylpyrrolidinyl, 4-(2-butenyl)-1-piperidinyl, 4-(1-methylallyl)-1-piperazinyl, 3-(2-pentenyl)-1-morpholino, 3-(2-hexenyl)pyrrolidinyl, 4-allyl-1-piperidinyl, 4-allyl-1-piperazinyl, 4-(2-hexenyl)-1-piperazinyl, 3-methoxycarbonylmethylpyrrolidinyl, 2-(3-methoxycarbonylpropyl)pyrrolidinyl, 4-(4-ethoxycarbonylbutyl)-1-piperidinyl, 4-(6-propoxycarbonylhexyl)-1-piperazinyl, 3-(5-isopropoxycarbonylpentyl)-1-morpholino, 4-(1,1-dimethyl-2-butoxycarbonylpropyl)-1-piperazinyl, 4-(2-methyl-3-tert-butoxycarbonylpropyl)-1-piperazinyl, 4-(2-pentyloxycarbonylethyl)-1-piperidinyl, 4-hexyloxycarbonylmethyl-1-piperazinyl, 4-ethoxycarbonylmethyl-1-piperazinyl, 4-benzoyl-1-piperazinyl, 4-benzoyl-1-piperidinyl, 3-(4-methoxybenzoyl)-1-morpholino, 2-(3-ethoxybenzoyl)-1-pyrrolidinyl, 4-(4-isopropoxybenzoyl)-1-piperazinyl, 4-(4-pentyloxybenzoyl)-1-piperidinyl, 2-(4-hexyloxybenzoyl)-1-morpholino, 4-(3,4-dimethoxybenzoyl)-1-piperazinyl, 4-(3,4-diethoxybenzoyl)-1-piperidinyl, 3-(2,5-dimethoxybenzoyl)-1-morpholino, 3-(2,6-dimethoxybenzoyl)-1-pyrrolidinyl, 4-(3,4,5-trimethoxybenzoyl)-1-piperazinyl, 3-methyl-4-(3,4-dimethoxybenzoyl)-1-piperazinyl, 4-(2-hydroxyethyl)-1-piperazinyl, 3-methyl-4-(2-hydroxyethyl)-1-piperazinyl, 4-(2-methyl-3-hydroxypropyl)-1-piperidinyl, 3-(1-hydroxyethyl)morpholino, 3-(3-hydroxypropyl-1-pyrrolidinyl, 4-(4-hydroxybutyl)-1-homopiperazinyl, 3-(5-hydroxypentyl)thiomorpholino, 6-(6-hydroxyhexyl)-1- indolinyl, 4-(2,2,2-trifluoroethyl)-1-piperazinyl, 4-iodomethyl-1-piperidinyl, 3-trifluoromethylmorpholino, 2-(1,1-dichloroethyl)-1-pyrrolidinyl, 4-tribromomethyl-1-homopiperazinyl, 3-(3-chloro-2-methylethyl)thiomorpholino, 5-(4-chlorobutyl)-1-indolyl, 4[(2-thienyl)methyl]-1-piperazinyl, 4-[1-(2-thienyl)ethyl]-1-piperidinyl, 3-[3-(2-thienyl)propyl]morpholino, 3-[4-(3-thienyl)butyl]-1-pyrrolidinyl, 4-[5-(3-thienyl)penthyl]-1-homopiperazinyl, 3-[6-(2-thienyl)hexyl]thiomorpholino, 6-[2-methyl-3-(3-thienyl)propyl]-1-indolinyl, 4-(2-cyclopropylethyl)-1-piperazinyl, 4-(1-cyclobutylethyl)-1-piperidinyl, 3-(3-cyclopentyl)morpholino, 3-(4-cyclohexylbutyl)pyrrolidinyl, 4-(5-cycloheptyl)-1-homopiperazinyl, 2-(6-cyclooctylhexyl)thiomorpholino, 4-cyclohexyl-1-piperazinyl, 4-cyclopropyl-1-piperidinyl, 2-cyclobutylmorpholino, 3-cyclopentyl-1-pyrrolidinyl, 4-cycloheptyl-1-homopiperazinyl, 3-cyclooctylthiomorpholino, 4-cyclohexyl-1-indolinyl, 4-[3-(4-fluorobenzoyl)propyl]-1-piperazinyl, 4-benzoylmethyl-1-piperidinyl, 3-[2-(3-bromobenzoyl)ethyl]morpholino, 3-[4-(2,3-dichlorobenzoyl)butyl]-1-pyrrolidinyl, 4-[5-(3,4-difluorobenzoyl)penthyl]-1-homopiperazinyl, 3-[6-(2,4,6-trichlorobenzoyl)hexyl]thiomorpholino, 4-[3-(4-pyridyl)propyl]-1-piperazinyl, 4-(2-pyridyl)methyl-1-piperazinyl, 2-[2-(3-pyridyl)ethyl]morpholino, 3-[4-(2-pyridyl)butyl]thiomorpholino, 4-[5-(4-pyridyl)pentyl]-1-homopiperazinyl, 7-[6-(2-pyridyl)hexyl]-1-indolyl, 2-diethylamido-1-pyrrolidinyl, 4-methylamido-1-piperazinyl, 4-isopropylamido-1-piperidinyl, 2-dibutylamidomorpholino, 4-dipentylamido-1-homopiperazinyl, 3-hexylamido-1-thiomorpholino, 4-(2-propynyl)-1-piperazinyl, 4-(2-butynyl)-1-piperidinyl, 3-(3-butynyl)morpholino, 2-(1-methyl-2-propynyl)-1-pyrrolidinyl, 4-(2-pentynyl)-1-homopiperazinyl, 3-(2-hexynyl)thiomorpholino, 4-ethynyl-1-indolinyl, 4-acetylmethyl-1-piperazinyl, 4-(1-propionylethyl)-1-piperidinyl, 2-(3-butyrylpropyl)morpholino, 2-(5-hexonoylpentyl)-1-pyrrolidinyl, 4-(6-acetylhexyl)-1-homopiperazinyl, 3-(2-acetylethyl)thiomorpholino, 4-acetylmethyl-1-indolyl, 4-phenylmethoxycarbonyl-1-homopiperazinyl, 4-(2-phenylethoxycarbonyl)-1-piperazinyl, 3-(3-phenylpropoxycarbonyl)morpholino, 2-(4-phenylbutoxycarbonyl)-1-pyrrolidinyl, 3-(5-phenylpentyloxycarbonyl)thiomorpholino, 5-(3-phenylpropoxycarbonyl)-1-indolinyl, 3-(6-phenylhexyloxycarbonyl)-1-piperidinyl, 2-(diethylaminomethyl)-1-pyrrolidinyl, 2-(1-pyrrolidinylmethyl)-1-pyrrolidinyl, 2-(morpholinomethyl)-1-pyrrolidinyl, 2-[(4-methyl-1-piperazinyl)methyl]-1-pyrrolidinyl, 4-(pyrrolidinylcarbonylmethyl)-1-piperazinyl, 4-[2-(1-pyrrolidinyl)ethyl]-1-piperazinyl, 4-(morpholinocarbonylmethyl)-1-piperazinyl, 4-(2-morpholinocarbonylethyl)-1-piperazinyl, 3-morpholino-1-pyrrolidinyl, 2-{N-[2-(3,4-dimethoxyphenyl)ethyl]-N-methylaminomethyl}-1-pyrrolidinyl, 3-(1-pyrrolidinyl)-1-pyrrolidinyl, 3-(4-methyl-1-piperazinyl)-1-pyrrolidinyl, 4-(1-pyrrolidinyl)-1-piperidinyl, 3-[2-{N-[3-(4-ethoxyphenyl)propyl]-N-ethylamino}ethyl]morpholino, 4-(3-morpholinopropyl)-1-homopiperazinyl, 3-[3-(1-pyrrolidinyl)carbonylpropyl]thiomorpholino, 4-(1-piperidinyl)-1-indolinyl, 3-methyl-1-imidazolyl, 3-ethyl-1-imidazolyl, 4-propyl-1-imidazolyl, 4-butyl-1-imidazolyl, 3-pentyl-1-imidazolyl, 4-hexyl-1-imidazolyl, 2-diethylaminomethyl-1-imidazolyl, 2-(2-dimethylaminoethyl)-1-imidazolyl, 4-(3-propylaminopropyl)-1-imidazolyl, 4-(4-n-butylaminobutyl)-1-imidazolyl, 2-(5-pentylaminopentyl)-1-imidazolyl, 4-(6-hexylaminohexyl)-1-imidazolyl, 4-(2-methoxyethyl)-1-piperazinyl, 2-(2-methoxyethyl)-1-imidazolyl, 4-(2-methoxypropyl)-1-piperazinyl, 4-(ethoxymethyl)-1-piperazinyl, 4-(1-ethoxyethyl)-1-piperidinyl, 3-(4-butoxybutyl)morpholino, 3-(5-hexyloxypentyl)-1-pyrrolidinyl, 4-amino-1-piperidinyl, 4-methylamine-1-piperidinyl, 4-(N-benzyl-N-methylamino)-1-piperidinyl, 4-benzylamino-1-piperidinyl, 3-amino-1-pyrrolidinyl, 3-amino-1-piperazinyl, 2-aminomorpholino, 2-ethylamino-1-piperazinyl, 3-diethylaminomorpholino, 4-propylamino-1-piperidinyl, 3-dibutylamino-1-piperidinyl, 4-pentylamino-1-piperidinyl and 2-dihexylamino-1-piperidinyl group and the like.

The term "a tetrahydrofuryl-lower alkyl group" means a tetrahydrofurylalkyl group in which the alkyl moiety is a straight or branched alkyl group having 1 to 6 carbon atoms, and the examples including, (2-tetrahydrofuryl)methyl, 2-(3-tetrahydrofuryl)ethyl, 1-(2tetrahydrofuryl)ethyl, 3-(3-tetrahydrofuryl)propryl, 4-(2-tetrahydrofuryl)butyl, 1,1-dimethyl-2-(2-tetrahydrofuryl)ethyl, 5-(3-tetrahydrofuryl)pentyl, 6-(2-tetrahydrofuryl)hexyl and 2-methyl-3-(2-tetrahydrofuryl)propyl groups and the like.

The term "a phenyl-lower alkoxy group" means a phenylalkoxy group in which the alkoxy moiety is a straight or branched alkoxy group having 1 to 6 carbon atoms, and the examples including, benzyloxy, 2-phenylethoxy, 1-phenylethoxy, 3-phenylpropoxy, 4-phenylbutoxy, 1,1-dimethyl-2-phenylethoxy, 5-phenylpentyloxy, 6-phenylhexyloxy and 2-methyl-3-phenylpropoxy groups and the like.

The term "a thienyl-lower alkyl group" means a thienylalkyl group in which the alkyl moiety is a straight or branched alkyl group having 1 to 6 carbon atoms, and the examples including, (2-thienyl)methyl, 2-(3-thienyl)ethyl, 1-(2-thienyl)ethyl, 3-(2-thienyl)propyl, 4-(3-thienyl)butyl, 1,1-dimethyl-2-(2-thienyl)ethyl, 5-(3-thienyl)pentyl, 6-(2-thienyl)hexyl and 2-methyl-3-(3-thienyl)propyl groups and the like.

The term "a cycl alkyl-lower alkyl group" means a cycloaclylalkyl group having 3 to 8 carbon atoms in which the alkyl moiety is a straight or branched alkyl group having 1 to 6 carbon atoms, and the examples including, cyclopropylmethyl, cyclobutylmethyl, cyclopentylmethyl, cyclohexylmethyl, cycloheptylmethyl, cyclooctylmethyl, 2-cyclopropylethyl, 1-cyclobutylethyl, 3-cyclopentylpropyl, 4-cyclohexylbutyl, 5-cycloheptylpenthyl, 6-cyclooctylhexyl, 2-methyl-3-cyclohexylpropyl, 2-cyclohexylethyl and 1-cyclohexylethyl groups and the like.

The term "a benzoyl-lower alkyl group which may have halogen atoms on the phenyl ring" means a benzoylalkyl group which may have 1 to 3 halogen atoms on the phenyl ring and the alkyl moiety therein is a straight or branched alkyl group having 1 to 6 carbon atoms, and the examples including, benzoylmethyl, 2-benzoylethyl, 1-benzoylethyl, 3-benzoylpropyl, 4-benzoylbutyl, 1,1-dimethyl-2-benzoylethyl, 5-benzoylpentyl, 6-benzoylhexyl, 2-methyl-3-benzoylpropyl, (2-chlorobenzoyl)methyl, 2-(3-bromobenzoyl)ethyl, 1-(4-chlorobenzoyl)ethyl, 3-(4-fluorobenzoyl)propyl, 4-(2,3-dichlorobenzoyl)butyl, 1,1-dimethyl-2-(2,4-dibromobenzoyl)ethyl, 5-(3,4-difluorobenzoyl)pentyl, 6-(2,4,6-trichlorobenzoyl)hexyl and 2-methyl-3-(2-fluorobenzoyl)propyl groups and the like.

The term "a pyridyl-lower alkyl group" means a pyridylalkyl group in which the alkyl moiety is a straight or branched alkyl group having 1 to 6 carbon atoms, and the examples including, (2-pyridyl)methyl, 2-(3-pyridyl)ethyl, 1-(4-pyridyl)ethyl, 3-(4-pyridyl)propyl, 4-(2-pyridyl)butyl, 1,1-dimethyl-2-(3-pyridyl)ethyl, 5-(4-pyridyl)pentyl, 6-(2-pyridyl)hexyl and 2-methyl-3-(3-pyridyl)propyl groups and the like.

The term "a lower alkylamido group" means an amido group being substituted with 1 to 2 straight or branched alkyl groups having 1 to 6 carbon atoms, and the examples including, methylamido, ethylamido, propylamido, isopropylamido, butylamido, tert-butylamido, pentylamido, hexylamido, dimethylamido, diethyamido, dipropylamido, dibutylamido, dipentylamido, dihexylamido, N-methyl-N-ethylamido, N-ethyl-N-propylamido, N-methyl-N-butylamido and N-methyl-N-hexylamido groups and the like.

The term "a lower alkanoyl-lower alkyl group" means an alkanoylalkyl group in which the alkyl moiety is a straight or branched alkyl group having 1 to 6 carbon atoms and the alkamoyl moiety is a straight or branched alkanoyl group having 1 to 6 carbon atoms, and the examples including, formylmethyl, 2-acetylethyl, 1-propionylethyl, 3-butyrylpropylacetylmethyl, 4-isobutyrylbutyl, 1,1-dimethyl-2-pentanoylethyl, 5-hexanoylpentyl, 6-acetylhexyt and 2-methyl-3-propionylpropyl groups and the like.

The term "a phenyl-lower alkoxycarbonyl group" means a phenylalkoxycarbonyl group in which the alkoxycarbonyl moiety is a straight or branched alkoxycarbonyl group having 1 to 6 carbon atoms, and the examples including, phenylmethoxycarbonyl, 2-phenylethoxycarbonyl, 1-phenylethoxycarbonyl, 3-phenylpropoxycarbonyl, 1-phenylethoxycarbonyl, 4-phenylbutoxycarbonyl, 1,1-dimethyl-2-phenylethoxycarbonyl, 3-phenylpropoxycarbonyl, 5-phenylpentyloxycarbonyl, 6-phenylhexyloxycarbonyl and 2-methyl-3-phenylpropoxycarbonyl groups and the like.

The term "a lower alkylene group" means a straight or branched alkylene group having 1 to 6 carbon atoms, and the examples including, methylene, ethylene, trimethylene, 2-methyltrimethylene, 2,2-dimethyltrimethylene, 1-methyltrimethylene, methylmethylene, ethylmethylene, tetramethylene, pentamethylene and hexamethylele groups and the like.

The term "a $C_1$-$C_{10}$ alkyl group which may have 1 to 3 hydroxy groups, lower alkoxy groups or halogen atom as the substituents" means a straight or branched alkyl group having 1 to 10 carbon atoms which may have 1 to 3 hydroxy groups, a straight or branched alkoxy groups having 1 to 6 carbon atoms or halogen atoms as the substituents, and the examples including, methyl, ethyl, propyl, isopropyl, butyl, tert-butyl, pentyl, hexyl, heptyl, octyl, nonyl, decyl, hydroxymethyl, 2-hydroxyethyl, 1-hydroxyethyl, 3-hydroxypropyl, 4-hydroxybutyl, 1,1-dimethyl-2-hydroxyethyl, 5-hydroxypentyl, 6-hydroxyhexyl, 2-methyl-3-hydroxypropyl, 7-hydroxyheptyl, 8-hydroxyoctyl, 7-hydroxynonyl, 6-hydroxydecyl, iodomethyl, trifluoromethyl, 2, 2-difluoroethyl, 1,1-dichloroethyl, trichloromethyl, dichloromethyl, tribromomethyl, 2,2,2-trifluoroethyl, 2,2,2-trichloroethyl, 2-fluoroethyl, 2-chloroethyl, 1-fluoroethyl, 1,2-dichloroethyl, 3,3,3-trichloropropyl, 3-fluoropropyl, 4-chlorobutyl, 3-chloro-2-methylethyl, 4-chloroheptyl, 8-chlorooctyl, 6-bromononyl, 7-fluorodecyl, methoxymethyl, 2-methoxyethyl, 2-methoxypropyl, 1-ethoxyethyl, 3-propoxypropyl, 4-butoxybutyl, 1,1-dimethyl-2-pentyloxyethyl, 5-hexyloxypentyl, 6-methoxyhexyl, 2-methyl-3-ethoxypropyl, 4-methoxyheptyl, 8-ethoxyoctyl, 6-methoxynonyl and 7-methoxydecyl groups and the like.

The term "a lower alkyl group which may have 1 to 3 halogen atoms as the substituents" means a straight or branched alkyl group having 1 to 6 carbon atoms which may have 1 to 3 halogen atoms as the substituents, and the examples including, in addition to the above-mentioned lower alkyl groups, iodomethyl, trifluoromethyl, 2,2-difluoroethyl, 1,1-dichloroethyl, trichloromethyl, dichloromethyl, tribromomethyl, 2,2,2-trifluoroethyl, 2,2,2-trichloroethyl, 2-fluoroethyl, 1,2-dichloroethyl, 3,3,3-trichloropropyl, 3-fluoropropyl, 4-chlorobutyl and 3-chloro-2-methylethyl groups and the like.

The term "a lower alkenyloxy group" means a straight or branched alkenyloxy group having 2 to 6 carbon atoms, and the example, including, vinyloxy, allyloxy, 2-butenyloxy, 3-butenyloxy, 1-methylallyloxy, 2-pentenyloxy and 2-hexenyloxy groups and the like.

The term "a lower alkanoyl-lower alkoxy group" means a straight or branched alkanoylalkoxy group in which the alkoxy moiety is a straight or branched alkoxy group having 1 to 6 carbon atoms and the alkanoyl moiety is a straight or branched alkanoyl group having 1 to 6 carbon atoms, and the examples including, formylmethoxy, 2-acetylethoxy, 1-propionylethoxy, 3-butyrylpropoxy, acetylmethoxy, 4-isobutyrylbutoxy, 1,1-dimethyl-2-pentanoylethoxy, 5-hexanoylpentyloxy, 6-acetylhexyloxy and 2-methyl-3-propionylpropoxy groups and the like.

The term "a lower alkylaminocarbonyl-lower alkoxy group" means a straight or branched alkoxy group having 1 to 6 carbon atoms, having 1 to 2 straight or branched alkyl group having 1 to 6 carbon atoms as the substituents, and the examples including, methylaminocarbonylmethoxy, ethylaminocarbonylemthoxy, propylaminocarbonylmethoxy, isopropylaminocarbonylmethoxy, butylaminocarbonylemthoxy, tert-butylaminocarbonylmethoxy, pentylaminocarbonylmethoxy, hexylaminocarbonylmethoxy, dimethylaminocarbonylmethoxy, diethylaminocarbonylmethoxy, dipropentylaminocarbonylmethoxy, dibutylaminocarbonylmethoxy, dipentylaminocarbonylmethoxy, dihexylaminocarbonylemthoxy, N-methyl-N-ethylaminocarbonylmethoxy, N-ethyl-N-propylaminocarbonylmethoxy, N-methyl-N-butylaminocarbonylmethoxy, N-methyl-N-hexylaminocarbonylmethoxy, 2-methylaminocarbonylethoxy, 1-ethylaminocarbonylmethoxy, 3-propylaminocarbonylpropoxy, 4-butylaminocarbonylbutoxy, 1,1-dimethyl-2-pentylaminocarbonylethoxy, 5-hexylaminocarbonylpentyloxy, 6-dimethylaminocarbonylhexyloxy, 2-diethylaminocarbonylethoxy, 1-(N-methyl-N-hexylamino)carbonylethoxy, 3-dihexylaminocarbonylaminopropoxy, 4-dibutylaminocarbonylbutoxy and 2-(N-methyl-N-pentylamino)carbonylethoxy groups and the like.

The term "a phenoxy-lower alkyl group which may have a lower alkyl groups as the substituents on the phenyl ring" means a phenoxyalkyl group in which the alkyl moiety is a straight or branched alkyl group having 1 to 6 carbon atoms which may have 1 to 3 straight or branched alkyl groups having 1 to 6 carbon atoms as the substituents on the phenyl ring, and the examples including, phenoxymethyl, 2-phenoxyethyl, 1-phenoxyethyl, 3-phenoxypropyl, 4-phenoxybutyl, 1,1-dimethyl-2-phenoxyethyl, 5-phenoxypentyl, 6-phenoxyhexyl, 2-methyl-3-phenoxypropyl, 2-(3-methylphenoxy)ethyl, 3-(2-ethylphenoxy)propyl, 4-(3-ethylphenoxy)butyl, 1,1-dimethyl-2-(4-ethylphenoxy)ethyl, 5-(4-isopropylphenoxy)pentyl, 6-(4 hexylphenoxy)hexyl, 3,4-dimethylphenoxymethyl, 3,4,5-trimethylphenoxymethyl and 2,5-dimethylphenoxymethyl groups and the like.

The term "a morpholino-lower alkyl group which may have phenyl-lower alkyl groups as the substituents on the morpholine ring" means a morpholinoalkyl group which may have phenylalkyl groups in which the alkyl moiety is a straight or branched alkyl groups having 1 to 6 carbon atoms as the substituents on the morpholine ring, and the examples including, morpholinomethyl, 2-morpholinoethyl, 1-(3-morpholino)ethyl, 3-(2-morpholino)propyl, 4-morpholinobutyl, 5-(2-morpholino)pentyl, 6-(3-morpholino)hexyl, 2,2-dimethyl-3-morpholinopropyl, 2-methyl-3-morpholinopropyl, (1-benzyl-3-morpholino)methyl, 2-[1-(2-phenylethyl)-2-morpholino]ethyl, 1-[2-(1-phenylethyl)morpholino]ethyl, 4-[3-(3-phenylpropyl)morpholino]butyl, 5-[1-(1,1-dimethyl-2-phenylethyl)-2-morpholino]pentyl, 6-[1-(5-phenylpentyl)-3-morpholino)]hexyl, 2,2-dimethyl-3-[1-(2-methyl-3-phenylpropyl)-3-morpholino]propyl and 2-methyl-3-(1-benzyl-3-morpholino)propyl groups and the like.

The term "a piperidinyl group which may have phenyl-lower alkyl groups as the substituents on the piperidine ring" means a piperidinyl group which may have phenylalkyl groups in which the alkyl moiety is a straight or branched alkyl group having 1 to 6 carbon atoms as the substituents on the piperidine ring, and the examples including, 1-benzyl-4-piperidinyl, 1-(2-phenylethyl)-4-piperidinyl, 1-(1-phenylethyl)-4-piperidinyl, 3-(3-phenylpropyl)-1-piperidinyl, 2-(1,1-dimethyl-2-phenylethyl)-1-piperidinyl, 4-(5-phenylpentyl)-1-piperidinyl, 1-(2-methyl-3-phenylpropyl)-2-piperidinyl, 1-(6-phenylpentyl)-3-piperidinyl, 1-benzyl-2-piperidinyl, 1-(2-phenylethyl)-2-piperidinyl, 1-(1-phenylethyl)-2-piperidinyl, 4-(3-phenylpropyl)-1-piperidinyl, 4-(4-phenylbutyl)-1-piperidinyl, 2-(5-phenylhexyl)-3-piperidinyl and 3-methyl-2-(6-phenylhexyl)-2-piperidinyl groups and the like.

The term "a carboxy-lower alkyl group" means a carboxyalkyl group in which the alkyl moiety is a straight or branched alkyl group having 1 to 6 carbon atoms, and the examples including, carboxymethyl, 2-carboxyethyl, 1-carboxyethyl, 3-carboxypropyl, 4-carboxybutyl, 1,1-dimethyl-2-carboxyethyl, 5-carboxypentyl, 6-carboxyhexyl and 2-methyl-3-carboxypropyl groups and the like.

The term "a phenyl-lower alkoxycarbonyl-lower alkyl group" means a phenylalkoxycarbonylalkyl group in which the alkyl or alkoxy moieties are a straight or branched alkyl or alkoxy group having 1 to 6 carbon atoms, and the examples including, phenylmethoxycarbonylmethyl, 2-(2-phenylethoxycarbonyl)ethyl, 1-(1-phenylethoxycarbonyl)ethyl, 3-(3-phenylpropoxycarbonyl)propyl, 4-(4-phenylbutoxycarbonyl)butyl, 1,1-dimethyl-2-(2-phenylethoxycarbonyl)ethyl, 5-(5-phenylpentyloxycarbonyl)pentyl, 6-(6-phenylhexyloxycarbonyl)hexyl and 2-methyl-3-(3-phenylpropoxycarbonyl)propyl groups and the like.

The term "an amido-lower alkyl group which may have lower alkyl groups as the substituents" means a straight or branched alkyl group having 1 to 6 carbon atoms which may have, as the substituents, amido groups which may have 1 to 2 straight or branched alkyl groups having 1 to 6 carbon atoms as the substituents, and the examples including, amidomethyl, methylamidomethyl, 2-ethylamidoethyl, 1-propylamidoethyl, 3-isopropylamidopropyl, 4-butylamidobutyl, 1,1-dimethyl-2-tert-butylamidoethyl, 5-pentylamidopentyl, 6-hexylamidohexyl, 2-dimethylamidoethyl, diethylamidomethyl, 1-dipropylamidoethyl, 3-dibutylamidopropyl, 4-dipentylamidobutyl, 5-dihexylamidopentyl, 6-(N-methyl-N-ethylamido)hexyl, (N-ethyl-N-propylamido)methyl, 2-(N-methyl-N-butylamido)ethyl and 3-(N-methyl-N-hexylamido)propyl groups and the like.

The term "a 5-or 6-membered saturated heterocyclic group-substituted carbonyl-lower alkyl group" means a 5-or 6-membered saturated heterocyclic group-substituted carbonylalkyl group in which the alkyl moiety is a straight or branched alkyl group having 1 to 6 carbon atoms, and the examples including, (1-pyrrolidinylcarbonyl)methyl, 2-(1-piperidinylcarbonyl)ethyl, 1-(1-piperazinylcarbonyl)ethyl, 3-morpholinocarbonylpropyl, 4-thiomorpholinocarbonylbutyl, 1,1-dimethyl-2-(1-pyrrolidinylcarbonyl)ethyl, 5-(1-piperidinylcarbonyl)pentyl, 6-morpholinocarbonylpentyl and 2-methyl-3-thiomorpholinocarbonylpropyl groups and the like.

The term "a piperidinyl group which may have lower alkyl groups as the substituents on the piperidine ring" means a piperidinyl group which may have straight or branched alkyl groups having 1 to 6 carbon atoms as the substituents, and the examples including, piperidinyl, 1-methyl-2-piperidinyl, 1-ethyl-2-piperidinyl, 1-propyl-2-piperidinyl, 4-butyl-1-piperidinyl, 4-pentyl-1-piperidinyl, 2-hexyl-3-piperidinyl and 3-methyl-2-piperidinyl groups and the like.

The term "a quinuclidinyl group which may have as the substituents amino groups having or without having lower alkyl groups as the substituents" means a quinuclidinyl group which may have as the substituents amino groups having or without having 1 to 2 straight or branched alkyl groups having 1 to 6 carbon atoms as the substituents, and the examples including, guinuclidinyl, 3-amino-1-quinuclidinyl, 3-methylamino-1-quinuclidinyl, 3-ethylamino-1-quinuclidinyl, 2-propylamino-1-quinuclidinyl, 2-butylamino-1-quinuclidinyl, 3-butylamino-1-quinuclidinyl, 2-(1,1-dimethyl-2-tert-butylamino)-1-quinuclidinyl, 3-(5-pentylamino)-1-quinuclidinyl, 2-(6-hexylamino)-1-quinuclidinyl, 3-dimethylamino-1-quinuclidinyl, 2-diethylamino-1-quinuclidinyl, 3-dipropylamino-1-quinuclidinyl, 2-dihexylamino-1-quinuclidinyl and 3-(N-methyl-N-ethylamino)-1-quinuclidinyl groups and the like.

Carbonstyril derivatives represented by the general formula (1) contain some of known compounds, and can be prepared by various processes. Examples of processes including as follows.

Reaction process formula - 1

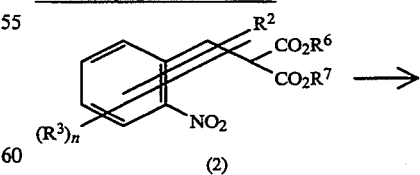

(2)

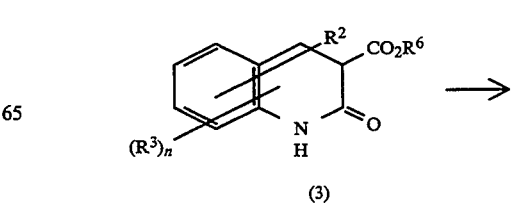

(3)

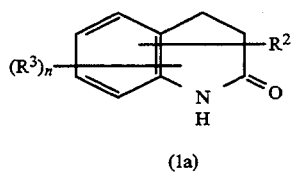

(1a)

wherein $R^2$, $R^3$, n and the carbon-carbon bond between 3- and 4- positions in the carbostyril skeleton are the same as previously; $R^6$ and $R^7$ are each a lower alkyl group.

The cyclization reaction of a compound of the general formula (2) can be carried out, for example, method-(i) by reducing it in a suitable solvent by using a catalytic reducing catalyst, or method-(ii) by reducing it in an inert solvent by using a mixture of a metal or metal salt with an acid, or a metal or metal salt with an alkali metal hydroxide, a sulfide, an ammonium salt and the like.

In carrying out the above-mentioned method-(i), examples of the solvent used in this reduction including, water, acetic acid, alcohols such as methanol, ethanol, isopropanol and the like, hydrocarbons such as hexane, cyclohexane and the like, ethers such as diethylene glycol dimethyl ether, dioxane, tetrahydrofuran, diethyl ether and the like, esters such as ethyl acetate, methyl acetate and the like, aprotic polar solvents such as N,N-dimethylformamide and the like. Examples of the catalytic reduciton catalysts used in this reaction including, palladium, palladium black, palladium-carbon, platinum, platinum oxide, cupper chromite, Raney nickel and the like. The amount of the catalyst used in this reaction may be 0.02 to equivalent part by weight of the catalyst to one part by weight of a compound of the general formula (2). The reaction can be carried out generally at about 50° to 150 ° C., preferably, at about 50° to 100° C., under 1 to 10 atmospheric pressure of hydrogen, and completes in about 0.5 to 10 hours, In case of carrying out the above-mentioned method-(ii), a mixture of iron, zinc, tin or stannous chloride with a mineral acid such as hydrochloric acid or sulfuric acid, a mixture of iron, ferrous sulfate, zinc or tin with an alkali metal hydroxide, a mixture of sulfide such as ammonium sulfide or the like with an aqueous ammonia, or with an ammonium salt such as ammonium chloride can be used. AS to the inert solvents used in this reaction, examples including water, acetic acid, methanol, ethanol, dioxane and the like. The reaction conditions of method-(ii) can be selected suitably depend on the type of the reducing agents. For example, in case of using a mixture of stannous chloride with hydrochloric acid, the reaction can be carried out preferably at about 0° to 150° C., for 0.5 to 10 hours.

The amount of the reducing agent is used at least an equimolar quantity to 5 times the molar quantities thereof per molar quantity of a compound of the general formula (2).

The reaction for introducing a compound of the general formula (3) to a compound of the general formula (1a) can be carried out in the presence of an acid in the absence or presence of a suitable solvent. As the acid used in this reaction can be exemplified mineral acids such as hydrochloric acid, hydrobromic acid and sulfuric acid and the like, organic acids such as p-toluenesulfonic acid and the like. The amount of the acid used in the reaction may be generally at least an equimolar quantity, preferably an excess amount of the acid may used to a molar quantity of a compound of the general formula (3). As to the solvent used in this reaction, the examples including, water, alcohols such as methanol, ethanol, isopropanol and the like, aromatic hydrocarbons such as benzene, toluene, xylene, tetrahydronaphthalene and the like, ethers such as diethyl ether, dioxane, tetrahydrofuran diethylene glycol dimethyl ether, diethylene glycol monomethyl ether and the like, polar solvents such as dimethylformamide, dimethyl sulfoxide, hexamethylphosphoric triamide and the like. The reaction can be generally be carried out at about room temperature to 200° C., preferably at about room temperature to 150° C., and completes in about 1 to 10 hours.

Reaction process formula - 2

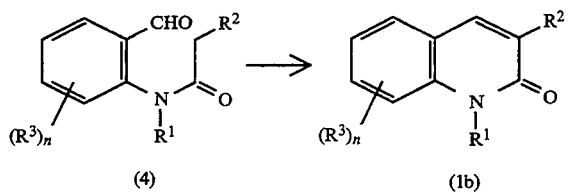

(4) (1b)

wherein $R^1$, $R^2$, $R^3$, n and the carbon-carbon bond between 3- and 4-positions in the carbostyril skeleton are the same as defined prevously.

The cyclization reaction of a compound of the general formula (4) can be carried out in the presence of a suitable basic compound in a suitable solvent. As to the basic compound used in this reaction, the examples including inorganic basic substances such as potassium carbonate, sodium carbonate, sodium acetate, potassium acetate, sodium hydroxide, sodium hydrogen carbonate, sodium metal, potassium metal, sidium amide, sodium hydride and the like, alcoholates such as sodium ethylate, sodium methylate and the like, organic basic compounds such as triethylamine, tripropylamine, pyrrolidine, piperidine, pyridine and the like. The amount of the basic substances used in this reaction may be generally at least an equimolar quantity, preferably 1 to 2 times the molar quantities of the basic substance may be used to a molar quantity of compound of the general formula (4). As to the solvents used to this reaction, the examples including, aromatic hydrocarbons such as benzene, toluene, xylene and the like, alcohols such as methanol, ethanol, isopropanol and the like, ethers such as diethyl ether, dioxane, tetrahydrofuran, ethylene glycol dimethyl ether and the like, polar solvents such as N-methylpyrrolidone, dimethylformamide, dimethyl sulfoxide, hexamethylphosphoric triamide, acetic anhydride and the like. The above-mentioned reaction can be carried out generally at about room temperature to 150° C., preferably at about room temperature to 100° C., and generally completes in about 1 to 10 hours.

Reaction process formula - 3

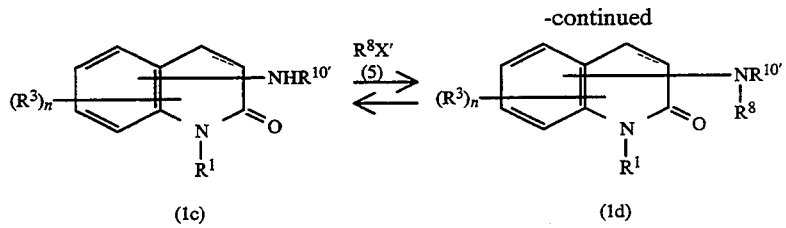

wherein $R^1$, $R^3$, n and the carbon-carbon bond between 3- and 4-positions in the carbostyril skeleton are the same as defined above; $R^8$ is a phenyl-lower alkanoyl group, a lower alkanoyl group which may have halogen atoms or lower alkylamino groups as the substituents, a piperidinyl-lower alkanoyl group which may have penyl-lower alkyl groups as the substituents on the piperidine ring, or pyrrolidinyl-lower akkanoyl group; $X'$ is a hydroxy group; and $R^{10'}$ is a hydrogen atom, a lower alkyl group which may have hydroxy groups or lower alkyl groups as the substituents, a phenyl-lower alkyl group which may have lower alkoxy groups as the substituents on the phenyl ring, a phenyl group, a lower alkenyl group, a cycloalkyl group, an imidazolyl group a phenoxy-lower alkyl group which may have lower alkyl groups as the substituents, a morpholino-lower alkyl group which may have phenyl-lower alkyl groups as the substituents on the morpholine ring, or a piperidinyl group which may have phenyl-lower alkyl groups as the substituents on the piperidine ring.

The reaction of a compound of the general formula (1c) with compound of the general formula (5) can be carried out under reaction conditions of usual amidobond formation reaction, for example, (a) mixed acid anhydride method: by reacting a carboxylic acid (5) with an alkylhalocarboxylic acid to form the corresponding mixed acid anhydride, then reacting said mixed acid anhydride with an amine (1c); (b) activated ester method: by converting a carboxylic acid (5) into the corresponding activated ester thereof, such as p-nitrophenyl ester, N-hydroxysuccinimide ester, 1-hydroxybenzotriazol ether or the like, then reacting said activated ester carboxylic acid with an amine (1c); (c) carbodiimide method: by condensing a carboxylic acid (5) with an amine (1c) in the presence of an activating agent such as dicyclohexylcarbodiimide, carbonyldiimidazol or the like; (d) other method: by reacting a carboxylic acid (5) with a dehydrating agent such as acetic anhydride to prepare the corresponding carboxylic anhydride, then reacting said carboxylic anhydride with an amine (1c); (e) method by reacting an ester prepared by reacting carboxylic acid (5) with a lower alcohol, with an amine (1c) under a high pressure and a high temperature; (f) method by reacting an acid halide of a carboxylic acid (5), i.e., carboxylic halid, with an amine (1c).

The mixed acid anhydride being used in the (a) mixed acid anhydride method can be obtained by a usual Schotten-Baumann reaction, and generally said mixed acid anhydride is reacted with an amine (1c), without separated from the reaction system, to prepared a compound of the general formula (1d). The Schotten-Baumann reaction is carried out in the presence of a basic compound. As to the basic compound, any basic compound used in Schotten-Baumann reaction can applied, for example organic basic compounds such as triethylamine, trimethylamine, pyridine, dimethylaniline, N-methylmorpholine, 1,5-diazabicyclo[4.3.0]none-5 (DBN), 1,8-diazabicyclo[5.4.0]undecene-7 (DBU), 1,4-diazabicyclo[2.2.2]octane (DABCO) and the like, and inorganic basic compounds such as potassium carbonate, sodium carbonate, potassium hydrogen carbonate, sodium hydrogen carbonate and the like. The reaction may be carried out generally at about $-20°$ to $100°$ C., preferably at about $0°$ to $50°$ C., for generally 5 minutes to 10 hours, preferably 5 minutes to 2 hours. The reaction of thus obtained mixed acid anhydride with an amine (1c) may be carried out generally at about $-20°$ to $150°$ C., preferably at about $10°$ to $50°$ C., for about generally 5 minutes to 10 hours, preferably 5 minutes to 5 hours. The mixed acid anhydride method is generally carried out in a solvent. As to the solvent used in this reaction, any conventional solvent used in mixed acid anhydride method can be applied, and specifically, halogenated hydrocarbons such as methylene chloride, chloroform, dichloroethane and the like, aromatic hydrocarbons such as benzene, toluene, xylene and the like, ethers such as diethyl ether, tetrahydrofuran, dimethoxyethane and the like, esters such as methyl acetate, ethyl acetate and the like, oprotic polar solvents such as N,N-dimethylformamide, dimethyl sulfoxide, hexamethylphosphoric triamide and the like can be exemplified. As to an alkylhalocarboxylic acid used in the mixed acid anhydride method, there can be exemplified methyl chloroformate, methyl bromoformate, ethyl chloroformate, ethyl bromoformate, isobutyl chloroformate and the like. In carrying out the method, the ratio of amount of a carboxylic acid (5) to an alkylhalocarboxylic acid and an amine (1c) is generally an equimolar quantity each of these materials, and 1 to 1.5 times the molar quantity each of the alkylhalocarboxylic acid and carboxylic acid (5) may be used to an amine (1c).

In case of carrying out the method of reacting a carboxylic acid halide with an amine (1c), said reaction is carried out in the presence of a basic compound. As to the basic compounds, any known basic compound can be selected from a wide range, for example, other than the basic compounds to be used in Schotten-Baumann reaction as metnioned-above, there can be exemplified sodium hydroxide, potassium hydroxide, sodium hydride, potassium hydride, silver carbonate, alcoholates such as sodium methylate, sodium ethylate and the like. As to the solvent used in this reaction, other than solvents used in the above-mentioned mixed acid anhydride method, there can be exemplified alcohols such as methanol, ethanol, propanol, butanol, 3-methoxy-1-butanol, ethyl cellosolve, methyl cellosolve and the like, pyridine, acetone, acetonitrile and the like, and mixtures of these solvents. The ratio of the amount of an amine (1c) to the amount of carboxylic acid halide is not specifically restricted and can be selected from a wide range. Generally, at least an equimolar quantity, preferably 1 to 5 times the molar quantities of the latter may be used to the former. The reaction is generally carried out at about $-30°$ to $180°$ C., preferably $0°$ to $150°$ C., and complets in about 5 minutes to 30 hours.

In the above-mentioned Reaction process formula −3, the reaction introducing a compound of the general formula (1d) to a compound of the general formula (1c) is carried out in the presence of a mineral acid such as hydrochloric acid, sulfuric acid, hydrobromic acid and the like, or an organic acid such as p-toluenesulfonic acid and the like, and in a solent such as water, an alcohol such as methanol, ethanol, isopropanol and the like. The reaction is generally carried out at about room temperture to 200° C., preferably at about room temperature to 150° C., and complets generally in 30 minutes to 10 hours.

In case of using a compound of the general formula (1d) wherein $R^8$ is a halogen-substituted lower alkanoyl group, a compound of the general formula (1d) in which $R^8$ is a lower alkylamino-lower alkanoyl group, a piperidinyl-lower alkanoyl group which may have phenyl-lower alkyl groups as the substituents on the piperidine ring or a pyrrolidinyl-lower alkanoyl group can be obtained by reacting a compound of the general formula (1d) with an amine (i.e., a lower alkylamine a piperidine which may have phenyl-lower alkyl groups as the substituents on the piperidine ring or a pyrrolidine). The reaction is generally carried out in a suitable inert solvent and in the presence of or absence of a basic condensing agent. As to the solvent used in this reaction, there can be exemplified aromatic hydrocarbons such as benzene, toluene, xylene and the like, alcohols such as methanol, ethanol, isopropanol and the like, acetic acid, ethyl acetate, dimethylformamide, dimethylsulfoxide, hexamethylphosphoric triamide and the like. Further, as to the basic condensing agent used in the reaction, carbonates such as sodium carbonate, potassium carbonate, sodium hydrogen carbonate, potassium hydrogen carbonate and the like, metal hydroxide such as sodium hydroxide, potassium hydroxide and the like, metal alcoholates such as sodium ethylate, sodium methylate and the like, organic basic compounds such as pyridine, triethylamine and the like can be exemplified. The amount of an amine may be generally at least an equimolar quantity, preferably 1 to 10 times the molar quantities to an amine (1d). The reaction is generally carried out at about 40° to 150° C., preferably at 50° to 120° C., and completes in generally about 5 to 30 hours.

Reaction process formula-4

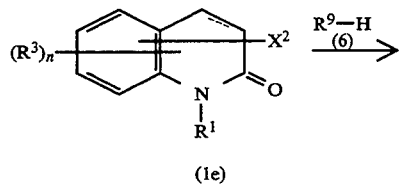

(1e)

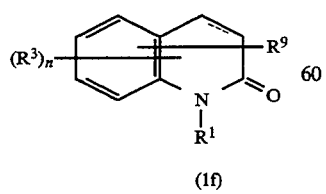

(1f)

wherein $R^1$, $R^3$, n and the carbon-carbon bond between 3- and 4-positions in the carbostyril skeleton are the same as defined above; $R^9$ is a group of the formula

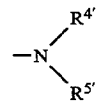

(wherein $R^{4'}$ and $R^{5'}$ are each the same or different, and are each a hydrogen atom, a lower alkyl group which may have hydroxy groups, amino groups or lower-alkylamino groups as the substituents, a phenyl-lower alkyl group which may have lower alkoxy groups as the substituents, a phenyl group, a lower alkenyl group, an imidazolynyl group, a phenoxy-lower alkyl group which may have lower alkyl groups as the substituents, a morpholino-lower alkyl group which may have a phenyl-lower alkyl groups as the substituents on the morpholine ring, a piperidinyl group which may have phenyl-lower alkyl groups as the substituents on the piperidine ring, or a cycloalkyl group; further these $R^{4'}$ and $R^{5'}$ as well as the adjacent nitrogen atom being bonded thereto, together with or without other nitrogen atom, oxygen atom or sulfur atom may form a 5- to 9-membered heterocyclic group; said 5- to 9-membered heterocyclic group may have 1 to 3 substituents selected from the group consisting of a phenyl group, a hydroxy group, a phenyl-lower alkyl group which may have lower akoxy groups as the substituents, a $C_1$-$C_{10}$ alkyl group which may have 1 to 3 hydroxy groups, lower alkoxy groups or halogen atoms as the substituents, a lower alkenyl group, a lower alkoxycarbonyl-lower alkyl group, tetrahydrofuryl-lower alkyl group, thienyl-lower alkyl group, a cycloalkyl-lower alkyl group, cycloalkyl group, a benzoyl-lower alkyl group which may have halogen atoms on the phenyl ring, a pyridyl-lower alkyl group, a lower alkylamido group, a lower alkynyl group, a lower alkanoyl-lower alkyl group, a phenyl-lower alkoxycarbonyl group, a group of the formula

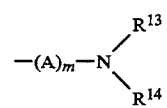

((wherein $R^{13}$ and $R^{14}$ are each the same or different, and is a lower alkyl group, a phenyl-lower alkyl group which may have lower alkoxy groups as the substituents on the phenyl ring; further $R^{13}$ and $R^{14}$ as well as the adjacent nitrogen atom being bonded thereto, together with or without other nitrogen atom or oxygen atom may form a 5- or 6-membered heterocyclic group; said heterocyclic group may have lower alkyl groups as the substituents; A is a lower alkylene group or a group of the formula

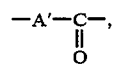

wherein A' is a lower alkylene group; m is 0 or 1)), and a benzoyl group which may have lower alkoxy groups as the substituents on the phenyl ring); and $X^2$ is a halogen atom.

The reaction of a compound of the general formula (1e) with a compound of the general formula (6) is carried out in a suitable solvent, in the presence or absence of a bacid compound. As to the solvent used in this reaction, N-methylpyrrolidone, and any solvents used in the reaction of a carboxylic acid halide with a compound (5) in the above-mentioned Reaction process formula -3 can also be used. As to the basic compound used in this reaction, similar to the solvents, any basic compounds used in the reaction of carboxylic acid halide with a compound (5) in the above-mentioned Reaction process formula—3 can also be used. This reaction is advantageously proceeded by adding a copper halide such as copper iodide or copper powder in the reaction system. The reaction is generally carried out at about room temperature to 250° C., preferably at about room temperature to 200° C., and generally completes in about 5 to 20 hours.

the like. The reaction can be advantageously proceeded by adding an alkali metal iodide such as potassium iodide, sodium iodide and the like as the reaction accelerator. Further, the said reaction can be carried out by adding a copper halide such as copper iodide or copper powder to the reaction system. The ratio of the about of compound (1c) to the amount of compound (7) is generally an equimolar quantity to an excess quantity, preferably 1 to 5 times the molar quantities of the latter to the former The reaction is generally carried out at about room temperature to 200° C., preferably at about 60° to 120° C., and completes in about several hours to 30 hours.

Reaction process formula - 5

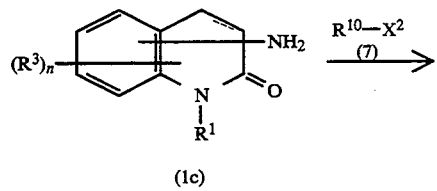

(1c)

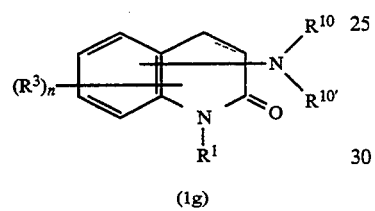

(1g)

wherein $R^1$, $R^3$, n, $X^2$ and the carbon-carbon bond between 3- and 4-positions in the carbostyril skeleton are the same as defined above; $R^{10}$ is a lower alkyl group which may have hydroxy groups or lower alkyl groups as the substituents, a phenyl-lower alkyl group which may have lower alkoxy groups as the substituents, a phenyl group, a lower alkenyl group, a cycloalkyl group, an imidazolynyl group, a phenoxy-lower alkyl group which may have lower alkyl groups as the substituents, a morpholino-lower alkyl group which may have phenyl-lower alkyl groups as the substituents on the morpholine ring, or a piperidinyl group which may have phenyl-lower alkyl groups as the substituents on the piperidine ring; and $R^{10'}$ is the same as defined in $R^{10}$ or a hydrogen atom.

The reaction of a compound of the general formula (1c) with a compound of the general formula (7) is carried out in the absence or presence of a common inert solvent. As to the solvent, there may be exemplified ethers such as dioxane, tetrahydrofuran, ethylene glycol dimethyl ether and the like, aromatic hydrocarbons such as benzene, toluene, xylene and the like, lower alcohols such as methanol, ethanol, isopropanol and the like, polar solvent such as acetic acid, ethyl acetate, dimethylformamide, dimethyl sulfoxide, acetone, acetonitrile, N-methylpyrrolidone, hexamethylphosphoric triamide and the like. The above-mentioned reaction is carried out advantageously by using a basic compound as the deacidifying agent. As to the basic compounds, there can be exemplified inorganic basic compounds such as potassium carbonate, sodium carbonate, sodium hydroxide, sodium hydrogen carbonate, sodium amide, sodium hydride and the like, metal alcoholates such as sodium methylate, sodium ethylate adn the like, organic basic compounds such as DBU, triethylamine, tripropylamine, pyridine, quinoline and Reaction process formula - 6

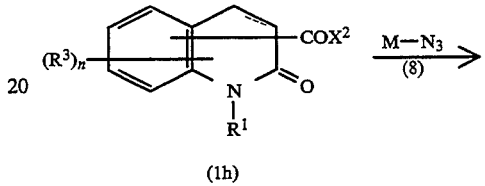

(1h)

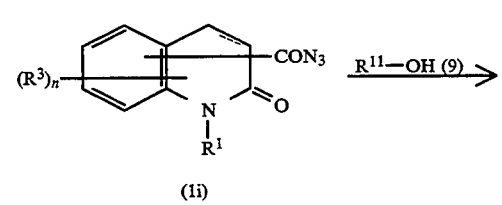

(1i)

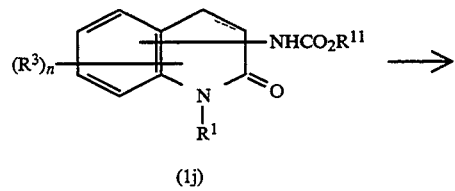

(1j)

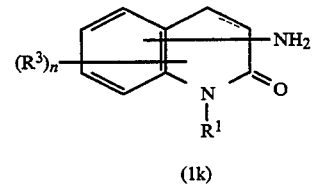

(1k)

where in $R^1$, $R^3$, n, $X^2$ and the carbon-carbon bond between 3- and 4-positions in the carbostyril skeleton are the same as defined above; $R^{11}$ is a lower alkyl group; and M is an alkali metal such as sodium, potassium and the like.

The reaction of a compound of the general formula (1h) with a compound of the general formula (8) is carried out in a suitable solvent and in the absence or presence of a basic compound. As to the solvent used in the reaction, halogenated hydrocarbons such as methylene chloride, chloroform, and the like, aromatic hydrocarbons such as benzene, toluene, xylene and the like, ethers such as diethyl ether, tetrahydrofuran, dimethoxyethane and the like, esters such as methyl acetate, ethyl acetate and the like, aprotic polar solvents such as N,N-dimethylformamide, dimethyl sulfoxide, hexamethylphosphoric triamide and the like, alcohols such as methanol, ethanol, propanol, butanol, 3-methoxy-1-butanol, ethyl cellosolve, methyl cello solve and the like, pyridine, acetone, acetonitrile, water and the like, and mixtures of these solvents can be exemplified. As to the basic compound used in the reaction, organic basic compounds such as triethylamine, trimethylamine, pyridine, dimethylamine, N-methylmorpholine, DBN, DBU, DABCO and the like, inorganic basic compounds, such as potassium carbonate, sodium carbonate, potassium hydrogen carbonate, sodium hydrogen carbonate, potassium hydroxide, sodium hydroxide, potassium hydride, sodium hydride, silver carbonate, alcoholates such as sodium methylate, sodium ethylate and the like can be exemplified. The amount of compound (8) may be generally at least about an equimolar quantity, preferably about 1 to 1.5 times the molar quantity thereof to a compound (1h). The reaction is generally carried out at about $-30°$ to $180°$ C., preferably at about $0°$ to $150°$ C., and generally complets in 5 minutes to 30 hours. The reaction of a compound of the general formula (1i) with a compound of the general formula (9) is carried out in a suitable solvent and in the presence or absence of a suitable solvent, at about $0°$ to $150°$ C., preferably at about room temperature to $100°$ C. As to the solvent used in this reaction, any solvents used in the reaction of compound (1h) with compound (8) can also be used. The amount of compound (9) may be a large excess quantity to compound (1i), and the reaction is generally completes in 1 to 5 hours.

The reaction for introducing a compound of the general formula (1j) to a compound of the general formula (1k) can be carried out under the conditions similar to those employed in the reaction of a compound the general formula (3) to a compound of the general formula (1a).

Reaction process formula - 7

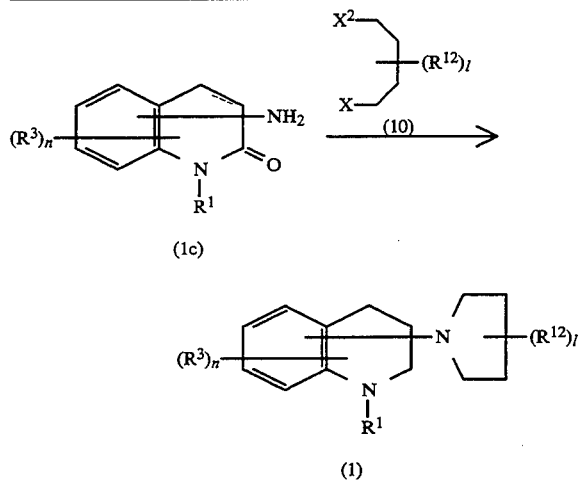

wherein $R^1$, $R^3$, n, $X^2$ and the carbon-carbon bond between 3- and 4-positions in the carboxtyril skeleton are the same as defined above; $R^{12}$ is a phenyl group, a hydroxy group, a phenyl-lower alkyl group which may have lower alkoxy groups as the substituents on the phenyl ring, a $C_1$-$C_{10}$ alkyl group which may have 1 to 3 hydroxy groups, lower alkoxy groups or halogen atoms as the substituents, a lower alkenyl group, a lower alkoxycarbonyl-lower alkyl group, a tetrahydrofuryl-lower alkyl group, a thienyl-lower alkyl group, a cycloalkyl-lower alkyl group, a cycloalkyl group, a benzoyl-lower alkyl group which may have halogen atoms as the substituents on the phenyl ring, a pyridyl-lower alkyl group, a lower alkylamido group, a lower alkynyl group, a lower alkanoyl-lower alkyl group, a phenyl-lower alkoxycarbonyl group, a group of the formula

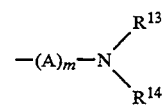

((wherein $R^{13}$ and $R^{14}$ are each the same or different, and is a lower alkyl group, a phenyl-lower alkyl group which may have lower alkoxy groups as the substituents on the phenyl ring; further $R^{13}$ and $R^{14}$ as well as the adjacent nitrogen atom being bonded thereto, together with or without other nitrogen atom or oxygen atom may form a 5- or 6-membered heterocyclic group; said heterocyclic group may have lower alkyl groups as the substituent; A is a lower alkylene group or a group of the formula

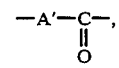

wherein A' is a lower alkylene group; m is 0 or 1)), and a benzoyl group which may have lower alkoxy groups as the substituents on the phenyl ring); l is 0 or an integer of 1 to 3; $X^3$ is a halogen atom.

The reaction of a compound of the general formula (1c) with a compound of the general formula (10) can be carried out under conditions similar to those described in the above-mentioned reaction of a compound of the general formula (1c) with a compound of the general formula (7).

Reaction process formula - 8

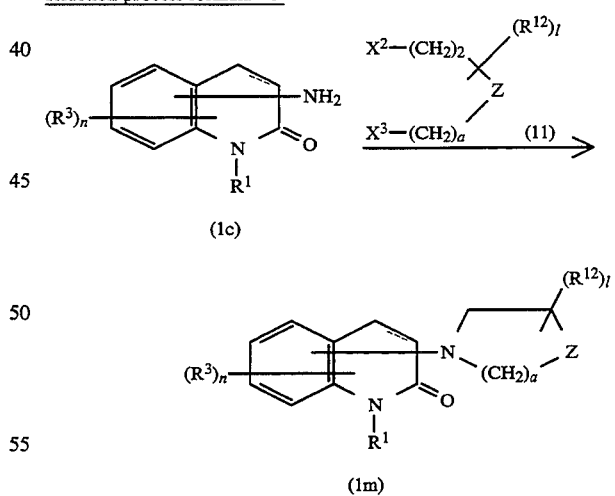

wherein $R^1$, $R^3$, $R^{12}$, l, n, $X^2$, $X^3$ and the carbon-carbon bond between 3- and 4-positions in the carbostyril skeleton are the same as defined above; Z is a methine group, a nitrogen atom, an oxygen atom or a sulfur atom; a is 2 or 3.

The reaction of a compound of the general formula (1c) with a compound of the general formula (11) can be carried out under conditions similar to those applied in the reaction of a compound of the general formula (1c) with a compound of the general formula (7).

Among the compounds of the general formula (1m) thus obtained from the above-mentioned reaction, a compound in which Z is a nitrogen atom and l is 0 can be reacted with a compound of the general formula $R^{12'}$-$X^2$ (wherein $R^{12'}$ is a phenyl group a phenyl-lower alkyl group which may have lower alkoxy groups as the substituents on the phenyl ring, a $C_1$-$C_{10}$ alkyl group which may have 1 to 3 hydroxy groups or halogen atom as the substituents, a lower alkenyl group, a lower alkoxycarbonyl-lower alkyl group, a thienyl-lower alkyl group, a cycloalkyl-lower alkyl group, a cycloalkyl group, a benzoyl-lower alkyl group which may have halogen atoms as the substituents on the phenyl ring, a pyridyl-lower alkyl group, a lower alkynyl group, a lower alkanoyl-lower alkyl group, or a group of the formula

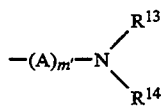

((wherein $R^{13}$, $R^{14}$ and A are the same as defined above; and m' is 1)); $X^2$ is the same as defined above) to obtain a compound of the general formula (1m) in which Z is a nitrogen atom and a group represented by the symbol $R^{12'}$ is substituted on said nitrogen atom.

This reaction can be carried out under conditions similar to those employed in the reaction of a compound (1c) with a compound (7) in the above-mentioned Reaction process formula—5.

Further, among the compounds of the general formula (1m), a compound in which Z is a nitrogen atom and l is 0 can be reacted with a compound of the general formula $R^{12''}$-$X^1$ (wherein $R^{12''}$ is a benzoyl group which may have a lower alkoxy groups as the substituents on the phenyl ring, a lower alkylamido group or a phenyl lower alkoxycarbonyl group; $X^1$ is the same as defined above) to obtain a compound of the general formula (1m) in which Z is a nitrogen atom and at the same time a group represented by the symbol $R^{12''}$ is substituted on said nitrogen atom. This reaction can be carried out under conditions similar to those employed in the reaction of a compound (1c) with a compound (5) in the above-mentioned Reaction process formula—3.

Among compounds represented by the general formula (1), a compound in which $R^2$ is a group of the formula

(wherein $R^4$ and $R^5$ are each the same or different, and are each a phenyl-lower alkanoyl group, a lower alkanoyl group which may have lower alkylamino groups as the substituents) or a compound in which $R^2$ is a group of the formula

(wherein $R^4$ and $R^5$ as well as the adjacent nitrogen atom being bonded thereto form a heterocyclic group, and said heterocyclic group having lower alkylamido groups or a group of the formula

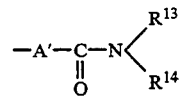

((wherein A', $R^{13}$ and $R^{14}$ are the same as defined above)), or the nitrogen atom of said heterocyclic group is substituted with benzoyl groups which may have lower alkoxy groups as the substituents on the phenyl ring), can be reduced to obtain a compound in which the carbonyl group in the substitutes is covered into a —$CH_2$— group.

Said reducing reaction is carried out in a suitable solvent in the presence of a hydrogenating reducing agent. As to the hydrogenating reducing agent, sodium boron hydride, lithium aluminum hydride, diborane and the like can be exemplified. The amount of the hydrogenating reducing agent may be at least an equimolar quantity, perferably 1 to 3 times the molar quantities to the starting material can be used. In the case of using lithium aluminum hydride as the reducing agent, it can be used preferably an equivalent weight to the starting material. As to the solvent used in the reducing reaction, water, lower alcohols such as methanol, ethanol, isopropanol and the like, ethers such as tetrahydrofuran, diethyl ether, diethylene glycol dimethyl ether and the like can be exemplified. The reaction is generally carried out at about —60° to 50° C., preferably at about —30° C. to room temperature, and completes in about 10 minutes to 5 hours. In the case of using lithium aluminum hydride or diborane as the reducing agent, an anhydrous solvent such as diethyl ether, tetrahydrofuran, diethylene glycol dimethyl ether and the like can be used.

Reaction process formula - 9

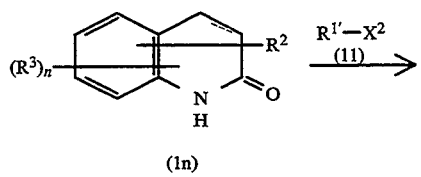

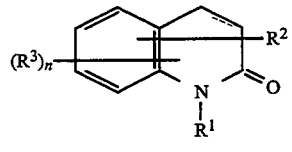

wherein $R^2$, $R^3$, n, $X^2$ and the carbon-carbon bond between 3- and 4-positions in the carbostyril skeleton are the same as defined above; and $R^{1'}$ is a lower alkyl group, a lower alkenyl group, a lower alkynyl group, a phenyl-lower alkyl group, a carboxy-lower alkyl group, a phenyl-lower alkoxycarbonyl-lower alkyl group, an amido-lower alkyl group which may have lower alkyl groups as the substituents, or 5- or 6-membered saturated heterocyclic group-substituted carbony-lower alkyl group.

The reaction of a compound of the general formula (1n) with a compound of the general formula (11) may be carried out in the presence of a basic substance, and in a suitable solvent. As to the basic substance, sodium hydride, potassium metal, sodium metal, sodium amide, potassium amide and the like can be exemplified. As to the solvent, ethers such as dioxane, diethylene glycol dimethyl ether and the like, aromatic hydrocarbons such as toluene, xylene and the like, dimethyl sulfoxide, dimethylformamide, hexamethylphosphoric triamide and the like can be exemplified.

The ratio of the amounts of a compound (1n) and a compound (11) is not specifically restricted, and can be selected from a wide range, and generally at least an equimolar quantity, preferably 1 to 2 times the molar quantities of the latter may be used to the former. The reaction is generally carried out at about 0° to 70 C., preferably at 0° C. to room temperature and generally completes in about 0.5 to 12 hours.

methoxyethanol, dimethoxymethane and the like, aromatic hydrocarbons such as benzene, toluene, xylene, cumene and the like, halogenated hydrocarbons such as dichloromethane, dichloroethane, chloroform, carbon tetrachloride and the like, alcohola such as butanol, amyl aclcohol, hexanol and the like, protic polar solvents such as acetic acid and the like, aprotic polar solvents such as dimethylformamide, dimethyl sulfoxide, hexamethylphosphoric triamide and like can be exemplified. The reaction is generally carried out at about room temperature to 300° C., preferably at about room temperature to 200° C., and generally complets in about 1 to 40 hours.

Among compounds represented by the general formula (1), a compound in which $R^1$ is a hydrogen atom and the carbon-carbon bond between 3- and 4-positions in the carbostyril skeleton is a double bond can be exist Reaction process formula - 10

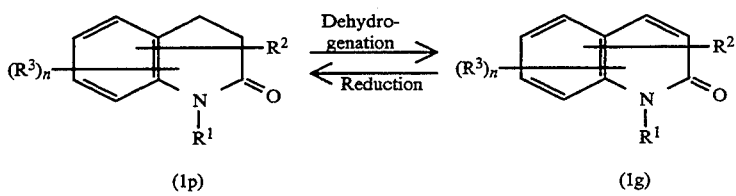

(1p)     (1g)

wherein $R^1$, $R^2$, $R^3$ and n are the same as defined above.

The reduction of a compound of the general formula lactam-lactim type tautomerism as shown in the following Reaction process formula—11.

Reaction process formula - 11

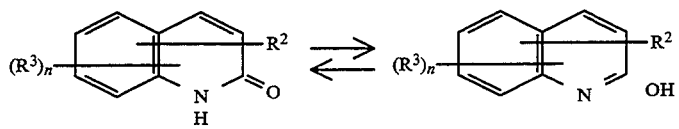

(1q) is carried out under conditions employed in a usual catalytic reduction. As to the catalyst used in this reduction, palladium, palladium-carbon, platinum, Raney-nickel and the like can be exemplified, and the catalyst may be used in a usual catalytic amount. As to the solvent used in this reduction, methanol, ethanol, isopropanol, dioxane, tetrahydrofuran, hexane, cyclohexane, ethyl acetate and the like can be exemplified. The above-mentioned reduction can be carried out either at atmospheric pressure to 20 kg/cm², preferably at an atmospheric pressure to 10 kg/cm². The reaction temperature may be generally at 0° to 150° C., preferably at room temperature to 100° C.

The dehydrogenation of a compound of the general formula (1p) is carried out in a suitable solvent by using an oxidizing agent. As to the oxidizing aget used in this reaction, benzoquinones such as 2,3-dichloro-5,6-dicyanobenzoquinone, chloranil (2,3,5,6-tetrachlorobenzoquinone) and the like, halogenating agents such as N-bromosuccinimide, N-chlorosuccinimide, bromine, and the like, hydrogenating catalysts such as selenium dioxide, palladium-carbon, palladium black, palladium oxide, Raney-nickel and the like can be exemplified. The amount of the halogenating agent is not specifically restricted, and can be selected from a wide range, and generally 1 to 5 times the molar quantity, preferably 1 to 2 times the molar quantities may be used to a compound (1p). The hydrogenating catalyst may be used in a usual catalytic amount. As to the solvent used in this reaction, ethers such as dioxane, tetrahydrofuran, wherein $R^2$, $R^3$ and n are the same as defined above.

Reaction process formula - 12

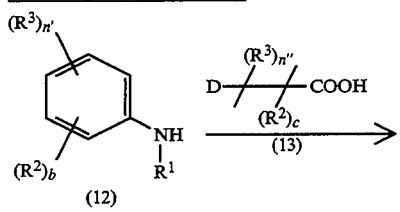

(12)

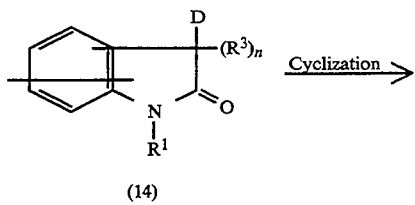

(14)

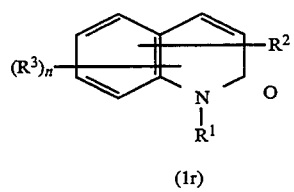

(1r)

wherein $R^1$, $R^2$ and $R^3$ are the same as defined above; n' and n" are 0, or an integer of 1 or 2; provided that they should be n'+n"=2; b and c are each 0 or 1; provided that b and c should not be 0 at the same time; D is a group of the formula $R^{15}C=CH-$ (wherein $R^{15}$ is a phenyl group, a lower alkoxy group or a halogen atom), a group of the formula

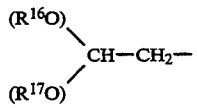

(wherein $R^{16}$ and $R^{17}$ are each a lower alkyl group) or a group of the formula $H\equiv C-$.

The reaction of a compound of the general formula (12) with a compound of the general formula (13) can be carried out under conditions similar to those employed in the reaction of a compound of the general formula (1c) with a compound of the general formula (5) in the Reaction process formula—3.

The cyclization of a compound of the general formula (14) is carried out in the presence of an acid, in the presence or absence of a suitable solvent. As to the acid used in this cyclization, it is not specifically restricted and can be selected from a wide range, specifically, inorganic acids such as hydrochloric acid, hydrobromic acid, sulfuric acid and the like, Lewis acids such as aluminum chloride, boron trifluoride, titanium tetrachloride and the like, organic acids such as formic acid, acetic acid, ethanesulfonic acid, p-toluenesulfonic acid and the like can be exemplified. Among these acids, hydrochloric acid, hydrobromic acid and sulfuric acid are preferable. The amount of the acid may be generally at least an equivalent weight, preferably 10 to 50 times weights of acid may be used to a compound of the general formula (14). As to the solvent, any common inert solvent can wide be used, for example, water, lower alcohols such as methanol, ethanol, propanol and the like, ethers such as dioxane, tetrahydrofuran and the like, aromatic hydrocarbons such as chlorobenzene, benzene, toluene and the like, halogenated hydrocarbons such as methylene chloride, chloroform, carbon tetrachloride and the like, acetone, dimethyl sulfoxide, dimethylformamide, hexamethylphosphoric triamide and the like can be exemplified. Among these solvents, water-soluble solvents such as lower alcohols ethers, acetone, dimethyl sulfoxide, dimethylformamide, hexamethylphosphoric triamide and the like are preferable. The cyclization is generally carried out at 0° to 200° C., preferably at about room temperature to 150° C., and completes generally in about 5 minutes to 6 hours.

The reaction for preparing a compound of the general formula (1r) having a group of the formula $-NHR^8$ (wherein $R^8$ is the same as defined above) can be prepared by reacting under conditions similar to those employed in the reaction of a compound (1d) with a compound (1c) in the Reaction process formula—3 to obtain a compound having $-NH_2$ as the symbol $R^2$.

Carbostyril derivatives represented by the general formula (1) according to the present invention can be easily converted into salt form thereof by reacting with a pharmaceutically acceptable basic compound. As to the basic compounds, sodium hydroxide, potassium hydroxide, calcium hydroxide, sodium carbonate, potassium hydrogen carbonate and the like can be exemplified. Furthermore, carbostyril derivative represented by the general formula (1) according to the present invention can be converted into the corresponding guaternary salt respectively by reacting with a tertiary amine form thereof or with an alkyl halide such as methyl iodide, ethyl chloride or the like.

The desired products thus obtained by various processes can be separated and purified by usual separation means. As to the separation means, solvent extraction method, dilution method, recrystallization method, column chromatography method, preparative thin layer chromatography method and the like can be exemplified.

Carbostyril derivatives of the general formula according to the present invention inevitably contain their optical isomers.

Carbostyril derivatives and salts thereof represented by the general formula (1) can be used in any form of usual pharmaceutical compositions which are prepared by using usual pharmaceutically acceptable carriers. Examples of such pharmaceutically acceptable carriers are selected depending on the desired form of pharmaceutical compositions including diluents and excipients such as fillers, diluents, binders, wetting agents, disintegrating agents, surface active agents, lubricants, etc. Pharmaceutical compositions can be selected from any desired unit form depending on the purpose of therapy, including tablets, pills, powders, liquors, suspensions, emulsions, granules, capsules, supositories, injection preparations (e.g., solutions, suspensions, etc.), etc.

For the purpose of to prepare tablet form composition, carriers which are widely used in this field can be used, for example, excipients such as lactose, sucrose, sodium chloride, glucose, urea, starch, calcium carbonate, kaolin, crystalline cellulose, silicic acid, etc; binding agents such as water, ethanol, propanol, simple syrup, glucose solutions, starch solutions, gelatin solutions, carboxymethyl cellulose, shelac, methyl cellulose, calcium phosphate, polyvinylpyrrolidone, etc.; disintegrating agents such as dried starch, sodium alginate, agar-agar powder, leuninalia powder, sodium hydrogen carbonate, calcium carbonate, esters of polyoxyethylene sorbitan fatty acids, sodium laurylsulfate, monoglyceride of stearic acid, starch, lactose, etc.; disintegration inhibitors such as sucrose, stearin, coconut butter, hydrogenated oils, etc.; absorption accelerators such as quaternary ammonium bases, sodium laurylsulfonate, etc.; wetting agents such as glycerin, starch, etc.; adsorbing agents such as starch, lactose, kaolin, bentonite, colloidal silicic acid, etc.; and lubricants such as purified talc, stearic acid salts, boric acid powder, polyethylene glycols, etc. If necessary, the tablets can further be coated with usual coating materials to make the tablets into the form of coated tablets, for example tablets coated with sugar, tablets coated with gelatin film, tablets coated with enteric coating layers, tablets coated with films or double layered tablets and multilayered tablets.

For the purpose of to shape in the form of pills, carriers which are known and widely used in this field can also be used, for example, excipients such as glucose, lactose, starch, coconut butter, hydrogenated vegetable oils, kaolin and talc; binders such as powdered Gummi Arabicum, powdered Tragacanth, gelatin and ethanol; desintegrators such as laminaria and agar-agar are included.

For the purpose of to shape in the form of suppositories, carriers, which are known and widely used in this field can also be used, for example, polyethylene glycols, coconut butter, higher alcohols, esters of higher alcohols, gelatin and semi-synthesized glycerides are included.

For the purpose of to make in the form of injection preparations, solutions and suspensions are sterilized and are preferably isotonic to blood. In making injection preparations in the form of solutions, emulsions and suspensions, every diluents which are commonly used in this field can also be used, for example, water, ethyl alcohol, propylene glycol, ethoxylated isostearyl alcohol, polyoxylated isostearyl alcohol and polyoxyethylene sorbitane fatty acid esters are included. In these instances, adequate amounts of sodium chloride, glucose or glycerin can be added to contain in the desired preparations for the purpose of to have tehm isotonic. Furthermore, the usual dissolving agents, buffers, analgesic agents and other agents can be added, as well as coloring agents, preservitives, perfums, seasoning agents, sweetening agents and other medicines can also be added into the desired preparations, if necessary.

The amount of compound of the general formula (1) or salt thereof to be contained in the pharmaceutical composition for curing and/or improving arrhythmia according to the present invention is not especially restricted and it can suitably be selected from wide range, and usually 1 to 70% by weight of the whole composition, preferably 1 to 30% by weight of the whole composition is used.

Methods for administering the pharmaceutical compositions for curing and/or improving arrhythmia according to the present invention are not specifically restricted, the compositions can be used in various forms of preparations depending upon the age, the distinction of gender, the degree of symtoms and other conditions of the patiant without any restriction. For example, tablets, pills, solutions, suspensions, emulsions, granules and capsules are administered orally; injection preparations are administered intraveneously singly, or administered with usual injectable transfusions such as glucose solutions, amino acids solutions and others; if necessary the injection preparations are asministered singly intramuscularly, intracutaneously, subcutaneously or intraperitoneally. The suppositories are administered into rectum.

The dosage of carbostyril derivative or salt thereof of the general formula (1) according to the present invention can be selected suitably depend on the method for administrations, the age of the patient, the distinction of gender and other conditions, as well as the degree of the symptoms, and generally a pharmaceutical composition containing 0.1 to 10 mg per kg of the body weight per day of the active ingredient of carbostyril derivative or salt represented by the general formula (1) may be used. Further, 2 to 200 mg of active ingredient may be contained in the administration unit form.

Examples of preparation of pharmaceutical compositions:

| (1) Preparation of tablets - 1 | |
|---|---|
| 3-Diethylamino-8-methyl-3,4-dihydrocarbostyril | 5 mg |
| Starch | 132 mg |
| Magnesium stearate | 18 mg |
| Lactose | 45 mg |
| | 200 mg |

By using an usual procedure, tablets having the above-mentioned formulation were prepared.

| (2) Preparation of tablets - 2 | |
|---|---|
| 3-{N-Methyl-N-[2-(3,4-dimethoxyphenyl)ethyl]}-8-methylcarbostyril | 10 mg |
| Starch | 127 mg |
| Magnesium stearate | 18 mg |
| Lactose | 45 mg |
| | 200 mg |

By using an usual procedure, tables having the above-mentioned formulation were prepared.

| (3) Preparation of injectable solution | |
|---|---|
| 3-(4-Benzyl-1-piperidinyl)-8-methyl carbostyril | 500 mg |
| Polyethylene glycol (Molecular weight: 4000) | 0.3 g |
| Sodium chloride | 0.9 g |
| Polyoxyethylene sorbitane monooleate | 0.4 g |
| Sodium metabisulfite | 0.1 g |
| Methyl p-hydroxybenzoate | 0.18 g |
| Propyl p-hydroxybenzoate | 0.02 g |
| Distilled water for injection | 100 ml |

The above-mentioned methyl p-hydroxybenzoate, propyl p-hydroxybenzoate, sodium metabisulfite and sodium chloride were dissolved in distilled water for injection at 80° C. with stirring. The thus obtained solution was cooled to 40° C., then 3-(4-benzyl-1-piperidinyl)-8-methyl carbostyril, next polyethylene glycol and polyoxyethylene sorbitane monoleate were dissolved therein. The final volume of the injection solution was adjusted by adding distilled water for injection, then the thus obtained solution was sterilized by filtering by using a suitable filter paper, then the sterilized solution was filled 1 ml each in an amplule to prepare the desired injection preparation.

Pharmacological Test

The test was conducted by method similar to that described in an article written by Hirooka, et al. Circ. Res., Vol. 48, pages 510–518 (1980) in which the muscle of ventricular of dog was used as a test sample.

A cat, having 1.5 to 5 kg of body weight, was anesthetized by intramuscular injection with 30 mg/kg of ketamine hydrochloride and intraperitoneal injection with 20 mg/kg of sodium pentobarbital, then the heart was enucleated from the cat and immersed in a chilled Tyrode's solution. Next, by a conventional procedure, a sample of musculi papillaris ventriculi detri was enucleated, then the sample was suspended in Magnus equipment which was filled with Tyrode's solution (containing 137 mM of NaCl, 15.9 mM of $NaHCO_3$, 5.5 mM of glucose, 1.0 mM of $MgCl_2$, 0.42 mM of $NaH_2PO_4$, 2.7 mM of KCl and 1.8 mM of $CaCl_2$). The Tyrode's solution was blown with a mixed gas consisting of 95% of $O_2$ and 5% of $CO_2$, and was kept a temperature of 37° C. The sample was suspended with 0.5 g of static tension. The sample was subjected to stabilize by applying an electrical stimulations with 0.5 Hz frequency. Then the electrical stimulations were stopped, the Tyrode's solution was substituted with K-free (potassium free) Tyrode's solution. 30 Minutes after the substitution of the Tyrode's solution, the k-free (potassium free) Tyrode's solution was then substituted with K- and Ca-free (potassium and calcium free) Tyrode's solution. 30 Minutes after the second substitution, the K- and Ca- free Tyrode's solution was then substituted with K-free Tyrode's solution (which contains 3.6 mM of Ca). 10 Minutes after the last substitution of Tyrode's solution, the sample of musculi papillaris ventriculi dextri was subjected to train stimulations by applying an electric pulse of 320 milliseconds interval in every 5 minutes. In the case of a half number of electrical pulse stimulations, after-contractions were observed when the stimulation were stopped. When the contractions induced by electrical pulse stimulation and the aftercontractions were observed become constant and stabilized, then each of the test compounds was applied to the sample accumulatively in 20 minutes intervals. The contraction induced by 10 times of electrical pulse stimulations and the aftercontraction observerd after the first electrical pulse stimulation were determined and shown in Table 1 as follows.

TABLE 1

| Test compound No. | |
|---|---|
| 1. | 3-Diethylamino-8-methyl-3,4-dihydrocarbostyril hydrochloride |
| 2. | 3-Diethylamino-8-methylcarbostyril oxalate |
| 3. | 6-Pyrrolidinyl-8-methyl-3,4-dihydrocarbostyril hydrochloride |
| 4. | 3-{N-Methyl-N-[2-(3,4-dimethoxyphenyl)ethyl]}-8-methylcarbostyril |
| 5. | 3-Pyrrolidinyl-8-fluorocarbostyril |
| 6. | 3-Diethylamino-6,8-dichloro-3,4-dihydrocarbostyril hydrochloride |
| 7. | 3-Ethylamino-8-methyl-3,4-dihydrocarbostyril hydrochloride |
| 8. | 3-[N-(2-Hydroxyethyl)-N-benzylamino]-8-methylcarbostyril |
| 9. | 3-Formylamino-8-methyl-3,4-dihydrocarbostyril |
| 10. | 3-Diethylaminoacetylamino-8-methyl-3,4-dihydrocarbostyril oxalate |
| 11. | 3-(4-Benzyl-1-piperidinyl)-8-methylcarbostyril hydrochloride |
| 12. | 3-(4-Methyl-1-piperazinyl)-8-methylcarbostyril hydrochloride |
| 13. | 8-Phenyl-6-pyrrolidino-3,4-dihydrocarbostyril hydrochloride |
| 14. | 5-Pyrrolidino-8-methyl-3,4-dihydrocarbostyril hydrochloride |
| 15. | 3-(N-Methyl-N-cyclohexyl)-8-methylcarbostyril hydrochloride |
| 16. | 4-Pyrrolidino-8-methylcabrosytril oxalate |
| 17. | 3-(N-Phenyl-N-ethylamino)-8-methylcarbostyril |
| 18. | 3-(4-Benzyl-1-piperidinylacetylamino)-8-methylcarbostyril hydrochloride |
| 19. | 3-(Pyrrolidinoacetylamino)-8-methylcarbostyril hydrochloride |
| 20. | 3-(4-Phenyl-1-piperazinyl)methylcarbostyril |
| 21. | 3-Di-n-Butylamino-8-methylcarbostyril hydrochloride |
| 22. | 3-Pyrrolidinyl-8-isopropylcarbostyril hydrochloride |
| 23. | 3-[4-(3,4-Dimethoxybenzoyl)-1-piperazinyl]-8-methylcarbostyril |
| 24. | 3-(4-Hydroxy-1-piperidinyl)-8-methylcarbostyril hydrochloride |
| 25. | 3-Morpholino-8-methyl-3,4-dihydrocarbostyril hydrochloride |
| 26. | 3-Amino-6,8-dichloro-3,4-dihydrocarbostyril hydrochloride |
| 27. | 3-Pyrrolidino-8-methoxycabrostyril hydrochloride |
| 28. | 3-[N-Methyl-N-(2-diethylaminoetyl)]-8-methylcarbostyril fumarate |
| 29. | 3-(4-Benzyl-1-piperazinyl)-8-methylcarbostyril hydrochloride |
| 30. | 4-(4-Methyl-1-piperazinyl)-8-fluorocarbostyril hydrochloride |
| 31. | 3-(4-Allyl-1-piperazinyl)-8-methylcarbostyril hydrochloride |

TABLE 1-continued

| | |
|---|---|
| 32. | 3-(4-Ethoxycarbonylmethyl-1-piperazinyl)-8-methylcabrostyril hydrochloride |
| 33. | 3-{4-[3-(4-Fluorobenzoyl)propyl]-1-piperazinyl}-8-methylcarbostyril hydrochloride |
| 34. | 3-(4-Methyl-1-piperazinyl)-8-fluorocarbostyril hydrochloride |
| 35. | 3-(4-Methyl-1-piperazinyl)-8-chlorocarbostyril hydrochloride |
| 36. | 3-Morpholino-8-methylcarbostyril |
| 37. | 3-Thiomorpholino-8-methylcarbostyril |
| 38. | 3-(1,4-Diazabicyclo[4.3.0]nonan-4-yl)-8-methylcarbostyril hydrochloride |
| 39. | 3-(4-n-Propyl-1-piperazinyl)-8-methylcarbostyril hydrochloride |
| 40. | 3-(4-Methyl-1-homopiperazinyl)-8-methyl-carbostyril hydrochloride |
| 41. | 3-[4-(2,2,2-Trifluoroethyl)-1-piperazinyl]-8-methylcarbostyril hydrochloride |
| 42. | 3-(2-Diethylaminomethyl-1-pyrrolidinyl)-8-methylcabrosytril hydrochloride |
| 43. | 3-(4-Methyl-1-piperazinyl)-8-trifluoromethyl-carbostyril hydrochloride |
| 44. | 3-(4-Methyl-1-piperazinyl)-8-benzyloxy-carbostyril hydorchloride |
| 45. | 3-(4-Methyl-1-piperazinyl)-8-ethylcarbostyril hydrochloride |
| 46. | 3-[2-(1-Pyrrolidinylmethyl)-1-pyrrolidinyl]-8-methylcarbostyril oxalate |
| 47. | 3-(2-Morpholinomethyl-1-pyrrolidinyl)-8-methylcabrostyril hydorchloride |
| 48. | 5-(4-Methyl-1-piperazinyl)-8-methyl-3,4-dihydrocarbostyril hydrochloride |
| 49. | 3-(2,4-Dimethyl-1-piperazinyl)-8-methyl-carbostyril hydrochloride |
| 50. | 3-(3-Morpholino-1-pyrrolidinyl)-8-methyl-carbostyril hydrochloride |
| 51. | 3-[N-Methyl-N-2-(3,4-dimethoxyphenyl)ethyl]-aminomethy-8-methylcarbostyril |
| 52. | 3-[3-(1-Pyrrolidinyl)-1-pyrrolidinyl]-8-methylcarbostyril hydrochloride |
| 53. | 3-[4-(1-Piperidinyl)-1-piperidinyl]-8-methyl-carbostyril hydrochloride |
| 54. | 3-{4-[3-(4-Pyridyl)propyl-1-piperazinyl]}-8-methylcarbostyril dihydrochloride |
| 55. | 3-(1-Pyridinium)-8-methylcarbostyril chloride |
| 56. | 3-(1-Pyrrolidinyl)-8-allyloxycarbostyril hydrochloride |
| 57. | 3-[4-(2-Hydroxyethyl)-1-piperazinyl]-8-methyl-carbostyril hydrochloride |
| 58. | 3-(2-Diethylamido-1-pyrrolidinyl)-8-fluoro-carbostyril |
| 59. | 3-(4-Propargyl-1-piperazinyl)-8-methylcarbostyril hydorchloride |
| 60. | 3-(4-Acetylmethyl-1-piperazinyl)-8-methyl-carbostyril hydrochloride |
| 61. | 3-(1-Insolinyl)-8-methylcarbostyril |
| 62. | 3-Diethylamino-8-acetylnethoxycarbostyril hydrochloride |
| 63. | 3-[4-(1-Pyrrolidinylcarbonylmethyl)-1-piperazinyl]-8-methylcarbostyril hydrochloride. |
| 64. | 3-[4-(2-Morpholinoethyl)-1-piperazinyl]-8-methylcarbostyril dihydrochloride |
| 65. | 3-{4-[2-Thienyl)methyl]-1-piperazinyl}-8-methylcarbostyril hydrochloride |
| 66. | 3-(4-Cyclohexyl-1-piperazinyl)-8-methylcarbostyril hydrochloride |
| 67. | 3-[2-(4-Methyl-1-piperazinylmethyl)-1-pyrrolidinyl]-8-methylcarbostyril dioxalate |
| 68. | 3-[3-(4-Methyl-1-piperazinyl)-1-pyrrolidinyl]-8-methylcarbostyril dihydrochloride |
| 69. | 3-[3-(3,5-Dimethyl-1-piperidinylmethyl)-morpholino]-8-methylcarbostyril hydrochloride |
| 70. | 3-(4-Diethylamino-1-piperidinyl)-8-methyl-carbostyril hydrochloride |
| 71. | 3-(4-Methyl-1-piperazinyl)-6-methoxy-8-methylcarbostyril hydrochloride |
| 72. | 1,8-Dimethyl-3-(1-pyrrolidinyl)carbostyril |
| 73. | 3-(4-Cyclopropylmethyl-1-piperazinyl)-8-8-methylcarbostryil hydrochloride |

| Test compound No. | Dosage (μmole) | LC* | A-1* |
|---|---|---|---|

TABLE 1-continued

| | | | |
|---|---|---|---|
| 1 | Control | 100 | 100 |
| | 100 | 95.6 | 69.8 |
| | 300 | 75.3 | 29.9 |
| 2 | Control | 100 | 100 |
| | 30 | 98.1 | 92.3 |
| | 100 | 90.1 | 52.4 |
| | 300 | 74.5 | 26.2 |
| 3 | Control | 100 | 100 |
| | 30 | 98.9 | 89.7 |
| | 100 | 95.0 | 61.2 |
| | 300 | 76.7 | 25.3 |
| 4 | Control | 100 | 100 |
| | 30 | 96.7 | 94.0 |
| | 100 | 92.1 | 83.7 |
| | 300 | 74.2 | 39.7 |
| 5 | Control | 100 | 100 |
| | 10 | 105.8 | 95.3 |
| | 30 | 100.7 | 77.4 |
| | 100 | 96.4 | 44.5 |
| | 300 | 91.0 | 25.8 |
| 6 | Control | 100 | 100 |
| | 100 | 91.1 | 63.0 |
| | 300 | 71.7 | 30.9 |
| 7 | Control | 100 | 100 |
| | 300 | 116.6 | 90.2 |
| | 1000 | 90.8 | 57.3 |
| 8 | Control | 100 | 100 |
| | 30 | 82.6 | 69.4 |
| | 100 | 75.8 | 32.3 |
| | 300 | 63.7 | 32.3 |
| 9 | Control | 100 | 100 |
| | 300 | 102.9 | 76.8 |
| | 1000 | 115.3 | 58.0 |
| 10 | Control | 100 | 100 |
| | 10 | 102.4 | 98.6 |
| | 30 | 101.3 | 84.3 |
| | 100 | 81.6 | 48.3 |
| 11 | Control | 100 | 100 |
| | 30 | 95.2 | 94.9 |
| | 100 | 94.3 | 69.3 |
| | 300 | 84.6 | 40.7 |
| 12 | Control | 100 | 100 |
| | 3 | 94.2 | 88.8 |
| | 10 | 89.6 | 70.1 |
| | 30 | 85.9 | 40.3 |
| 13 | Control | 100 | 100 |
| | 30 | 91.3 | 87.8 |
| | 100 | 82.4 | 69.2 |
| | 300 | 77.3 | 49.3 |
| 14 | Control | 100 | 100 |
| | 30 | 91.7 | 78.0 |
| | 100 | 93.6 | 60.6 |
| | 300 | 88.4 | 25.8 |
| 15 | Control | 100 | 100 |
| | 30 | 98.7 | 90.2 |
| | 100 | 103.3 | 83.0 |
| | 300 | 110.8 | 62.2 |
| 16 | Control | 100 | 100 |
| | 30 | 82.4 | 68.1 |
| | 100 | 62.5 | 24.5 |
| 17 | Control | 100 | 100 |
| | 30 | 102.3 | 77.6 |
| | 100 | 95.9 | 62.6 |
| | 300 | 96.0 | 45.2 |
| 18 | Control | 100 | 100 |
| | 30 | 109.5 | 99.6 |
| | 100 | 118.0 | 92.7 |
| | 300 | 127.3 | 44.7 |
| 19 | Control | 100 | 100 |
| | 10 | 89.6 | 87.8 |
| | 30 | 79.5 | 72.3 |
| | 100 | 60.8 | 34.5 |
| 20 | Control | 100 | 100 |
| | 30 | 93.2 | 86.2 |
| | 100 | 90.3 | 62.1 |
| 21 | Control | 100 | 100 |
| | 30 | 95.8 | 82.7 |
| | 100 | 90.6 | 72.9 |
| | 300 | 72.3 | 61.0 |
| 22 | Control | 100 | 100 |
| | 30 | 99.5 | 81.9 |
| | 100 | 91.2 | 65.1 |
| | 300 | 80.2 | 46.7 |
| 23 | Control | 100 | 100 |
| | 30 | 93.3 | 84.1 |
| | 100 | 85.9 | 72.3 |
| | 300 | 86.9 | 36.9 |
| 24 | Control | 100 | 100 |
| | 30 | 86.7 | 80.1 |
| | 100 | 79.6 | 63.3 |
| | 300 | 71.0 | 51.6 |
| 25 | Control | 100 | 100 |
| | 100 | 91.2 | 89.9 |
| | 300 | 73.3 | 65.9 |
| 26 | Control | 100 | 100 |
| | 100 | 95.8 | 85.7 |
| | 300 | 83.6 | 44.9 |
| 27 | Control | 100 | 100 |
| | 30 | 95.3 | 85.2 |
| | 100 | 85.1 | 59.5 |
| | 300 | 83.5 | 34.7 |
| 28 | Control | 100 | 100 |
| | 10 | 89.6 | 84.4 |
| | 30 | 72.9 | 53.1 |
| 29 | Control | 100 | 100 |
| | 10 | 99.8 | 90.3 |
| | 30 | 98.6 | 73.8 |
| | 100 | 97.3 | 59.6 |
| 30 | Control | 100 | 100 |
| | 30 | 96.2 | 78.7 |
| | 100 | 91.1 | 72.1 |
| | 300 | 80.1 | 37.7 |
| 31 | Control | 100 | 100 |
| | 10 | 100.8 | 92.4 |
| | 30 | 88.3 | 72.5 |
| 32 | Control | 100 | 100 |
| | 30 | 111.4 | 109.0 |
| | 100 | 101.4 | 92.2 |
| | 300 | 84.9 | 53.1 |
| 33 | Control | 100 | 100 |
| | 30 | 97.5 | 55.7 |
| | 100 | 73.2 | 40.6 |
| 34 | Control | 100 | 100 |
| | 30 | 116.2 | 92.3 |
| | 100 | 107.4 | 57.2 |
| | 300 | 92.0 | 27.9 |
| 35 | Control | 100 | 100 |
| | 10 | 97.5 | 96.0 |
| | 30 | 97.4 | 87.5 |
| | 100 | 89.2 | 60.4 |
| 36 | Control | 100 | 100 |
| | 30 | 97.6 | 73.4 |
| | 100 | 95.2 | 43.2 |
| | 300 | 102.9 | 47.4 |
| 37 | Control | 100 | 100 |
| | 10 | 98.5 | 103.6 |
| | 30 | 94.4 | 71.0 |
| | 100 | 87.6 | 63.3 |
| 38 | Control | 100 | 100 |
| | 10 | 100.1 | 97.9 |
| | 30 | 93.9 | 76.8 |
| | 100 | 93.7 | 64.4 |
| 39 | Control | 100 | 100 |
| | 10 | 100.6 | 71.3 |
| | 30 | 97.5 | 52.3 |
| | 100 | 78.6 | 32.3 |
| 40 | Control | 100 | 100 |
| | 10 | 91.1 | 88.1 |
| | 30 | 89.8 | 82.2 |
| | 100 | 74.6 | 47.5 |
| 41 | Control | 100 | 100 |
| | 10 | 99.2 | 87.1 |
| | 30 | 88.5 | 69.1 |
| | 100 | 74.5 | 31.6 |
| 42 | Control | 100 | 100 |
| | 3 | 100.7 | 97.3 |
| | 10 | 97.9 | 78.4 |
| | 30 | 84.9 | 40.6 |
| 43 | Control | 100 | 100 |
| | 10 | 96.5 | 91.9 |
| | 30 | 91.5 | 65.5 |
| | 100 | 75.4 | 38.1 |
| 44 | Control | 100 | 100 |
| | 10 | 97.6 | 84.7 |

TABLE 1-continued

| | | | |
|---|---|---|---|
| | 30 | 86.1 | 50.3 |
| 45 | Control | 100 | 100 |
| | 10 | 94.4 | 96.0 |
| | 30 | 88.7 | 88.8 |
| | 100 | 81.7 | 73.1 |
| 46 | Control | 100 | 100 |
| | 3 | 96.1 | 94.8 |
| | 10 | 90.8 | 76.8 |
| | 30 | 76.9 | 36.2 |
| 47 | Control | 100 | 100 |
| | 3 | 97.6 | 89.4 |
| | 10 | 100.5 | 69.5 |
| | 30 | 90.8 | 41.1 |
| 48 | Control | 100 | 100 |
| | 30 | 91.6 | 80.3 |
| | 100 | 93.9 | 69.7 |
| | 300 | 81.2 | 48.3 |
| 49 | Control | 100 | 100 |
| | 10 | 99.8 | 99.9 |
| | 30 | 102.5 | 94.9 |
| | 100 | 98.5 | 64.0 |
| 50 | Control | 100 | 100 |
| | 10 | 103.0 | 89.5 |
| | 30 | 101.8 | 81.0 |
| | 100 | 86.5 | 57.6 |
| 51 | Control | 100 | 100 |
| | 10 | 102.9 | 96.2 |
| | 30 | 95.5 | 87.4 |
| | 100 | 86.9 | 54.5 |
| 52 | Control | 100 | 100 |
| | 3 | 98.8 | 95.6 |
| | 10 | 95.7 | 68.0 |
| | 30 | 90.4 | 50.0 |
| 53 | Control | 100 | 100 |
| | 10 | 102.2 | 99.4 |
| | 30 | 100.6 | 94.7 |
| | 100 | 89.5 | 61.6 |
| 54 | Control | 100 | 100 |
| | 10 | 90.7 | 89.1 |
| | 30 | 80.6 | 75.9 |
| | 100 | 79.6 | 62.9 |
| 55 | Control | 100 | 100 |
| | 100 | 93.6 | 93.1 |
| | 300 | 79.4 | 77.4 |
| 56 | Control | 100 | 100 |
| | 10 | 92.0 | 77.1 |
| | 30 | 81.7 | 46.7 |
| | 100 | 70.7 | 34.5 |
| 57 | Control | 100 | 100 |
| | 30 | 107.4 | 99.4 |
| | 100 | 106.8 | 91.6 |
| | 300 | 105.3 | 66.0 |
| 58 | Control | 100 | 100 |
| | 30 | 93.4 | 85.9 |
| | 100 | 89.4 | 70.2 |
| | 300 | 83.2 | 23.7 |
| 59 | Control | 100 | 100 |
| | 10 | 95.7 | 84.5 |
| | 30 | 90.3 | 75.9 |
| | 100 | 80.4 | 62.6 |
| 60 | Control | 100 | 100 |
| | 10 | 94.5 | 92.0 |
| | 30 | 83.9 | 78.0 |
| | 100 | 71.3 | 53.4 |
| 61 | Control | 100 | 100 |
| | 30 | 109.9 | 98.4 |
| | 100 | 112.9 | 90.0 |
| | 300 | 119.0 | 54.4 |
| 62 | Control | 100 | 100 |
| | 30 | 99.8 | 95.7 |
| | 100 | 90.9 | 75.3 |
| 63 | Control | 100 | 100 |
| | 30 | 96.7 | 80.0 |
| | 100 | 93.7 | 73.8 |
| | 300 | 81.4 | 52.9 |
| 64 | Control | 100 | 100 |
| | 30 | 101.0 | 93.1 |
| | 100 | 100.8 | 81.8 |
| | 300 | 95.2 | 49.3 |
| 65 | Control | 100 | 100 |
| | 30 | 108.2 | 100.4 |
| | 100 | 96.3 | 80.0 |
| | 300 | 93.3 | 74.6 |
| 66 | Control | 100 | 100 |
| | 3 | 102.1 | 98.9 |
| | 10 | 98.8 | 86.5 |
| | 30 | 84.8 | 64.7 |
| 67 | Control | 100 | 100 |
| | 10 | 100 | 85.9 |
| | 30 | 95.3 | 52.4 |
| | 100 | 80.0 | 37.3 |
| 68 | Control | 100 | 100 |
| | 10 | 93.5 | 91.0 |
| | 30 | 92.9 | 77.5 |
| | 100 | 85.8 | 51.4 |
| 69 | Control | 100 | 100 |
| | 3 | 98.6 | 97.4 |
| | 10 | 94.2 | 80.5 |
| | 30 | 82.5 | 52.9 |
| 70 | Control | 100 | 100 |
| | 3 | 97.7 | 94.1 |
| | 10 | 95.7 | 78.4 |
| | 30 | 87.5 | 55.8 |
| 71 | Control | 100 | 100 |
| | 10 | 91.7 | 87.8 |
| | 30 | 88.8 | 80.5 |
| | 100 | 76.0 | 44.6 |
| 72 | Control | 100 | 100 |
| | 10 | 103.1 | 96.0 |
| | 30 | 90.6 | 78.5 |
| | 100 | 73.6 | 36.9 |
| 73 | Control | 100 | 100 |
| | 3 | 104.8 | 98.7 |
| | 10 | 102.5 | 85.2 |
| | 30 | 95.8 | 43.1 |

*LC: Contraction induced by 10 times of electrical pulse stimulations
**A-1: Aftercontraction observed after the first electrical pulse stimulation The present invention is now explained by illustrating the following Reference Examples, however, the present invention is not restricted only by these Examples.

REFERENCE EXAMPLES

10 Grams of diethyl 2-acetylamino-2-(2-nitro-3-methylbenzyl)malonate and 1 g of 10% Pd-C were suspended in 50 ml of acetic acid, and the suspension was catalytically reduced under 3 to 3.5 atmospheric pressure at 60° to 70° C. by hydrogenation. After the hydrogenation was finished, the catalyst was removed by filtration, and the solvent was removed by evaporation. The residue thus obtained was recrystallized from ethanol to obtain 2.7 g of ethyl 3-acetylamino-8-methyl-3,4-dihydrocarbostyril-3-carboxylate. White powdery substance. Melting point: 236.5°–238.5° C.

EXAMPLE 1

To 2.7 g of ethyl 3-acetylamino-8-methyl-3,4-dihydrocarbostyril-3-carboxylate was added 60 ml of 20%-hydrochloric acid, then the mixture was refluxed by heating for 2 hours. The solvent was removed by evaporation, then water was removed by azetropic distillation with ethanol. The residue thus obtained was recrystallized from methanol-diethyl ether to obtain 1.74 g of 3-amino-8-methyl-3,4-dihydrocarbostyril hydrochloride. Colorless flake-like crystals. Melting point: Over 300° C.

NMR (DMSO-$d_6$) δ: 2.26 (3H, s); 3.03–3.45 (2H, m); 4.16 (1H, dd, J=8 Hz, 12 Hz); 6.80–7.20 (3H, m); 8.80 (2H, br.); 10.10 (1H, brs.).

EXAMPLES 2–34

By using a suitable starting materials and by method similar to that described in Example 1, there were prepared compounds as shown in the following Table 2.

TABLE 2

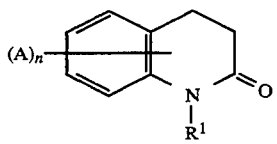

| Example No. | $R^1$ | n | A | Crystal form (Recrystallization solvent) | Melting point (°C.) | Salt |
|---|---|---|---|---|---|---|
| 2 | H | 2 | 3-N⟨ ⟩ | Colorless flake-like crystals (Ethanol) | 267-269 (decomp.) | HCl |
| 3 | H | 2 | 3-$NH_2$ 8-$OCH_3$ | Colorless needle-like crystals (Ethanol) | 267-272 | HCl |
| 4 | H | 2 | 3-N⟨ ⟩ 8-$OCH_3$ | Colorless needle-like crystals (Ethanol-diethyl ether) | 242-243 (decomp.) | HCl |
| 5 | H | 2 | 3-$NHC_2H_5$ 8-$OCH_3$ | Colorless needle-like crystals (Ethanol-diethyl ether) | 248-251 | HCl |
| 6 | H | 2 | 3-$N(C_2H_5)_2$ 8-$OCH_3$ | Colorless powdery substance (Ethanol-diethyl ether) | 196-199 | HCl |
| 7 | H | 2 | 3-N⟨ ⟩ 8-$CH_3$ | Light brawn powdery substance (Ethyl acetate-ethanol) | 258-262 (decomp.) | HCl |
| 8 | H | 2 | 3-$NHC_2H_5$ 8-$CH_3$ | Colorless powdery substance (Ethanol-diethyl ether) | 277-279 (decomp.) | HCl |
| 9 | H | 2 | 3-$N(C_2H_5)_2$ 8-$CH_3$ | White powdery substance (Ethanol-diethyl ether) | 231.5-233 | HCl |
| 10 | H | 2 | 3-NHCHO 8-$CH_3$ | Colorless needle-like crystals (Ethanol-dichloromethane) | 258-261 | — |
| 11 | H | 2 | 3-$N(CH_3)_2$ 8-$CH_3$ | Light brawn powdery substance (Ethanol-diethyl ether) | 254-254.5 | HCl |
| 12 | H | 2 | 3-N⟨ O⟩ | Colorless flaklike crystals (Methanol-diethyl ether) | 235-238 (decomp.) | HCl |
| 13 | H | 2 | 8-$CH_3$ 3-$NH_2$ 8-$CO_2H$ | Colorless needle-like crystals (Water-aceton) | More than 300 | HCl |
| 14 | $CH_3$ | 2 | 3-$N(C_2H_5)_2$ 8-$CH_3$ | Light brawn powdery substance (Acetone-n-hexane) | 162.5-164.5 | HCl |
| 15 | H | 3 | 3-$NH_2$ 6-Cl, 8-Cl | Colorless needle-like crystal (Water-ethanol) | 274-278 | HCl |
| 16 | H | 3 | 3-$N(C_2H_5)_2$ 6-Cl, 8-Cl | Colorless powdery substance (Ethanol-diethyl ether) | 224-225.5 | HCl |
| 17 | H | 2 | 6-N⟨ ⟩ 8-$CH_3$ | White powdery substance (Ethanol-diethyl ether) | 242-244 | HCl |

TABLE 2-continued

| Example No. | R¹ | n | A | Crystal form (Recrystallization solvent) | Melting point (°C.) | Salt |
|---|---|---|---|---|---|---|
| 18 | CH₃ | 2 | 6-N⟨⟩ | White powdery substance (Ethanol-diethyl ether) | 145–146 | Oxalate |
| 19 | H | 2 | 6-N(C₂H₅)₂ 8-CH₃ | White powdery substance (Ethanol-diethyl ether) | 236–237 | HCl |
| 20 | H | 1 | 3-NHCOCH₂N(C₂H₅)₂ | White powdery substance (Ethanol-diethyl ether) | 184–185.5 | Oxalate |
| 21 | H | 2 | 3-NHCOCH₂N(C₂H₅)₂ 8-OCH₃ | White powdery substance (Isopropanol-n-hexane) | 113–114.5 | HCl |
| 22 | H | 2 | 3-NHCOCH₂N(C₂H₅)₂ 8-CH₃ | White powdery substance (Methanol-diethyl ether) | 213–214 (decomp.) | Oxalate |
| 23 | CH₃ | 2 | 6-N(C₂H₅)₂ 8-CH₃ | White powdery substance (Ethanol-diethyl ether) | 162–164 | Oxalate |
| 24 | CH₃ | 1 | 8-N⟨⟩ | White powdery substance (Ethanol-diethyl ether) | 174.5–177 | HCl |
| 25 | CH₃ | 1 | 8-N(C₂H₅)₂ | White powdery substance (Ethanol-diethyl ether) | 166–168.5 | HCl |
| 26 | H | 2 | 6-N⟨⟩ | Light yellow powdery substance (Ethanol-diether ether) | 233–235 | HCl |
| 27 | H | 1 | 8-fenyl 8-N⟨⟩ | Colorless flake-like crystals (Ethanol) | 222–224 | HCl |
| 28 | H | 2 | 5-N⟨⟩ | Colorless flake-like crystals (Ethanol-diethyl ether) | 234.5–239 | HCl |
| 29 | H | 2 | 8-CH₃ 7-NHCOCH₃ 8-CH₃ | Colorless needle-like crystals (Dimethylformamide-ethanol) | 291.5–292 | — |
| 30 | H | 2 | 7-NH₂ 8-CH₃ | Light-yellow needle-like (Methal-water) | 294.5–296 (decomp.) | HCl |
| 31 | H | 2 | 7-N⟨⟩ | Light brawn needle-like crystals (Ethanol-diethyl ether) | 218–219.5 | HCl |
| 32 | H | 2 | 8-CH₃ 7-N(C₂H₅)₂ | Colorless prism- | 202–204.5 | HCl |

TABLE 2-continued

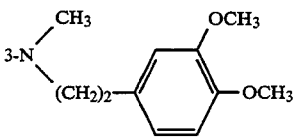

| Example No. | R¹ | n | A | Crystal form (Recrystallization solvent) | Melting point (°C.) | Salt |
|---|---|---|---|---|---|---|
| | | | 8-CH₃ | like crystals (Ethanol-diethyl ether) | | |
| 33 | H | 2 | 6-NH₂ 8-F | Light brawn needle-like crystals (Ethanol-n-hexane) | 171–172.5 | — |
| 34 | H | 2 | 6-N⟨ ⟩ 8-F | Colorless needle-like crystals (Ethanol) | 247–251 | HCl |

EXAMPLE 35

0.5 Gram of 2-[2-(4-benzyl-1-piperidinyl)acetyl-]amino-3-methylbenzaldehyde was dissolved in 10 ml of ethanol, then 0.11 g of sodium ethylate was added thereto, and the mixture was refluxed by heating for 2 hours. To the reaction mixture was added water, and was extracted with dichloromethane. The extract was washed with water, then dried with anhydrous magnesium sulfate. The solvent was removed by evaporation, and the residue thus obtained was purified by a silica gel column chromatography (eluent: dichloromethane:methanol=100:1).

The product was converted into hydrochloride by using ethanol-HCl, and recrystallized from dichloromethane-ethanol to obtain 0.22 g of 3-(4-benzyl-1-piperidinyl)-8-methylcarbostyril hydrochloride. Light yellow powdery substance. Melting point: 221°–222° C. (decomposed).

EXAMPLES 36–82

By using suitable starting material, and by method similar to that described in Example 35, there were prepared compounds as shown in the following Table 3 and compound of Examples 90 mentioned below.

TABLE 3

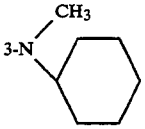

| Example No. | R¹ | n | A | Crystal form (Recrystallization solvent) | Melting point (°C.) | Salt |
|---|---|---|---|---|---|---|
| 36 | H | 2 | 3-N⟨ ⟩ | Light brown needle-like crystals (Ethanol) | 233–235 | HCl |
| 37 | H | 2 | 3-N(C₂H₅)₂ 8-CH₃ | Yellow powdery substance (Ethanol-n-hexane) | 158.5–160 (decomp.) | Oxalate |
| 38 | H | 2 | 3-N(CH₃)-(CH₂)₂-C₆H₃(OCH₃)₂ 8-CH₃ | Light yellow needle-like crystals (Methanol) | 166–167 | ½ fumarate |
| 39 | H | 2 | 3-N(CH₃)(cyclohexyl) | Colorless powdery substance (Ethanol-diethyl ether) | 204.5–205.5 | HCl |

TABLE 3-continued

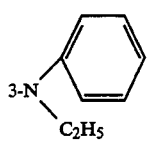

| Example No. | R¹ | n | A | Crystal form (Recrystallization solvent) | Melting point (°C.) | Salt |
|---|---|---|---|---|---|---|
| 40 | H | 2 | 8-CH₃ 3-N(n-C₄H₉)₂ 8-CH₃ | Colorless needle-like crystals (Acetone-n-hexane) | 179–181 | HCl |
| 41 | H | 2 | 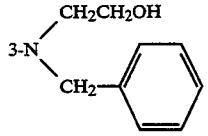 8-CH₃ | Light yellow needle-like crystals (Ethanol) | 202–204 | — |
| 42 | H | 2 | 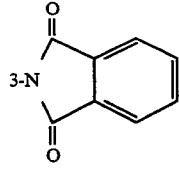 8-CH₃ | Colorless needle-like crystals (Ethanol-diethyl ether) | 136.5 | — |
| 43 | H | 2 | 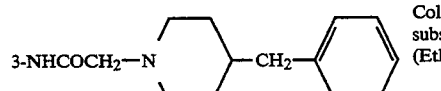 8-CH₃ | Light brawn powdery substance (Ethanol) | Over 300 | — |
| 44 | H | 2 | 3-N₃ 8-CH₃ | Light brawn powdery substance (Methanol-diethyl ether) | 270–273 (decomp.) | — |
| 45 | H | 2 | 3-NH₂ 8-CH₃ | Light brawn powdery substance (Chloroform) | 255–260 (decomp.) | — |
| 46 | H | 2 | 3-NHCOCH₂N(C₂H₅)₂ 8-CH₃ | Light yellow powdery substance (Ethanol-water) | 250–252 (decomp.) | HCl |
| 47 | H | 2 | 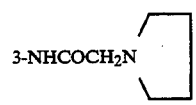 8-CH₃ | Colorless powdery substance (Ethanol-diethyl ether) | 160.5–162.5 | HCl |
| 48 | H | 2 |  8-CH₃ | Colorless needle-like crystals (Ethanol-water) | 262–264 (decomp.) | HCl |
| 49 | H | 2 | 3-N(CH₃)₂ 8-F | Colorless powdery substance (Ethanol-water) | 215–220 (decomp.) | HCl |
| 50 | H | 2 | 3-N(C₂H₅)₂ 8-F | Colorless powdery substance (Acetone-diethyl ether) | 191–195 | HCl |
| 51 | H | 2 | 3-N⟨pyrrolidine⟩ | Colorless needle-like crystals (Ethanol) | 207–214 (decomp.) | HCl |

TABLE 3-continued

[Structure: quinolin-2(1H)-one with (A)ₙ substituents and N-R¹]

| Example No. | R¹ | n | A | Crystal form (Recrystallization solvent) | Melting point (°C.) | Salt |
|---|---|---|---|---|---|---|
| 52 | H | 2 | 8-F<br>5-N(piperidinyl) | Light orange flake-like crystals (Ethanol) | 238.5–242 | HCl |
| 53 | H | 2 | 8-CH₃<br>4-<br>3-N(C₂H₆)₂ | Light yellow needle-line crystals (Isopropanol) | 187 | HCl |
| 54 | H | 2 | 3-N(4-methylpiperazinyl)N—CH₃ | Colorless powdery substance (Methanol-diethyl ether) | 283–287 (decomp.) | HCl |
| 55 | H | 2 | 8-CH₃<br>3-N(4-phenylpiperazinyl) | White powdery substance (Methanol) | 294–296 | — |
| 56 | H | 2 | 8-CH₃<br>3-NHC₂H₅<br>8-CH₃ | Light yellow needle-like crystals (Ethanol) | 230–232 | HCl |
| 57 | H | 2 | 3-N-piperazinyl-N—CO—(3,4-dimethoxyphenyl) | White powdery substance (Methanol) | 181–182 | — |
| 58 | H | 2 | 8-CH₃<br>3-N(4-benzylpiperazinyl)N—CH₂—Ph | Colorless flake-like crystals (Ethanol) | 198–198.5 | — |
| 59 | H | 2 | 8-F<br>3-N(C₂H₅)₂<br>8-OCH₃ | Colorless prism-like crystals (Ethanol-n-nexane) | 192–193 (decomp.) | HCl |
| 60 | H | 2 | 3-N(C₂H₅)₂<br>8-CH(CH₃)₂ | White powdery substance (Ethanol-diethyl ether) | 219–223 (decomp.) | HCl |

TABLE 3-continued

Structure: quinolin-2(1H)-one with (A)ₙ substituents on benzene ring and R¹ on nitrogen

| Example No. | R¹ | n | A | Crystal form (Recrystallization solvent) | Melting point (°C.) | Salt |
|---|---|---|---|---|---|---|
| 61 | H | 2 | 3-N(piperidinyl); 8-CN(CH₃)₂ | Colorless prism-like crystals (Ethanol-diethyl ether) | 220–228 (decomp.) | HCl |
| 62 | H | 2 | 3-N(piperidinyl); 8-OCH₃ | Light yellow needle-like crystals (Ethanol-diethyl ether) | 210–214 (decomp.) | HCl |
| 63 | H | 2 | 3-N(4-hydroxypiperidinyl)-OH; 8-CH₃ | White powdery substance (Ethanol-water) | 261–263 | HCl |
| 64 | H | 2 | 5-NHCOCH₂N(C₂H₅)₂; 8-CH₃ | Yellow powdery substance (Ethanol-diethyl ether) | 139.5–142.5 | HCl |
| 65 | H | 2 | 3-N(4-benzylpiperidinyl)-CH₂-Ph; 8-CH(CH₃)₂ | Colorless needle-like crystals (Isopropanol) | 190.5–192.5 | — |
| 66 | H | 2 | 3-N(4-benzylpiperidinyl)-CH₂-Ph; 8-OCH₃ | Colorless flake-like crystals (Ethanol-diethyl ether) | 204–210 | HCl |
| 67 | H | 2 | 3-N(4-hydroxypiperidinyl)-OH; 8-CH(CH₃)₂ | White powdery substance (Ethanol-diethyl ether) | 240–250 (decomp.) | HCl |
| 68 | H | 2 | 3-N(CH₃)(CH₂Ph); 8-OCH₃ | Colorless needle-like crystals (Ethanol-water) | 168–168.5 | — |
| 69 | H | 2 | 3-NHCH₃; 8-OCH₃ | Light yellow powder substance | 190–200 (decomp.) | HCl |

TABLE 3-continued structure:

![quinolinone with (A)n substituents, N-R¹, =O]

| Example No. | R¹ | n | A | Crystal form (Recrystallization solvent) | Melting point (°C.) | Salt |
|---|---|---|---|---|---|---|
| 70 | H | 2 | 3-NHCH₂CH 8-CH₃ | Light yellow needle-like crystals (Ethanol-diethyl ether) (Ethanol) | 172.5–173 | — |
| 71 | H | 2 | 3-N(C₂H₅)((CH₂)₂N(C₂H₅)₂) 8-CH₃ | Light yellow powdery substance (Isopropanol) | 187.5–188.5 | Di-fumarate |
| 72 | H | 2 | 3-N(C₂H₅)(cyclohexyl) 8-CH₃ | Light yellow prism-like crystals (Ethanol) | 202–202 | — |
| 73 | H | 2 | 5-NHCOCH₂Cl 8-CH₃ | Light yellow powdery substance (Acetone-water) | 270–272 | — |
| 74 | H | 2 | 3-NHCOCH₃ 8-CH₃ | White powdery substance (Acetone-water) | 240–243 | — |
| 75 | H | 2 | 3-NHCOCH₂—C₆H₅ 8-CH₃ | White powdery substance (Acetone-water) | 233–236 (decomp.) | — |
| 76 | H | 2 | 7-NHCOCH₃ 8-CH₃ | Light yellow powdery substance (Dimethylformamide) | 315–318 (decomp.) | — |
| 77 | H | 2 | 3-N(C₂H₅)₂ 8-OCH₂—C₆H₅ | Light yellow prism-like crystals (Ethanol-diethyl ether) | 200–205 | HCl |
| 78 | H | 2 | 3-N(pyrrolidinyl) 8-OCH₂—C₆H₅ | Yellow needle-like crystals (Ethanol) | 158–158.5 | — |
| 79 | H | 2 | 3-N(piperazinyl-N—CH₂—C₆H₅) 8-CH₃ | Colorless needle-crystals (Ethanol-water) | 268–270 (decomp.) | HCl |

TABLE 3-continued

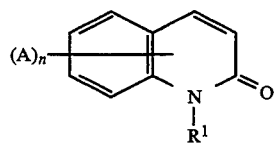

| Example No. | R¹ | n | A | Crystal form (Recrystallization solvent) | Melting point (°C.) | Salt |
| --- | --- | --- | --- | --- | --- | --- |
| 80 | H | 2 | 3-N⟨ ⟩NH<br>8-CH₃ | Colorless needle-like crystals (Ethanol-water) | Over 300 | HCl |
| 81 | H | 2 | 3-N⟨ ⟩N—CH₂CH=CH₂<br>8-CH₃ | White powdery substance (Ethanol) | 278–280 (decomp.) | HCl |
| 82 | H | 2 | 3-N⟨ ⟩N—CH₂CO₂C₂H₅<br>8-CH₃ | Colorless needle-like crystals (Ethanol) | 225–227 (decomp.) | HCl |

EXAMPLE 83

2.0 Grams of 4-chloro-8-methylcarbostyril, 5 ml of diethylamine, 0.2 g of copper iodide-copper powder mixture and 20 ml of N-methylpyrrolidone were placed in an autoclave and heated at 180°–190° C. for 10 hours. To the reaction mixture was added water, then extracted with ethyl acetate. The extract was washed with water, dried, and the solvent was removed by evaporation. The residue thus obtained was purified by a silica gel column chromatography (eluent: dichloromethane). The product was converted into hydrochloride by using ethanol-HCl, and recrystallized from acetone-diethyl ether to obtain 0.6 g of 4-diethylamino-8-methylcarbostyril hydrochloride. Light brown powdery substance. Melting point: 183°–186° C.

EXAMPLE 84–89

By using suitable starting materials, and by method similar to that described in Example 83, there were prepared compounds as shown in the following Table 4, and compounds of Examples 1–9, 11–19, 23–28, 30–43, 50–63, 65–72, 77–82, 98, 100–166, 168, 173, 175–180, 187–189, 190, 190a–190d, 191–225, 228–242, 246–248, 250, 252–259.

TABLE 4

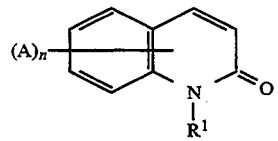

| Example No. | R¹ | n | A | Crystal form (Recrystallization solvent) | Melting point (°C.) | Salt |
| --- | --- | --- | --- | --- | --- | --- |
| 84 | H | 2 | 4-N⟨ ⟩<br>8-CH₃ | Light brown prism-like crystals (Methanol-diethyl ether) | 196–197.5 (decomp.) | Mono-Oxalate |
| 85 | CH₃ | 2 | 4-N⟨ ⟩<br>8-CH₃ | Light brown powdery substance (Acetone-deithyl ether) | 138–140 (decomp.) | HCl |

TABLE 4-continued

[Structure: carbostyril with (A)n substituents and N-R¹]

| Example No. | R¹ | n | A | Crystal form (Recrystallization solvent) | Melting point (°C.) | Salt |
|---|---|---|---|---|---|---|
| 86 | H | 2 | 4-N⟨pyrrolidinyl⟩, 8-F | White powdery substance (Ethanol-diethyl ether) | 244–254 (decomp.) | HCl |
| 87 | H | 2 | 4-N(C₂H₅)₂, 8-F | White powdery substance (Ethanol-diethyl ether) | 166–168 | HCl |
| 88 | H | 2 | 4-N⟨piperidinyl⟩-CH₂-phenyl, 8-F | Light brown needle-like crystals (Ethanol) | 232–233 | — |
| 89 | H | 2 | 4-N⟨piperazinyl⟩N—CH₃, 8-F | White powdery substance (Methanol-diethyl ether) | Over 300 | HCl |

EXAMPLE 90

To a solution prepared by 2.9 g of 3-amino-8-methyl-carbostyril, 3.5 ml of triethylamine in 50 ml of dichloromethane was added dropwise a solution prepared by 1.9 ml of chloroacetyl chloride in 10 ml of dichloromethane under ice-cooled condition. After the dropwise addition, the reaction mixture was stirred at room temperature for 30 minutes. Then the reaction mixture was concentrated by removing the solvent by evaporation under reduced pressure, the residue thus obtained was suspended in aceton and the suspension was poured in an ice-water. The crystals formed were collected by filtration, washed with water, dried, then recrystallized from acetone-water to obtain 3.6 g of 3-chloroacetylamino-8-methylcarbostyril. White powdery substance. Melting point: 271.5°–272° C. (decomposed).

By using suitable starting materials, and by using method similar to that described in Example 90, there were prepared compounds of Examples 20–22, 46–48, 64, 73–76, 99, 226, 227 and 243–245.

EXAMPLE 91

A suspension prepared by mixing 0.7 g of 3-chloroacetylamino-8-methylcarbostyril, 2.04 g of diethylamine, 1.16 ml of triethylamine in 30 ml of acetonitrile was refluxed by heating for 7.5 hours. The reaction mixture was poured in an ice-water, and the precipitate was collected by filtration, washed with water, and dried. Then the dried precipitate was dissolved in methanol, and converted into hydrochloride by using a concentrated hydrochloric acid-ethanol. Recrystallized from ethanol-water to obtain 0.52 g of 3-(2-diethylaminoacetyl)amino-8-methylcarbostyril hydrochloride. Light yellow powdery substance. Melting point: 250°–252° C. (decomposed).

By using suitable starting materials, and by using method similar to that described in Example 91, there were prepared compounds of Examples 20–22, 46–48, 243–245 and 64.

EXAMPLE 92

1.6 Grams of 3-amino-8-methyl-3,4-dihydrocarbostyril hydrochloride was suspended in 30 ml of acetone, then 2.6 g of ethyl iodide and 2.6 g of potassium carbonate were added thereto, next the mixture was placed in a sealed tube and reacted by heating at 120° C. for 10 hours. To the reaction mixture, was added dichloromethane-water, and the organic layer was collected by separation. The organic layer was washed with water, then dried with anhydrous sodium sulfate. The solvent was removed by evaporation, then the residue thus obtained was purified by a silica gel column chromatography (eluent: dichloromethane:methanol=100:1). Recrystallized from ethanol-diethyl ether to obtain 1.5 g of 3-diethylamino-8-methyl-3,4-dihydrocarbostyril hydrochloride. White powdery substance. Melting point: 231.5°–233° C.

By using suitable starting materials and by using method similar to that described in Example 92, there were prepared compounds of Examples 5–6, 8, 11, 14, 16, 19, 23, 25, 32, 37–42, 49–50, 53, 56, 59–60, 68–72, 77, 83, 98, 101, 104, 113, 120, 127, 137, 139–141, 143, 148, 178, 189, 190, 202, 211, 213, 219, 223, 224, 225, 230, 233, 240, 241 and 242.

EXAMPLE 93

A suspension prepared by mixing 1 g of 1-methyl-8-amino-3,4-dihydrocarbostyril, 1.35 g of 1,4-dibromobutane, 1.9 g of sodium iodide, 1.75 g of potassium carbonate in 10 ml of acetonitrile was refluxed by heating for 20 hours. Then to the reaction mixture was added dichloromethane-water, and the organic layer was collected by separation, washed with water, and dried with anhydrous sodium sulfate. Next, the solvent was removed by evaporation, and the residue thus obtained was purified by a silica gel column chromatography (eluent: dichloromethane:methanol=50:1). The purified product was dissolved in diethyl ether, and the desired product was converted into hydrochloride by using ethanol-concentrated hydrochloric acid, recrystallized from ethanol-diethyl ether to obtain 1.15 g of 1-methyl-8-pyrrolidino-3,4-dihydrocarbostyril hydrochloride. White powdery substance. Melting point: 174.5°–177° C.

By using suitable starting materials and by using method similar to that described in Example 93, there were prepared compounds of Examples 2, 4, 7, 12, 17–18, 26–28, 31, 34, 54–55, 57–58, 61–63, 65–67, 78–82, 84–85, 100, 102, 105–110, 112, 114–119, 121, 123–126, 128–132, 134–136, 138, 142, 144–147, 149–166, 168–173, 175–177, 180, 188, 190a–190d, 193–195, 197–201, 203–210, 212, 215–218, 220–222, 228–229, 231–232, 234–236, 246, 247, 248, 250, 252–259.

EXAMPLE 94

0.19 Gram of lithium aluminium hydride was suspended in 27 ml of dry tetrahydrofuran, then 0.9 g of 3-acetylamino-8-methylcarbostyril was added thereto, and the mixture was refluxed by heating under argon gas atmosphere for 2 hours. To the reaction mixture was added water, and extracted with chloroform. The chloroform extract was washed with water, and dried with anhydrous magnesium sulfate. After removal of the solvent by evaporation, the residue was purified by a silica gel column chromatography (eluent: dichloromethane:methanol=50:1). The desired product was converted into hydrochloride by using ethanol-concentrated hydrochloric acid, then recrystallized from ethanol to obtain 0.27 g of 3-ethylamino-8-methylcarbostyril hydrochloride. Light yellow needle-like crystals. Melting point: 230°–232° C.

By using suitable starting materials and by using method similar to that described in Example 94, there were prepared compounds of Examples 5, 6, 8, 9, 11, 14, 16, 19, 23, 25, 32, 37, 38, 39, 41, 49, 50, 53, 56, 59, 60, 68, 69, 70, 71, 72, 77, 87, 98, 101, 104, 113, 120, 127, 137, 139, 140, 141, 143, 148, 189, 202, 211, 213, 214, 219, 224, 230, 233, 240–242.

EXAMPLE 95

A suspension prepared by mixing 5.3 g of 8-methylcarbonyl-3-carbonylchloride, 1.7 g of sodium azide in acetonitrile was stirred at room temperature overnight. After removal of the solvent by evaporation, to the residue thus obtained was added chloroform, the insoluble matters were removed by filtration, the filtrate was washed with water and dried with anhydrous sodium sulfate. The solvent was removed by evaporation to obtain 0.9 g of 8-methylcarbostyril-3-carboxyazide.

NMR (CDCl$_3$) δ: 2.51 (3H, s); 7.19 (1H, t, J=7.5 Hz); 7.50 (1H, d, J=7.5 Hz); 7.55 (1H, d, J=7.5 Hz ); 8.65 (1H, s); 9.51 (1H, brs).

EXAMPLE 96

A solution of 0.9 g of 8-methylcarbostyril-3-carboxyazide in 20 ml of t-butyl alcohol was refluxed by heating for 3 hours. To the reaction mixture was added water, and the precipitate was collected by filtration, then to this precipitate was added 5 ml of concentrated hydrochloric acid and 20 ml of ethanol, and the mixture was refluxed by heating for 2 hours. The solvent was removed by evaporation, and the residue thus obtained was recrystallized from chloroform to obtain 0.53 g of 3-amino-8-methylcarbostyril. Light brown powdery substance. Melting point: 225°–260° C. (decomposed).

By using suitable starting materials and by using method similar to described in Example 96, there were prepared compounds of Examples 1, 3, 13, 15, 30, 33, 103 and 187.

EXAMPLE 97

Solution of 12.3 g of 3-diethylamino-8-methyl-3,4-dihydrocarbostyril hydrochloride in 100 ml of anhydrous dimethylformamide was added 1.9 g of 60%-sodium hydride, then this mixture was heated at 50° C. for 30 minutes. Next, to this reaction mixture was added dropwise 6.53 g of methyl iodide under ice-cooling condition. After the dropwise addition, the whole mixture was heated at 50° to 60° C. with stirring. The reaction mixture was poured in water, and was extracted with chloroform. The chloroform layer was washed with water, and dried. Chloroform was removed by evaporation, and the residue thus obtained was converted into a hydrochloride, and recrystallized from acetone-n-hexane to obtain 12 g of 1-methyl-3-diethylamino-8-methyl-3,4-dihydrocarbostyril hydrochloride. Light brown powdery substance. Melting point: 162.5°–164.5° C.

By using suitable starting materials and by using method similar to that described in Example 97, there were prepared compounds of Examples 18, 23–25, 85, 192, 220, 228–233, 250, 252–259.

EXAMPLES 98–108

By using suitable starting materials and by using method similar to that described in Example 1, there were prepared compounds as shown in the following Table 5.

EXAMPLES 109–180

By using suitable starting materials and by using method similar to that described in Example 35, there were prepared compounds as shown in the following Table 6.

TABLE 5

| Example No. | R¹ | n | A | Crystal form (Recrystallization solvent) | Melting point (°C.) | Salt |
|---|---|---|---|---|---|---|
| 98 | H | 2 | 6-N(C$_2$H$_5$)$_2$<br>8-F | Colorless needle-like crystals<br>(Ethanol) | 236.5–238 | HCl |
| 99 | H | 2 | 5-NHCOCH$_3$<br>8-F | White powdery substance<br>(Acetic acid-ethanol) | 182.5–185 | — |
| 100 | H | 2 | 5-N⟩piperidine<br>8-F | Light yellow needle-like crystals<br>(Ethanol-diethyl ether) | 218–222 | HCl |
| 101 | H | 2 | 5-N(C$_2$H$_5$)$_2$<br>8-F | Light green needle-like crystals<br>(Ethanol-diethyl ether) | 235–236.5 (decomp.) | HCl |
| 102 | H | 1 | 6-N⟩N—CH$_3$ | White powdery substance<br>(Ethanol-water) | 259–260.5 (decomp.) | HCl |
| 103 | H | 2 | 5-NH$_2$<br>8-F | Light brown powdery substance<br>(Methanol-water) | 280–282 (decomp.) | HCl |
| 104 | H | 2 | 3-N(CH$_2$)$_3$<br>8-CO$_2$H | Yellow powdery substance<br>(Acetone-water) | 194–196 | HCl |
| 105 | H | 2 | 5-N⟩NH<br>8-CH$_3$ | Colorless powder substance<br>(Ethanol-diethyl ether) | Over 300 | HCl |
| 106 | H | 2 | 5-N⟩N—CH$_3$<br>8-CH$_3$ | Colorless powdery substance<br>(Ethanol-diethyl ether) | 260–270 (decomp.) | HCl |
| 107 | H | 2 | 6-N⟩NH<br>8-CH$_3$ | White powdery substance<br>(Ethanol-diethyl ether) | Over 300 | HCl |
| 108 | H | 2 | 6-N⟩N—CH$_3$<br>8-CH$_3$ | White powdery substance<br>(Ethanol) | 270–275 | HCl |

TABLE 6

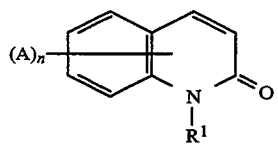

| Example No. | R[1] | n | A | Crystal form (Recrystallization solvent) | Melting point (C.) | Salt |
|---|---|---|---|---|---|---|
| 109 | H | 2 | 3-N(piperazine)N—(CH$_2$)$_3$C(=O)—C$_6$H$_4$—F<br>8-CH$_3$ | Light brawn powdery substance (Ethanol-Water) | 276–278 (decomp.) | HCl |
| 110 | H | 2 | 3-N(piperazine)N—(CH$_2$)$_3$—(4-pyridyl)<br>8-CH$_3$ | Light brawn powdery substance (Ethanol) | 261–263 (decomp.) | 2HCl |
| 111 | H | 2 | 3-N(pyridinium) Cl$^-$<br>8-CH$_3$ | Light brawn needle-like crystals (Isopropanol-water) | Over 300 | — |
| 112 | H | 2 | 3-N(piperazine)N—CH$_3$<br>8-F | Colorless powdery substance (Ethanol-water-diethyl) | Over 300 (decomp.) | HCl |
| 113 | H | 2 | 3-N(C$_2$H$_5$)$_2$<br>8-Cl | Colorless flake-like crystals (Ethanol) | 114–115 | — |
| 114 | H | 2 | 3-N(pyrrolidine)<br>8-Cl | Light brawn powdery substance (Ethanol) | 212–216 (decomp.) | — |
| 115 | H | 2 | 3-N(piperazine)N—CH$_3$<br>8-Cl | Colorless prism-like crystals (Ethanol-water) | Over 300 (decomp.) | HCl |
| 116 | H | 2 | 3-N(morpholine)O<br>8-CH$_3$ | Colorless needle-like crystals (Ethanol) | 235–236 | — |
| 117 | H | 2 | 3-N(thiomorpholine)S<br>8-CH$_3$ | Colorless prism-like crystals (Chloroform-n-hexane) | 240–241 | — |
| 118 | H | 2 | 3-N(piperidine) | Light brawn powdery substance (Ethanol-diethyl | 240–241 | — |

TABLE 6-continued

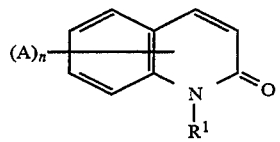

| Example No. | R¹ | n | A | Crystal form (Recrystallization solvent) | Melting point (C.) | Salt |
|---|---|---|---|---|---|---|
| 119 | H | 2 | 8-OH, 3-N(pyrrolidinyl) | Colorless powdery substance (Ethanol-diethyl ether) | 166–167 | HCl |
| 120 | H | 2 | 8-OCH₂CH=CH₂, 3-N(phenyl)(CH₂)₂N(C₂H₅)₂ | Light yellow powdery substance (Ethanol-diethyl ether) | 174–176 | Monooxalate |
| 121 | H | 2 | 8-CH₃, 3-N(piperazinyl)-N—CH₂CH₂OH | White powdery substance (Ethanol-water) | 267–270 (decomp.) | HCl |
| 122 | H | 2 | 8-CH₃, 3-N(bicyclic amine) | Light brawn powdery substance (Ethanol-diethyl ether) | 191–196 | HCl |
| 123 | H | 2 | 8-CH₃, 3-N(homopiperazinyl)NH | Light yellow powdery substance (Ethanol-water) | 278–280 | HCl |
| 124 | H | 2 | 8-CH₃, 3-N(piperazinyl)N—CH₂CH₃ | Colorless needle-like crystals (Ethanol) | 290–293 (decomp.) | HCl |
| 125 | H | 2 | 8-CH₃, 3-N(piperazinyl)N—CH₂CH₂CH₃ | Colorless needle-like crystals (Ethanol-water) | Over 300 Over 300 | HCl |
| 126 | H | 2 | 8-CH₃, 3-N(homopiperazinyl)N—CH₃ | Light yellow powdery substance (Ethanol-water) | 283–285 (decomp.) | HCl |

TABLE 6-continued

| Example No. | R¹ | n | A | Crystal form (Recrystallization solvent) | Melting point (C.) | Salt |
|---|---|---|---|---|---|---|
| 127 | H | 2 | 3-N(CH₃)(CH₂)₂-C₆H₃(OCH₃)₂; 8-F | Light yellow needle-like crystals (Ethanol-diethyl-ether) | 134–135.5 | Fumarate |
| 128 | H | 2 | 3-N-pyrrolidinyl-CON(C₂H₅)₂; 8-F | Colorless needle-like crystals (Diethyl ether-n-hexane) | 133–135 | — |
| 129 | H | 2 | 3-N-piperazinyl-N—CH(CH₃)₂; 8-CH₃ | White powdery substance (Ethanol) | 240–243 (decomp.) | HCl |
| 130 | H | 2 | 3-N-piperazinyl-NCH₂CH₂CH₂CH₃; 8-CH₃ | Colorless needle-like crystals (Ethanol) | 295–297 (decomp.) | HCl |
| 131 | H | 2 | 3-N-piperazinyl-N—CH₂C≡CH; 8-CH₃ | Light brawn needle-like crystals (Ethanol-water) | 247–249 (decomp.) | HCl |
| 132 | H | 2 | 3-N-piperazinyl-NCH₂COCH₃; 8-CH₃ | Colorless needle-like crystals (Ethanol-water) | 258–263 (decomp.) | HCl |
| 133 | H | 2 | 3-N-indolinyl; 8-CH₃ | Yellow needle-like crystals (Ethyl acetate) | 221–223 | — |
| 134 | H | 2 | 3-N-piperazinyl-N—CH₂CF₃; 8-CH₃ | Colorless needle-like crystals (Ethanol) | 213–215 | HCl |

TABLE 6-continued

| Example No. | R¹ | n | A | Crystal form (Recrystallization solvent) | Melting point (C.) | Salt |
|---|---|---|---|---|---|---|
| 135 | H | 1 | 3-N(NCH₃ piperazine) | Colorless needle-like crystals (Ethanol) | 295–297 (decomp.) | HCl |
| 136 | H | 2 | 3-N(N—COOCH₂Ph piperazine) | Colorless needle-like crystals (Ethanol) | 148–150 | — |
| 137 | H | 2 | 8-CH₃<br>3-N(C₂H₅)₂<br>8-OH | Colorless powdery substance (Ethanol-diisopropyl ether) | 160–164 | HCl |
| 138 | H | 2 | 3-N(piperidine) | White powdery substance (Ethanol-diethyl ether) | 251–253 | HCl |
| 139 | H | 2 | 8-CH₃<br>3-N(C₂H₅)₂<br>8-OCH₂CH=CH₂ | Colorless powdery substance (Ethanol-diethyl ether) | 168.5–171.5 | HCl |
| 140 | H | 2 | 3-N(C₂H₅)₂<br>8-OCH₂COCH₃ | Light brawn powdery substance (Ethanol-diethyl ether) | 205–210 | HCl |
| 141 | H | 2 | 3-N(C₂H₅)₂<br>8-O—CH(CH₃)₂ | Colorless powdery substance (Ethanol-diethyl ether) | 167–170 (decomp.) | HCl |
| 142 | H | 2 | 3-N(pyrrolidine-CH₂N(C₂H₅)₂) | NMR¹⁾ | | HCl |
| 143 | H | 2 | 8-CH₃<br>3-N(C₂H₅)₂<br>8-CF₃ | Yellow powdery substance (n-Hexane) | 205–210 | Fumarate |
| 144 | H | 2 | 3-N-cyclopentyl<br>8-CF₃ | Colorless powdery substance (Ethanol-diethyl ether) | 170–176 | HCl |
| 145 | H | 2 | 3-N(NCH₃ piperazine)<br>8-CF₃ | Colorless prism-like crystals (Ethanol-water) | Over 300 (decomp.) | HCl |

TABLE 6-continued

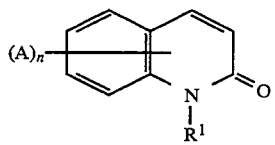

| Example No. | R¹ | n | A | Crystal form (Recrystallization solvent) | Melting point (C.) | Salt |
|---|---|---|---|---|---|---|
| 146 | H | 2 | 3-N(piperazine)N—CH₃<br>8-OCH₂-phenyl | Colorless needle-like<br>(Ethanol) | 235–238<br>(decomp.) | HCl |
| 147 | H | 2 | 3-N(piperazine)N—CH₃<br>8-C₂H₅ | Colorless prism-like crystals<br>(Ethanol-water) | Over 300<br>(decomp.) | HCl |
| 148 | H | 2 | 3-N(C₂H₅)₂<br>8-C₂H₅ | Light brawn powdery substance<br>(Ethanol-diethyl ether) | 200–202<br>(decomp.) | HCl |
| 149 | H | 2 | 3-N(pyrrolidine)<br>8-C₂H₅ | Light yellow powdery substance<br>(Ethanol-diethyl ether) | 195–199<br>(decomp.) | |
| 150 | H | 2 | 3-N(bicyclic amine)<br>8-C₂H₅ | Light yellow powdery substance<br>(Ethanol-diethyl ether) | 191–193.5<br>(decomp.) | Fumarate |
| 151 | H | 2 | 3-N(bicyclic amine)<br>8-CH₃ | Light brawn needle-like crystals<br>(Ethanol) | 160–165<br>(decomp.) | Mono-oxalate |
| 152 | H | 2 | 3-N(morpholine bicyclic)<br>8-CH₃ | Light pink powdery substance<br>(Ethanol) | 200–210<br>(decomp.) | HCl |

TABLE 6-continued

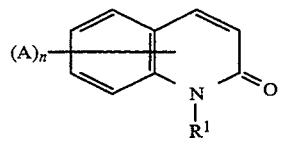

| Example No. | R¹ | n | A | Crystal form (Recrystallization solvent) | Melting point (°C.) | Salt |
|---|---|---|---|---|---|---|
| 153 | H | 2 | 3-N⟨piperidine with N-CH₃ bridged ring⟩ 8-CH₃ | Light yellow powdery substance (Methanol-water) | 203–205 (decomp.) | Di-oxalate |
| 154 | H | 2 | 3-N⟨⟩N—CH₃ with CH₃ 8-CH₃ | White powdery substance (Ethanol-diethyl ether) | 286–288 (decomp.) | HCl |
| 156 | H | 2 | 3-N⟨⟩N—CH₃ CH₃ 8-CH₃ | NMR[2)] | | HCl |
| 157 | H | 2 | 3-N⟨⟩N—cyclohexyl 8-CH₃ | Colorless needle-line crystals (Ethanol-water) | Over 300 | HCl |
| 158 | H | 2 | 3-N⟨⟩N—CH₂CON⟨⟩ 8-CH₃ | Colorless needle-like crystals (Ethanol-diethyl ether) | 252–253 (decomp.) | HCl |
| 159 | H | 2 | 3-N⟨⟩N—CH₂CH₂N⟨⟩ 8-CH₃ | Yellow needle-like crystals (Ethanol-water) | Over 300 | 2HCl |
| 160 | H | 2 | 3-N⟨⟩N—CH₂CON⟨⟩O 8-CH₃ | Colorless needle-like crystals (Ethanol) | 264–265 (decomp.) | HCl |
| 161 | H | 2 | 3-N⟨⟩N—CH₂CH₂N⟨⟩O 8-CH₃ | Light yellow needle-like crystals (Ethanol-water) | Over 300 | 2HCl |

TABLE 6-continued

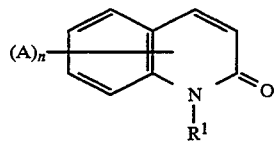

| Example No. | R¹ | n | A | Crystal form (Recrystallization solvent) | Melting point (°C.) | Salt |
|---|---|---|---|---|---|---|
| 162 | H | 2 | 3-N(CH₂CH₂)₂N-morpholine; 8-CH₃ | Colorless needle-like crystals (Ethanol-water) | 283–285 (decomp.) | HCl |
| 163 | H | 2 | 3-N(CH₂CH₂)₂N(CH₃)CH₂CH₂-(3,4-dimethoxyphenyl); 8-CH₃ | Colorless needle-like crystals (Ethanol-diethyl ether) | 113–114 | — |
| 164 | H | 2 | 3-N(CH₂CH₂)₂N-pyrrolidine; 8-CH₃ | White powder substance (Ethanol) | 297–299 (decomp.) | Hcl |
| 165 | H | 2 | 3-N(CH₂CH₂)₂N—N-CH₃; 8-CH₃ | White powdery substance (Ethanol-water) | 280–282 (decomp.) | 2HCl |
| 166 | H | 2 | 3-N(CH₂CH₂)₂N—CH₂-(2-thienyl); 8-CH₃ | Light yellow powdery substance (Ethanol-diethyl ether) | 213–216 (decomp.) | HCl |
| 167 | H | 2 | 3-(2-pyridyl); 8-CH₃ | Yellow needle-like crystals (Methanol) | 263–266 | HCl |
| 168 | H | 2 | 3-N(CH₂CH₂)₂N—CH₃; 8-OH | Light brawn powdery substance (Ethanol-water) | 260–270 | HCl |

TABLE 6-continued

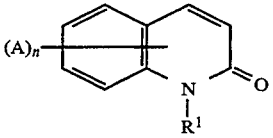

| Example No. | R¹ | n | A | Crystal form (Recrystallization solvent) | Melting point (C.) | Salt |
|---|---|---|---|---|---|---|
| 169 | H | 2 | 3-N(piperazine)N—CH₂CH(CH₃)₂<br>8-CH₃ | Colorless needle-like crystals (Ethanol-water) | 286–289 (decomp.) | HCl |
| 170 | H | 2 | 3-N(piperazine)N(piperidine)<br>8-CH₃ | Light brawn prism-line crystals (Ethanol-water) | Over 300 | HCl |
| 171 | H | 2 | 3-N(piperazine)N—CH₂-cyclopropyl<br>8-CH₃ | Colorless prism-like crystals (Ethanol-water) | 282–284 | HCl |
| 172 | H | 2 | 3-N(piperazine)N—CH₂CH₂—C₆H₃(OCH₃)₂<br>8-CH₃ | Colorless needle-like like crystals (Ethanol-water) | 255–258 (decomp.) | HCl |
| 173 | H | 2 | 3-N(piperazine)N—(CH₂)₅CH₃<br>8-CH₃ | White powdery substance (Ethanol) | 264–264.5 (decomp.) | HCl |
| 174 | H | 2 | 3-(spiro pyrrolidine)N<br>8-CH₃ | Colorless needle like crystals (Ethanol-diethyl ether) | Over 300 | HCl |
| 175 | H | 2 | 3-N(piperazine)N—CH₂CH=C(CH₃)₂<br>8-CH₃ | White powdery substance (Ethanol-diethyl ether) | 254–256 (decomp.) | HCl |
| 176 | H | 2 | 3-N(piperazine)N—CH₃<br>8-OCH₂CON(C₂H₅)₂ | White powdery substance (Ethanol-diethyl ether) N.M.R³⁾ | 130–133 | HCl |

TABLE 6-continued

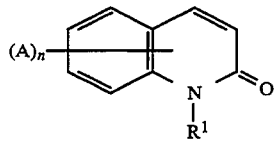

| Example No. | R¹ | n | A | Crystal form (Recrystallization solvent) | Melting point (°C.) | Salt |
|---|---|---|---|---|---|---|
| 177 | H | 2 | 3-N⌒N—(CH₂)₇CH₃ ⌣ 8-CH₃ | White powdery substance (Ethanol) | 246–247 (decomp.) | HCl |
| 178 | H | 2 | 3-N(CH₂CH=CH₂)₂ 8-CH₃ | Colorless prism-like crystals (Ethanol-diethyl ether) | 180.5 | HCl |
| 179 | H | 2 | 3-N⌒N—(CH₂)₉CH₃ ⌣ 8-CH₃ | Light brawn powdery substance (Isopropanol) | 240–242 (decomp.) | HCl |
| 180 | H | 2 | 3-N⌒N—CH₂—⟨O⟩ ⌣ 8-CH₃ | White powdery substance (Ethanol-diethyl ether) | 258–259 (decomp.) | HCl |

¹⁾NMR: δ(DMSO-d₆): 1.29(6H, t; J=5.5Hz), 1.90–2.14(4H, m), 2.96–3.69(8H, m), 4.76–4.89(1H, m), 7.01–7.18(3H, m), 7.40(1H, d; J=7Hz), 10.29(1H, br s), 11.19 (1H, s)
²⁾NMR: δ(DMSO-d₆): 0.99(3H, d; J=6Hz), 1.19(3H, d; J=6Hz), 2.44(3H, s), 2.73–2.98(4H, m), 3.03–3.39(2H, m), 4.86–5.01(1H, m) 7.05–7.59(4H, m), 10.66(1H, br s), 10.99(1H, s), 11.05(1H, s)
³⁾NMR: δ(DMSO-d₆): 1.07(3H, t, J=7Hz, CH₂CH₃), 1.14(3H, t, J=7Hz, CH₂CH₃), 2.84(3H, s, N—CH₃), 2.90–3.60(10H, m, CH₂ bonded at α-position of the nitrogen atom), 3.90–4.10(2H, m, CH₂ bonded at α-position of the nitrogen atom), 4.96*(2H, s, —OCH₂CO—), 6.99(1H, d, J=7Hz, an aromaticH), 7.10(1H, t, J=7Hz, an aromatic H), 7.25(1H, d, J=7Hz, an aromatic H), 7.29(1H, s, H bonded at 4-position in the carbostyril skeleton), 10.73(1H, brs, NH), 10.97(1H, brs, NH(the proton of the hydrochloride))

EXAMPLE 181

2.0 Grams of 3-[4-(1-pyrrolidinylcarbonylmethyl)-1-piperazinyl]-8-methylcarbostyril hydrochloride was suspended in 20 ml of tetrahydrofuran, to this suspension was added dropwise a solution of 0.32 g of lithium aluminium hydride in 20 ml of tetrahydrofuran under nitrogen gas stream with stirring. This reaction mixture was stirred at the same temperature for 30 minutes, then the reaction mixture was refluxed by heating on a oil bath for 2 hours. To the reaction mixture was added water and methylene chloride and filtered with Celite (a trademark for diatomaceous earth product, manufactured by Johns Manville Sales Corp., U.S.A.). The filtrate was extracted with methylene chloride, washed with an aqueous solution saturated with sodium chloride, and dried with anhydrous sodium sulfate, then concentrated by removing the solvent under reduced pressure, the residue thus obtained was purified by a silica gel column chromatography (eluent: methylene chloride:methanol=10:1). The desired product was converted into dihydrochloride by using ethanol-HCl, then recrystallized from ethanol-water to obtain 1.15 g of 3-{4-[2-(1-pyrrolidinyl)ethyl]-1-piperazinyl}-8-methylcarbostyril dihydrochloride. Light yellow needle-like crystals. Melting point: over 300° C.

By using suitable starting materials and by using method similar to that described in Example 181, there were prepared compounds 79, 142 and 161.

EXAMPLE 182 a) 5.1 Grams of 2-methyl-3-aminoacetanilide was dissolved in 150 ml of acetone, to this solution was added dropwise a solution of 5.7 g of cinnamoyl chloride in 30 ml of acetone and a solution of 5.2 g of potassium carbonate in 50 ml of water under ice-cooled condition with stirring. The reaction mixture was stirred at the same temperature for 2 hours, then the reaction mixture was poured in an ice-water. The precipitate was collected by filtration, washed with water, dried to obtain 8.64 g of N-(3-acetylamino-2-methyl)phenylcinnamoylamide.

NMR (DMSO-d₆) δ: 2.10 (3H, s); 2.14 (3H, s); 6.92 (1H, d, J=15 Hz); 7.05–7.65 (8H, m); 7.60 (1H, d, J=15 Hz); 9.28 (1H, brs); 9.44 (1H, brs).

b) 24 Grams of aluminium chloride was suspended in 25 ml of chlorobenzene, to this suspension was added 8 g of N-(3-acetylamino-2-methyl)phenylcinnamoylamide, and the mixture was heated at 110° to 120° C. for 5 hours with stirring. The reaction mixture was poured in an ice-water, and the precipitate was collected by filtration. Then the precipitate was washed with n-hexane, diethyl ether and water in this order, and recrystallized from dimethylformamide to obtain 4.09 g of 7-acetylamino-8-methylcarbostyril.

NMR (DMSO-d₆) δ: 2.10 (3H, s); 2.30 (3H, s); 6.45 (1H, d, J=9 Hz); 7.23 (1H, d, J=8 Hz); 7.47 (1H, d, J=8 Hz); 7.85 (1H, d, J=9Hz); 9.60 (1H, brs).

EXAMPLE 183

To 5 g of 7-acetylamino-8-methylcarbostyril was added 60 ml of 20% hydrochloric acid, and the mixture was heated at 11020 to 120° C. on an oil bath with stirring. After heating for 4 hours, the solvent was removed by evaporation under pressure, then the residue obtained was washed with hot-methanol, dried, next recrystallized from methanol-water to obtain 5.25 g of 7-amino-8-methylcarbostyril hydrochloride. Light yellow needle-like crystals. Melting point: 290°–293° C. (decomposed).

By using suitable starting materials and by using method similar to that described in Example 182, there were prepared compounds of Examples 1, 3, 13, 15, 30, 33, 45 and 103.

EXAMPLE 184

To 2.07 g of 2-methyl-3-(β-bromoacryloyl-)aminoacetanilide was added 10 ml of concentrated hydrochloric acid and heated at 70° C. The reaction mixture was poured in ice-water, then the resinous substance was removed, and the remainder was neutralized with 10N-NaOH. The precipitate crystals were collected by filtration, and washed with water, recrystallized from dimethylformamide to obtain 0.75 g of 7-acetylamino-8-methylcarbostyril.

NMR (DMSO-$d_6$) δ: 2.10 (3H, s); 2.30 (3H, s); 6.45 (1H, d, J=9 Hz); 7.23 (1H, d, J=8 Hz); 7.47 (1H, d, J=8 Hz); 7.85 (1H, d, J=9 Hz); 9.60 (1H, brs).

EXAMPLE 185

A solution of 2.15 g of 2-methyl-3-(β,β-diethoxypropionyl)amino-acetanilide in 3 ml of acetone was added dropwise to 20 ml of concentrated hydrochloric acid at 60° C. with stirring. The reaction was continued for 30 minutes, the solvent was removed by evaporation, and the residue was neutralized with 10N-NaOH. The crystals precipitated were collected by filtration, washed with water, then recrystallized from dimethylformamide to obtain 1.25 g of 7-acetylamino-8-methylcarbostyril.

NMR (DMSO-$d_6$) δ: 2.10 (3H, s); 2.30 (3H, s); 6.45 (1H, d, J=9 Hz); 7.23 (1H, d, J=8 Hz); 7.47 (1H, d, J=8 Hz); 7.85 (1H, d, J=9 Hz); 9.60 (1H, brs).

EXAMPLE 186 a) 10.7 Grams of 2-methyl-3-aminoacetanilide was dissolved in 150 ml of dimethyl sulfoxide, then 3.12 g of sodium hydride (50% suspended in oil) was added gradually. The reaction mixture was stirred at room temperature for 30 minutes, then 6.4 g of ethyl propionate was added gradually. The whole mixture was stirred at room temperature for 12 hours. The reaction mixture was poured in a large amount of an aqueous solution saturated with sodium chloride, then extracted with chloroform. The chloroform layer was washed with an aqueous solution saturated with sodium chloride, then chloroform was removed by evaporation under reduced pressure to obtain 3-ethynylcarbonylamino-2-methylacetanilide.

b) The 3-ethynylcarbonylamino-2-methylacetanilide obtained in the above-mentioned step (a) was dissolved in 5 ml of ethanol, then this solution was added dropwise gradually to concentrated sulfuric acid at 60° to 70° C. under stirring condition. After finished the dropwise addition, the reaction mixture was further stirred for 30 minutes. The reaction mixture was poured in ice, and neutralized with 10N-NaOH, and crystals precipitated were collected by filtration. Recrystallized from dimethylformamide to obtain 8.85 g of 7-acetylamino-8-methylcarbostyril.

NMR (DMSO-$d_6$) δ: 2.10 (3H, s); 2.30 (3H, s); 6.45 (1H, d, J=9 Hz); 7.23 (1H, d, J=8 Hz); 7.47 (1H, d, J=8 Hz); 7.85 (1H, d, J=9 Hz); 9.60 (1H, brs).

By using suitable starting material and by using methods similar to those described in Examples 182, 183–186, there were prepared compounds of Examples 35–89, 95, 109–180, 191–233 and 240–245, and compounds shown in the following Table 7.

TABLE 7

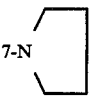

| Example No. | $R^1$ | n | A | Crystal form (Recrystallization solvent) | Melting point (°C.) | Salt |
|---|---|---|---|---|---|---|
| 187 | H | 2 | 7-$NH_2$<br>8-$CH_3$ | Light yellow needle-like crystals (Methanol-water) | 290–293 (decomp.) | HCl |
| 188 | H | 2 | 7-N⟨  ⟩<br>8-$CH_3$ | Light yellow needle-like crystals (Ethanol) | 232–235 | HCl |
| 189 | H | 2 | 7-$NHC_2H_5$<br>8-$CH_3$ | Yellow needle-like crystals (Ethanol) | 239–240.5 | HCl |

EXAMPLE 190

By using suitable starting materials and by method similar to that described in Example 1, there were prepared compounds shown in the following Table 8.

TABLE 8

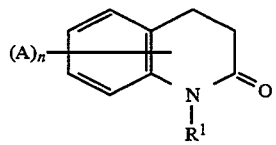

| Example No. | R¹ | n | A | Crystal form (Recrystallization solvent) | Melting point (°C.) | Salt |
|---|---|---|---|---|---|---|
| 190 | H | 2 | 3-NH–(imidazole); 8-CH₃ | White powdery substance (Ethanol-diethyl ether) | 210–220 | HCl |
| 190a | H | 1 | 6-N(piperidinyl)–NH₂ | White powdery substance (Methanol) | 292–296 (decomp.) | 2HCl. ½H₂O |
| 190b | H | 1 | 6-N(piperidinyl)–N(H)CH₃ | Colorless needle-like crystals (Methanol-diethyl ether) | 283–287 (decomp.) | 2HCl. H₂O |
| 190c | H | 1 | 6-N(piperidinyl)–N(H)CH₂Ph | Colorless needle-like crystals (Ethanol-water) | 262–266 (decomp.) | 2HCl. H₂O |
| 190d | H | 1 | 6-N(piperidinyl)–N(CH₃)CH₂Ph | Colorless needle-like crystals (Ethanol-water) | 249–252 | 2HCl |

EXAMPLES 191–233

By using suitable starting materials and by using method similar to that described in Example 35, there were prepared compounds as shown in the following Table 9.

EXAMPLES 234–239

By using suitable starting materials and by using method similar to that described in Example 1, there were prepared compounds as shown in the following Table 10.

EXAMPLES 240–245

By using suitable starting materials and by using method similar to that described in Example 35, there were prepared compounds as shown in the following Table 11.

EXAMPLES 246–248

By using suitable starting materials and by using method similar to those described in Examples 182, 183–186, there were prepared compounds as shown in the following Table 12.

EXAMPLE 249

By using suitable starting material and by using method similar to that of Example 1, there were prepared compound as shown in the following Table 13.

EXAMPLES 250–259

By using suitable starting materials and by using methods similar to those described in Examples 182, 183–186, there were prepared compounds as shown in the following Table 14.

TABLE 9

Structure: quinolin-2(1H)-one with (A)$_n$ substituents and N-R$^1$

| Example No. | R$^1$ | n | A | Crystal form (Recrystallization solvent) | Melting point (°C.) | Salt |
|---|---|---|---|---|---|---|
| 191 | H | 2 | 3-N(pyrrol-1-yl with =N); 8-CH$_3$ | White powdery substance (Ethanol-water) | Over 300° C. | HCl |
| 192 | C$_2$H$_5$ | 2 | 3-N(pyrrolyl-N$^+$—C$_2$H$_5$) Cl$^-$; 8-CH$_3$ | Light yellow powdery substance (Ethanol-diethyl ether) | 290–294 (decomp.) | — |
| 193 | H | 2 | 3-N(piperazin-N—CH$_2$-tetrahydrofuran-2-yl); 8-CH$_3$ | White powdery substance (Ethanol-diethyl ether) | 258–259 (decomp.) | HCl |
| 194 | H | 2 | 3-N(piperazin-N—CH$_2$-cyclohexyl); 8-CH$_3$ | Colorless needle-like crystals (Ethanol) | 273–274 (decomp.) | HCl |
| 195 | H | 2 | 3-N(piperazin-N—CH$_2$CHCH$_3$ with OCH$_3$); 8-CH$_3$ | White powdery substance (Ethanol-diethyl ether) | 274–275 (decomp.) | HCl |
| 196 | H | 2 | 3-N(imidazolyl with CH$_2$N(C$_2$H$_5$)); 8-CH$_3$ | Colorless prism-like crystals (Ethanol-diethyl ether) | 123–124 | Oxalate |
| 197 | H | 2 | 3-N(piperazin-N—(CH$_2$)$_4$CH$_3$); 8-CH$_3$ | White powdery substance (Ethanol) | 271–272 (decomp.) | HCl |
| 198 | H | 2 | 3-N(morpholinyl-CH$_2$—N-pyrrolidinyl); 8-CH$_3$ | Light brown powdery substance (Ethanol-diethyl ether) | 256–258 (decomp.) | HCl |

TABLE 9-continued

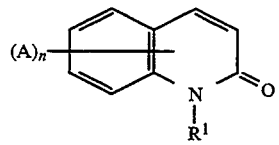

| Example No. | R¹ | n | A | Crystal form (Recrystallization solvent) | Melting point (°C.) | Salt |
|---|---|---|---|---|---|---|
| 199 | H | 2 | 3-N(CH₂-N(piperazine)-CH₃)(morpholine), 8-CH₃ | White powdery substance (Ethanol-water) | 273–275 (decomp.) | 2HCl |
| 200 | H | 2 | 3-N(morpholine)(CH₂-N(morpholine)), 8-CH₃ | Light pink powdery substance (Methanol-diethyl ether) | 282–283 (decomp.) | HCl |
| 201 | H | 3 | 3-N(piperazine)-CH₃, 6,8-diCH₃ | Colorless prism-like crystals (Ethanol-water) | Over 300 (decomp.) | HCl |
| 202 | H | 3 | 3-N(C₂H₅)₂, 6,8-diCH₃ | White powdery substance (Ethanol-diethyl ether) | 205–206.5 | HCl |
| 203 | H | 3 | 3-N(pyrrolidine), 6,8-diCH₃ | White powdery substance (Ethanol) | 215–219 | HCl |
| 204 | H | 2 | 3-N(piperazine)-N(cyclopropyl), 8-CH₃ | Colorless needle-like crystals (Ethanol) | 235–238 (decomp.) | HCl |
| 205 | H | 2 | 3-N(piperazine)-N-CH₂CH₂OCH₃, 8-CH₃ | White powdery substance (Ethanol-water) | 250–252 (decomp.) | HCl |
| 206 | H | 2 | 3-N(piperidine)-N(C₂H₅)₂, 8-CH₃ | White powdery substance (Ethanol-water) | 285–286 (decomp.) | HCl |

TABLE 9-continued

| Example No. | R¹ | n | A | Crystal form (Recrystallization solvent) | Melting point (°C.) | Salt |
|---|---|---|---|---|---|---|
| 207 | H | 2 | 3-N(morpholine-CH₂-N(3,5-diCH₃-piperidine)), 8-CH₃ | Light brawn needle-like crystals (Ethanol-n-hexane) | Over 300 | HCl |
| 208 | H | 2 | 3-N(piperidine-N-piperidine), 8-CH₃ | Colorless needle-like (Ethanol-water) | 288–290 (decomp.) | HCl |
| 209 | H | 3 | 3-N(piperazine-N-CH₃), 5,8-diCH₃ | White powdery substance (Ethanol-water) | Over 300 (decomp.) | HCl |
| 210 | H | 3 | 3-N(pyrrolidine), 5,8-diCH₃ | Yellow powdery substance (Ethanol) | 216–220 (decomp.) | HCl |
| 211 | H | 3 | 3-N(C₂H₅)₂, 5,8-diCH₃ | White powdery substance (Ethanol-diethyl ether) | 194–196 (decomp.) | HCl |
| 212 | H | 2 | 3-N(piperazine-N-CH(C₆H₅)₂), 8-CH₃ | Colorless prism-like crystals (Methanol) | 281–282 (decomp.) | HCl |
| 213 | H | 2 | 3-N(CH₃)(CH₂C₆H₅), 8-CH₃ | Colorless prism-like crystals (Ethanol-diethyl ether) | 190–193 | HCl |
| 214 | H | 2 | 3-N(C₂H₅)(CH₂C₆H₅) | Colorless needle-like crystals | 192–194 | HCl |

TABLE 9-continued

| Example No. | R¹ | n | A | Crystal form (Recrystallization solvent) | Melting point (°C.) | Salt |
|---|---|---|---|---|---|---|
| 215 | H | 2 | 8-CH₃<br>3-N(piperazinyl)—CH₂CH₂CH₃ | Colorless prism-like crystals (Ethyl acetate-n-hexane) | 154–155 | — |
| 216 | H | 2 | 8-C₂H₅<br>3-N(piperazinyl)—CH₂CH(CH₃)CH₃ | Colorless needle-like crystals (Ethyl acetate-n-hexane) | 175.5–176.5 | — |
| 217 | H | 3 | 8-C₂H₅<br>3-N(piperidinyl) | Light yellow powdery substance (Ethanol-water) | 210–213 (decomp.) | HCl |
| 218 | H | 3 | 6-OCH₃, 8-CH₃<br>3-N(piperazinyl)—CH₃ | White powdery substance (Ethanol-water) | 290–295 (decomp.) | HCl |
| 219 | H | 3 | 6-OCH₃, 8-CH₃<br>3-N(C₂H₅)₂<br>6-OCH₃, 8-CH₃ | Light yellow powdery substance (Ethanol-diethyl ether) | 195–197 | HCl |
| 220 | CH₃ | 2 | 3-N(pyrrolidinyl) | Orange needle-like crystals (n-Hexane) | 77.5–78.5 | — |
| 221 | H | 2 | 8-CH₃<br>3-N(3,5-dimethylpiperidinyl) | Light yellow needle-like crystals (Ethanol) | 216–219 | |
| 222 | H | 3 | 8-CH₃<br>3-N(piperazinyl)—CH₃<br>4-(phenyl),<br>8-CH₃ | Colorless needle-like crystals (Ethanol-water) | Over 300 | HCl |

TABLE 9-continued

[Structure: quinolin-2(1H)-one with (A)ₙ substituents and R¹ on nitrogen]

| Example No. | R¹ | n | A | Crystal form (Recrystallization solvent) | Melting point (°C.) | Salt |
|---|---|---|---|---|---|---|
| 223 | H | 2 | 3-N(CH₂-phenyl)(phenyl); 8-CH₃ | Colorless needle-like crystals | 213–214.5 | HCl |
| 224 | H | 2 | 3-NHCH₃; 8-CH₃ | Light yellow needle-like crystals (Ethanol-water) | 209–212 | — |
| 225 | H | 2 | 3-NH-phenyl; 8-CH₃ | Colorless needle-like crystals (Ethanol) | 191.5–193.5 | — |
| 226 | H | 2 | 3-N(CH₃)(COCH₂Cl); 8-CH₃ | White powdery substance (Ethyl acetate-n-hexane) | 188–189 (decomp.) | — |
| 227 | H | 2 | 3-N(C₂H₅)(COCH₂Cl); 8-CH₃ | Colorless needle-like crystals (Ethyl acetate-n-hexane) | 189–190.5 (decomp.) | — |
| 228 | C₂H₅ | 2 | 3-N(4-methylpiperazin-1-yl); 8-CH₃ | Colorless needle-like crystals (Ethanol-diethyl ether) | 185–190 (decomp.) | Oxalate |
| 229 | C₂H₅ | 2 | 3-N(pyrrolidin-1-yl); 8-CH₃ | Brawn prism-like crystals (n-Hexane) | 89–90 | — |
| 230 | C₂H₅ | 2 | 3-N(C₂H₅)₂; 8-CH₃ | Violet needle-like crystals (Ethanol-n-hexane) | 102–104 | Di-oxalate |
| 231 | CH₂-phenyl | 2 | 3-N(4-methylpiperazin-1-yl); 8-CH₃ | Colorless needle-like crystals (Ethanol-water-diethyl ether) | 219 (decomp.) | Oxalate |
| 232 | CH₂-phenyl | 2 | 3-N(pyrrolidin-1-yl); 8-CH₃ | Colorless needle-like crystals (Ethanol-n-hexane) | 107–108 | — |

TABLE 9-continued

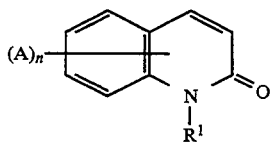

| Example No. | R¹ | n | A | Crystal form (Recrystallization solvent) | Melting point (°C.) | Salt |
|---|---|---|---|---|---|---|
| 233 | CH₂-C₆H₅ | 2 | 3-N(C₂H₅)₂ <br> 8-CH₃ | Brawn powdery substance | 99–103 | Oxalate |

TABLE 10

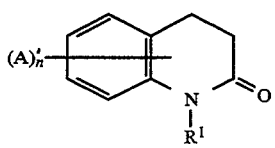

| Example No. | R¹ | n | A | Crystal form (Recrystallization solvent) | Melting point (C.°) | Salt |
|---|---|---|---|---|---|---|
| 234 | H | 1 | 6-N(piperidinyl-piperidine) | White powdery substance (Ethanol-water) | 275–278 (decomp.) | 2 HCl |
| 235 | H | 1 | 6-N(pyrrolidinyl-morpholine) | Light brawn powdery substance (Ethanol-diethyl ether) | 200–201.5 (decomp.) | — |
| 236 | H | 1 | 6-N(morpholinyl-CH₂-pyrrolidine) | White powdery substance (Diethyl ether-n-hexane) | 126.5–128 (decomp.) | — |
| 237 | H | 2 | 3-pyridyl, 8-CH₃ | Light yellow needle-like crystals (Ethanol-water-diethyl ether) | 232–235 | — |
| 238 | H | 2 | 3-piperidinyl (NH), 8-CH₃ | Colorless needle-like crystals (Methanol-diethyl ether) | 271–272 | HCl |
| 239 | H | 2 | 3-(1-methylpiperidinyl) | Colorless needle-like crystals (Ethanol-diethyl ether) | 142–143 | Oxalate |

TABLE 10-continued

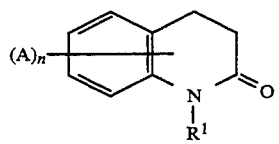

| Example No. | R¹ | n | A | Crystal form (Recrystallization solvent) | Melting point (C.°) | Salt |
|---|---|---|---|---|---|---|
| | | | 8-CH₃ | | | |

TABLE 11

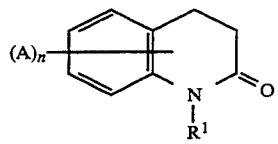

| Example No. | R¹ | n | A | Crystal form (Recrystallization solvent) | Melting point (C.°) | Salt |
|---|---|---|---|---|---|---|
| 240 | H | 2 | 3-N(C₂H₅)-(piperidine-N-CH₂-phenyl); 8-CH₃ | Light yellow needle-like (Ethanol-water-diethyl ether) | 223–225 (decomp.) | Fumarate |
| 241 | H | 2 | 3-N(C₂H₅)-CH₂-(morpholine-N-CH₂-phenyl); 8-CH₃ | Light yellow powdery substance | 110–115 (decomp.) | Oxalate |
| 242 | H | 2 | 3-N(C₂H₅)-CHCH₂O-(2,6-(H₃C)₂-phenyl); 8-CH₃ | Light yellow powdery substance (Ethanol-n-hexane) | 184–185 | HCl |
| 243 | H | 2 | 3-N(CH₃)-COCH₂N(C₂H₅)₂; 8-CH₃ | Light brawn plate-like crystals (Ethanol-diethyl ether) | 225–226 | HCl |
| 244 | H | 2 | 3-N(C₂H₅)-COCH₂N(C₂H₅)₂; 8-CH₃ | Light yellow granular crystals (Ethanol-diethyl ether) | 225.5–226 | HCl |
| 245 | H | 2 | 3-N(phenyl)-COCH₂N(C₂H₅)₂ | Colorless needle-like crystals | 239–241 | HCl |

TABLE 11-continued

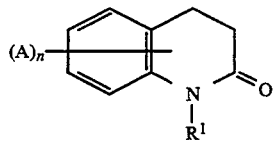

| Example No. | R¹ | n | A | Crystal form (Recrystallization solvent) | Melting point (C.°) | Salt |
|---|---|---|---|---|---|---|
| | | | 8-CH₃ | | | |

TABLE 12

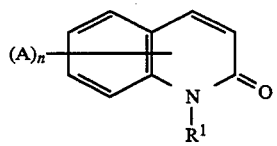

| Example No. | R¹ | n | A | Crystal form (Recrystallization solvent) | Melting point (C.°) | Salt |
|---|---|---|---|---|---|---|
| 246 | H | 2 | 5-N⌒O  6-OCH₃ | Light yellow needle-like crystals (Ethanol-diethyl ether) | 304–307 (decomp.) | HCl |
| 247 | H | 2 | 5-N⌒  6-OCH₃ | Light yellow needle-like crystals (Ethanol-diethyl ether) | 246–251 | HCl |
| 248 | H | 2 | 5-N⌒  6-CH₃ | Light yellow needle-like crystals (Ethanol-diethyl ether) | 184–187 | HCl |

TABLE 13

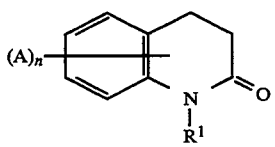

| Example No. | R¹ | n | A | Crystal form (Recrystallization solvent) | Melting point (C.°) | Salt |
|---|---|---|---|---|---|---|
| 249 | H | 2 | 3-(piperidine-N-CH₂-Ph)  8-CH₃ | White powdery substance (Ethanol-n-hexane) | 121–126 | Oxalate |

TABLE 14

[Structure: carbostyril with (A)n substituent on benzene ring and R¹ on nitrogen]

| Example No. | R¹ | n | A | Crystal form (Recrystallization solvent) | Melting point (C.°) | Salt |
|---|---|---|---|---|---|---|
| 250 | CH₃ | 1 | 3-N⟨piperazine⟩N—CH₃ | White powdery substance (Ethanol-diethyl ether) | 203–204 | Oxalate |
| 251 | H | 2 | 3-N⁺⟨bicyclic⟩NHCH₃; 8-CH₃ | Light yellow powdery substance (Water-ethanol-diethyl ether) | 171–174 (decomp.) | Quaternary ammonium chloride |
| 252 | —CH₂CH=CH₂ | 1 | 3-N⟨piperazine⟩N—CH₃ | White powdery substance (Ethanol-diethyl ether) | 169.5–171.5 | Oxalate |
| 253 | —(CH₂)₁₅CH₃ | 1 | 3-N⟨piperazine⟩N—CH₃ | Colorless needle-like crystals (Ethanol-diethyl ether) | 136–136.5 | Oxalate |
| 254 | —CH₂CO₂CH₂—C₆H₅ | 1 | 3-N⟨piperazine⟩N—CH₃ | White powdery substance (Ethanol-water) | 191.5–193.5 (decomp.) | Oxalate |
| 255 | —CH₂CO₂H | 1 | 3-N⟨piperazine⟩N—CH₃ | White powdery substance | Over 300 (decomp.) | — |
| 256 | —CH₂CO₂Na | 1 | 3-N⟨piperazine⟩N—CH₃ | White powdery substance | 160–170 (decomp.) | — |
| 257 | —CH₂CON(C₂H₅)₂ | 1 | 3-N⟨piperazine⟩N—CH₃ | NMR[3] | | |
| 258 | —CH₂CON⟨pyrrolidine⟩ | 1 | 3-N⟨piperazine⟩N—CH₃ | White powdery substance (Ethanol-diethyl ether) | 177–178.5 | — |
| 259 | —CH₂≡CH | 1 | 3-N⟨piperazine⟩N—CH₃ | White powdery substance | 191.5–193 (decomp.) | Oxalate |

[3]N.M.R. (CDCl₃) δ: 1.14(3H, t, J=7Hz), 1.33(3H, t, J=7Hz), 2.37(3H, s), 2.55–2.75(4H, m), 3.27(4H, br.), 3.39(2H, q, J=Hz), 3.51(2H, q, J=7Hz), 5.16(2H, s), 7.00(1H, s), 7.09(1H, t, J=7.5Hz), 7.17(1H, t, J=7.5Hz), 7.35(1H, t, 7.5Hz), 7.48(1H, d, J=7.5Hz).

What is claimed is:

1. A carbostyril compound or a salt thereof represented by the formula (1),

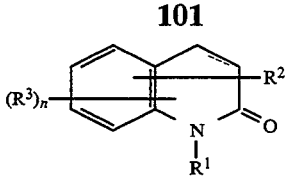

(1)

wherein $R^1$ is hydrogen, $C_1$–$C_{16}$ alkyl, lower alkenyl, lower alkynyl, phenyl-lower alkyl, carboxy-lower alkyl, phenyl-lower alkoxycarbonyl-lower alkyl, amino-lower alkyl which optionally has lower alkyl as the substituents, or carbonyl-lower alkyl which has pyrrolidinyl as substituent on the carbonyl;

$R^2$ is piperazinyl or piperazinyl having 1 to 3 substituents selected from the group consisting of phenyl, hydroxy, phenyl-lower alkyl which optionally has lower alkoxy as substituents on the phenyl ring, $C_1$–$C_{10}$ alkyl which optionally has 1 to 3 hydroxy, lower alkoxy or halogen as substituents, lower alkenyl, lower alkoxycarbonyl lower alkyl, tetrahydrofuryl-lower alkyl, thienyl-lower alkyl, cycloalkyl-lower alkyl, cycloalkyl, benzoyl-lower alkyl which optionally has halogen as substituents on the phenyl ring, pyridyl lower alkyl, lower alkylamino, lower alkynyl, lower alkanoyl-lower alkyl, phenyl-lower alkoxycarbonyl, benzoyl which optionally has lower alkoxy as substituents on the phenyl ring, and a group of the formula

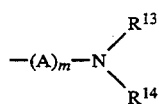

wherein $R^{13}$ and $R^{14}$ are each the same or different, and are each hydrogen, lower alkyl, phenyl-lower alkyl which optionally has lower alkoxy as substituents on the phenyl ring; or wherein $R^{13}$ and $R^{14}$ as well as the adjacent nitrogen being bonded thereto, together with or without other nitrogen or oxygen from 5- or 6-membered heterocyclic ring selected from the group consisting of piperazinyl, piperidinyl, morpholino and pyrrolidinyl, or said 5- or 6-membered heterocyclic ring having lower alkyl as substituents; A is lower alkylene or

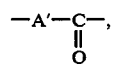

wherein A' is lower alkylene; m is 0 or 1;

$R^3$ is hydrogen, lower alkyl which optionally has 1 to 3 halogen as substituents, lower alkoxy, hydroxy, halogen, carboxyl, phenyl, phenyl-lower alkoxy, lower alkenyloxy, lower alkanoyl-lower alkoxy or lower alkylaminocarbonyl lower alkoxy;

n is 1 or 2;

the carbon-carbon bond between the 3- and 4-positions in the carbostyril skeleton is a single or double bond;

$R^2$ and $R^3$ are each substituted at any position of the 3- to 8-positions in the carbostyril skeleton, provided that $R^2$ and $R^3$ are not substituted at the same position at the same time; and at least one of $R^2$ and $R^3$ is substituted at the 8-position in the carbostyril skeleton;

provided further, that when n is 1 and $R^3$ is hydrogen or lower alkoxy, then $R^2$ is not 1-piperazinyl which optionally has phenyl-lower alkyl which optionally has lower alkoxy as substituents on the phenyl ring, lower alkyl, lower alkenyl, lower alkoxyl-carbonyl-lower alkyl, lower alkynyl or benzoyl which optionally has lower alkoxy as substituents on the phenyl ring, as a substituent at the 4-position in the piperazine ring, and provided that when $R^2$ is bonded at the 4-position in the carbostyril skeleton, and the carbon-carbon bond between the 3- and 4-positions in the carbostyril skeleton is a double bond, then $R^1$ should be neither $C_1$–$C_6$ alkyl, lower alkenyl, propargyl nor phenyl-lower alkyl;

further provided that, when n is 2, the carbon-carbon bond between the 3- and 4-positions in the carbostyril skeleton is a double bond, and 4-methyl-1-piperazinyl or 4-(2-hydroxyethyl)-1-piperazinyl is substituted at the 4-position in the carbostyril skeleton, while $R^1$ is hydrogen and $R^3$ is carboxy which is substituted at the 3-position in the carbostyril skeleton, then the other $R^3$ is not chlorine or bromine which is substituted at the 8-position in the carbostyril skeleton.

2. The carbostyril compound or salt thereof according to claim 1, wherein $R^2$ is piperazinyl which optionally has 1 to 3 substituents selected from the group consisting of phenyl, hydroxy, phenyl-lower alkyl which optionally has lower alkoxy as substituents on the phenyl ring, $C_1$–$C_{10}$ alkyl which optionally has 1 to 3 hydroxy, lower alkoxy or halogen as substituents, lower alkenyl, lower alkoxycarbonyl-lower alkyl, tetrahydrofuryl-lower alkyl, thienyl-lower alkyl, cycloalkyl-lower alkyl, cycloalkyl, benzoyl-lower alkyl which optionally has halogen as substituents on the phenyl ring, pyridyl-lower alkyl, lower alkylamido, lower alkynyl, lower alkanoyl-lower alkyl, phenyl-lower alkoxycarbonyl, and benzoyl which optionally has lower alkyl as substituents on the phenyl ring.

3. The carbostyril compound or salt thereof according to claim 2, wherein $R^2$ is a piperazinyl group which optionally has 1 to 3 substituents selected from the group consisting of $C_3$–$C_8$ cycloalkyl-$C_1$–$C_6$ alkyl and $C_1$–$C_{10}$ alkyl which optionally has 1 to 3 hydroxy, lower alkoxy or halogen as substituents.

4. The carbostyril compound or salt thereof according to claim 3, wherein $R^2$ is piperazinyl which optionally has 1 to 3 $C_1$–$C_{10}$ alkyl which optionally has 1 to 3 hydroxy, lower alkoxy or halogen as substituents.

5. The carbostyril compound or salt thereof according to claim 4, wherein $R^2$ is substituted at the 3-position in the carbostyril skeleton.

6. The carbostyril derivative or salt thereof according to claim 4, wherein $R^2$ is substituted at the 5- or 6-position in the carbostyril skeleton.

7. The carbostyril compound or salt thereof according to claim 5, wherein $R^3$ is $C_1$–$C_{16}$ alkyl which optionally has 1 to 3 halogen as substituents.

8. The carbostyril compound or salt thereof according to claim 6, wherein $R^3$ is $C_1$–$C_{16}$ alkyl which optionally has 1 to 3 halogen as substituents.

9. The carbostyril compound or salt thereof according to claim 5, wherein $R^3$ is halogen.

10. The carbostyril compound or salt thereof according to claim 6, wherein $R^3$ is halogen.

11. The carbostyril compound or salt thereof according to claim 5, wherein $R^3$ is lower alkoxy, hydroxy, carboxyl, phenyl, phenyl-lower alkoxy, lower alkenyloxy, lower alkanoyl-lower alkoxy, or lower alkylaminocarbonyl-lower alkoxy.

12. The carbostyril compound or salt thereof according to claim 6, wherein $R^3$ is lower alkoxy, hydroxy, carboxy, phenyl, phenyl-lower alkoxy, lower alkenyloxy, lower alkanoyl-lower alkoxy or a lower alkylaminocarbonyl-lower alkoxy.

13. The carbostyril compound or salt thereof according to claim 7, wherein $R^3$ is substituted at the 8-position in the carbostyril skeleton.

14. The carbostyril compound or salt thereof according to claim 8, wherein $R^3$ is substituted at the 8-position in the carbostyril skeleton.

15. The carbostyril compound or salt thereof according to claim 13, wherein $R^1$ is hydrogen.

16. The carbostyril compound or salt thereof according to claim 14, wherein $R^1$ is hydrogen.

17. The carbostyril compound or salt thereof according to claim 13, wherein $R^1$ is $C_1$-$C_{16}$ alkyl, lower alkenyl, lower alkynyl or phenyl-lower alkyl.

18. The carbostyril compound or salt thereof according to claim 14, wherein $R^1$ is $C_1$-$C_{16}$ alkyl, lower alkenyl, lower alkynyl or phenyl-lower alkyl.

19. 3-(4-Methyl-1-piperazinyl)-8-methylcarbostyril.

20. 3-(4-Cyclopropylethyl-1-piperazinyl)-8-methylcarbostyril.

21. The carbostyril compound or salt thereof according to claim 1 wherein the carbostyril compound or salt thereof is represented by the formula (1A):

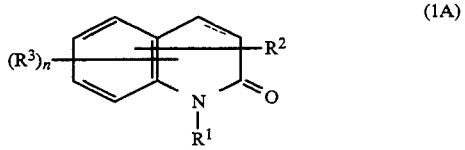

wherein
$R^1$ is hydrogen, $C_1$-$C_{16}$ alkyl, or phenyl-$C_1$-$C_6$ alkyl;
$R^2$ is piperazinyl or piperazinyl which optionally has 1 to 3 substituents selected from the group consisting of phenyl, hydroxy, phenyl-$C_1$-$C_6$ alkyl which optionally has $C_1$-$C_6$ alkoxy as substituents on the phenyl ring, $C_1$-$C_{10}$ alkyl which optionally has 1 to 3 $C_1$-$C_6$ alkoxy or halogen as substituents, $C_2$-$C_6$ alkenyl, tetrahydrofuryl-$C_1$-$C_6$ alkyl, $C_3$-$C_8$ cycloalkyl, benzoyl-$C_1$-$C_6$ alkyl which optionally has halogen as substituents on the phenyl ring, pyridyl-$C_1$-$C_6$ alkyl, $C_1$-$C_6$ alkyl-amino, $C_2$-$C_6$ alkynyl, $C_1$-$C_6$ alkanoyl-$C_1$-$C_6$ alkyl, benzoyl which optionally has $C_1$-$C_6$ alkoxy as substituents on the phenyl ring, and a group of the formula:

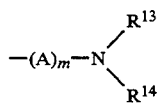

wherein
$R^{13}$ and $R^{14}$ are each the same or different, and are each hydrogen, lower alkyl, phenyl-$C_1$-$C_6$ alkyl which optionally has lower alkoxy as substituents on the phenyl ring; further $R^{13}$ and $R^{14}$ as well as the adjacent nitrogen being bonded thereto, together with or without other nitrogen or oxygen, optionally form a 5- or 6-membered heterocyclic group selected from the group consisting of piperazinyl, piperidinyl, morpholino and pyrrolidinyl, or said 5- or 6-membered heterocyclic group having $C_1$-$C_6$ alkyl as substituents; A is $C_1$-$C_6$ alkylene, m is 0 or 1;
$R^3$ is hydrogen, $C_1$-$C_6$ alkyl which optionally has 1 to 3 halogen as substituents, $C_1$-$C_6$ alkoxy, hydroxy, halogen, phenyl-$C_1$-$C_6$ alkenyloxy;
n is 1 or 2;
the carbon-carbon bond between 3- and 4-positions in the carbostyril skeleton is a single or double bond; and
$R^2$ and $R^3$ are each substituted at any one of 3- to 8-positions in the carbostyril skeleton.

22. The carbostyril compound or salt thereof according to claim 21, wherein $R^2$ is piperazinyl which optionally has 1 to 3 substituents selected from the group consisting of $C_3$-$C_8$ cycloalkyl-$C_1$-$C_6$ alkyl and $C_1$-$C_{10}$ alkyl which optionally has 1 to 2 $C_1$-$C_6$ alkoxy or halogen as substituents.

23. The carbostyril compound or salt thereof according to claim 22, wherein $R^2$ is piperazinyl which optionally has 1 to 3 $C_1$-$C_{10}$ alkyl as substituents, and wherein said $C_1$-$C_{10}$ alkyl optionally has 1 to 3 $C_1$-$C_6$ alkoxy or halogen as substituents.

24. The carbostyril compound or salt thereof according to claim 23, wherein $R^2$ is substituted at 3-position in the carbostyril skeleton; $R^3$ is $C_1$-$C_6$ alkyl which optionally has 1 to 3 halogen as substituents, or halogen; $R^3$ is substituted at 8-position in the carbostyril skeleton; and $R^1$ is hydrogen.

25. The carbostyril compound or salt thereof according to claim 23, wherein $R^2$ is substituted at 5- or 6-position in the carbostyril skeleton; $R^3$ is $C_1$-$C_6$ alkyl which optionally has 1 to 3 halogen substituents, or halogen; $R^3$ is substituted at 8-position in the carbostyril skeleton; and $R^1$ is hydrogen.

26. A carbostyril compound or salt thereof represented by the formula

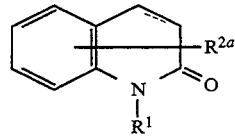

wherein
$R^1$ is hydrogen, $C_1$-$C_{16}$ alkyl, lower alkenyl, lower alkynyl, phenyl-lower alkyl, carboxy-lower alkyl, phenyl-lower alkoxycarbonyl-lower alkyl, amino-lower alkyl which optionally has lower alkyl as the substituents, or carbonyl-lower alkyl which has pyrrolidinyl as substituent on the carbonyl;
$R^{2a}$ is a piperazinyl group having 1 to 3 $C_1$-$C_{10}$ alkyl substituents and $R^{2a}$ is bonded at the 3- or 4-position in the carbostyril skeleton; and
the carbon-carbon bond between the 3- and 4-positions of the carbostyril skeleton is a single or double bond.

27. The carbostyril compound or salt thereof according to claim 26, wherein the carbostyril compound is represented by the formula:

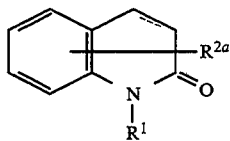

wherein
R¹ is hydrogen, phenyl-$C_1$–$C_6$ alkyl, $C_1$–$C_6$ alkyl, $C_2$–$C_6$ alkenyl, $C_2$–$C_6$ alkynyl, or phenyl-$C_1$–$C_6$ alkoxy-carbonyl-$C_1$–$C_6$ alkyl.

28. The carbostyril compound or salt thereof according to claim 1, wherein R² is piperazinyl which optionally has 1 to 3 substituents represented by a group of the formula

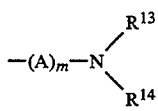

wherein $R^{13}$, $R^{14}$, and A and m are the same as defined in claim 1.

29. A pharmaceutical composition for improving arrhythmia containing, as the active ingredient, a carbostyril compound as claimed in claim 1, and a pharmaceutically acceptable carrier.

30. The pharmaceutical composition according to claim 29, wherein R² is a group of the formula

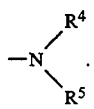

31. The pharmaceutical composition according to claim 30, wherein R² is substituted at the 3-position in the carbostyril skeleton.

32. The pharmaceutical composition according to claim 30, wherein R² is substituted at the 5- or 6-position in the carbostyril skeleton.

33. The pharmaceutical composition according to claim 32, wherein R³ is substituted at the 8-position in the carbostyril skeleton.

34. The pharmaceutical composition according to claim 31, wherein R³ is substituted at the 8-position in the carbostyril skeleton.

35. The pharmaceutical composition according to claim 34, wherein R¹ is hydrogen.

36. The pharmaceutical composition according to claim 33, wherein R¹ is hydrogen.

37. The pharmaceutical composition according to claim 29, wherein the active ingredient is 3-(4-methyl-1-piperazinyl)-8-methylcarbostyril.

38. The pharmaceutical composition according to claim 29, wherein the active ingredient is 3-(4-methyl-1-piperazinyl)-8-methylcarbostyril.

39. A pharmaceutical composition for improving arrhythmia containing, as the active ingredient, a carbostyril compound or salt thereof represented by the formula (1A) as claimed in claim 21 and pharmaceutically acceptable carriers.

40. A pharmaceutical composition for improving arrhythmia containing, as the active ingredient, a carbostyril compound or slat thereof represented by the formula (1A) as claimed in claim 22, and pharmaceutically acceptable carriers.

41. A pharmaceutical composition for improving arrhythmia containing, as the active ingredient, a carbostyril compound or salt thereof represented by the formula as claimed in claim 26, and pharmaceutically acceptable carriers.

* * * * *